United States Patent
Paddon et al.

(10) Patent No.: US 11,946,087 B2
(45) Date of Patent: Apr. 2, 2024

(54) CO-PRODUCTION OF A SESQUITERPENE AND A CAROTENOID

(71) Applicant: AMYRIS BIO PRODUCTS PORTUGAL, UNIPESSOAL, LDA, Oporto (PT)

(72) Inventors: Christopher J. Paddon, Pacifica, CA (US); Victor Holmes, Oakland, CA (US); Chia-Hong Tsai, Martinez, CA (US); Yoseph Tsegaye, Emeryville, CA (US); Phoebe Yeh, Emeryville, CA (US)

(73) Assignee: AMYRIS BIO PRODUCTS PORTUGAL, UNIPESSOAL, LDA, Oporto (PT)

( * ) Notice: Subject to any disclaimer, the term of this patent is extended or adjusted under 35 U.S.C. 154(b) by 1259 days.

(21) Appl. No.: 16/480,286

(22) PCT Filed: Jan. 25, 2018

(86) PCT No.: PCT/US2018/015326
§ 371 (c)(1),
(2) Date: Jul. 23, 2019

(87) PCT Pub. No.: WO2018/140652
PCT Pub. Date: Aug. 2, 2018

(65) Prior Publication Data
US 2020/0032314 A1 Jan. 30, 2020

Related U.S. Application Data

(60) Provisional application No. 62/450,492, filed on Jan. 25, 2017.

(51) Int. Cl.
*C12P 23/00* (2006.01)
*A23K 10/16* (2016.01)
(Continued)

(52) U.S. Cl.
CPC .............. *C12P 23/00* (2013.01); *A23K 10/16* (2016.05); *A23K 20/179* (2016.05); *C12N 1/18* (2013.01)

(58) Field of Classification Search
CPC .......... C12P 23/00; C12P 5/007; A23K 10/16; A23K 20/179; C12N 1/18
See application file for complete search history.

(56) References Cited

U.S. PATENT DOCUMENTS

2009/0142322 A1 6/2009 Ye
2015/0211024 A1* 7/2015 Garcez Lopes ........ C12N 15/52
435/157

FOREIGN PATENT DOCUMENTS

WO WO 2008/073367 A1 6/2008
WO WO 2009/126890 A2 10/2009
WO WO 2014/025941 A1 2/2014

OTHER PUBLICATIONS

Gao, Connie Ying, and Jennifer L. Pinkham. "Tightly regulated, β-estradiol dose-dependent expression system for yeast." Biotechniques 29.6 (2000): 1226-1231. (Year: 2000).*

(Continued)

*Primary Examiner* — Lora E Barnhart Driscoll
*Assistant Examiner* — Candice Lee Swift
(74) *Attorney, Agent, or Firm* — SQUIRE PATTON BOGGS (US) LLP

(57) ABSTRACT

Provided herein are compositions and methods for co-production and recovery of two or more isoprenoids from a single recombinant cell.

40 Claims, 15 Drawing Sheets

(51) Int. Cl.
A23K 20/179 (2016.01)
C12N 1/18 (2006.01)

(56) References Cited

OTHER PUBLICATIONS

Farmer, William R., and James C. Liao. "Precursor balancing for metabolic engineering of lycopene production in *Escherichia coli*." Biotechnology progress 17.1 (2001): 57-61. (Year: 2001).*

Urreta, Iratxe, et al. "Revalorization of Neochloris oleoabundans biomass as source of biodiesel by concurrent production of lipids and carotenoids." Algal research 5 (2014): 16-22. (Year: 2014).*

Varela, Joao C., et al. "Production of carotenoids by microalgae: achievements and challenges." Photosynthesis research 125.3 (2015): 423-436. (Year: 2015).*

Brown, Jeff, et al. "Farnesene-derived base oils." Environmentally friendly and biobased lubricants. CRC Press, 2016. 3-34. (Year: 2016).*

Pubchem1; https://pubchem.ncbi.nlm.nih.gov/compound/Lutein#section=Other-MS (Year: 2023).*

Pubchem2; https://pubchem.ncbi.nlm.nih.gov/compound/Astaxanthin (Year: 2023).*

Li, Qian, et al. "Enhancing beta-carotene production in *Saccharomyces cerevisiae* by metabolic engineering." FEMS microbiology letters 345.2 (2013): 94-101. (Year: 2013).*

Tippmann, Stefan, Jens Nielsen, and Sakda Khoomrung. "Improved quantification of farnesene during microbial production from *Saccharomyces cerevisiae* in two-liquid-phase fermentations." Talanta 146 (2016): 100-106. (Year: 2016).*

International Search report and written opinion dated Jun. 25, 2018 for PCT/US2018/015326, 33 pages.

Hull et al., "Co-production of ethanol and squalene using a *Saccharomyces cerevisiae* ERG1 (squalene epoxidase) mutant and agro-industrial feedstock", Biotechnology for Biofuels, vol. 7, No. 1, Sep. 24, 2014, p. 133, XP021200528; DOI: 10.1186/S13068-014-0133-7.

Tian et al., "The *Arabidopsis* LUTI locus encodes a member of the cytochrome P450 family that is required for carotenoid epsilon-ring hydroxylation activity", Proceedings of the National Academy of Sciences, vol. 101, No. 1, Jan. 6, 2004, pp. 402-407, XP003001336.

* cited by examiner

US 11,946,087 B2

CO-PRODUCTION OF A SESQUITERPENE AND A CAROTENOID

The present application is a national phase of PCT/US2018/015326, filed Jan. 25, 2018, which claims the benefit of U.S. provisional application No. 62/450,492, filed Jan. 25, 2017, entitled Co-Production of Isoprenoids, the contents of which are hereby incorporated by reference in their entireties.

1. FIELD OF THE INVENTION

Provided herein are compositions and methods useful for co-production of two or more isoprenoids from microbial cells during fermentation, and valorization of spent microbial cells.

2. BACKGROUND OF THE INVENTION

Isoprenoids are ubiquitous in nature. They comprise a diverse family of over 40,000 individual products, many of which are vital to living organisms. Isoprenoids serve to maintain cellular fluidity, electron transport, and other metabolic functions. A vast number of natural and synthetic isoprenoids have many applications, such as pharmaceuticals, cosmetics, perfumes, pigments and colorants, fungicides, antiseptics, nutraceuticals, and fine chemical intermediates.

In particular, carotenoids are distributed in fish, animals, and crustaceans. The red carotenoid astaxanthin has been used as a pigmentation source in industry, for example, for salmonid flesh in the aquaculture industry. Ukibe et al., 2009, *Appl. Environ. Microbiol.* 75:7205-7211. Astaxanthin constitutes one of the largest costs of salmon feed, and is required for the red color of salmon flesh.

Traditionally, isoprenoids have been manufactured by extraction from natural sources such as plants, microbes, and animals. However, the yield by way of extraction is usually very low due to a number of profound limitations. First, most isoprenoids accumulate in nature in only small amounts. Second, the source organisms in general are not amenable to the large-scale cultivation that is necessary to produce commercially viable quantities of a desired isoprenoids.

Advances have been made in in the field of synthetic biology, and currently a number of isoprenoids are being produced at an industrial scale. Nevertheless, given the very large quantities of isoprenoid products needed for many commercial applications, there remains a need to improve systems and fermentation procedures that can produce isoprenoids more efficiently than available with current technologies. Also, efficient production of carotenoids, such as astaxanthin, from renewable source is desirable.

Embodiments of the present invention meet these and other needs.

3. SUMMARY

Provided herein are compositions and methods useful for co-production of two or more isoprenoids from host cells genetically modified to produce isoprenoids, and valorization of spent host cells, in particular, spent microbial host cells.

In one aspect, provided herein are host cells genetically modified to produce a first isoprenoid and further genetically modified to produce a second isoprenoid. Certain embodiments described herein generally relate to microorganisms (e.g. non-naturally occurring microorganisms) that produce at least both a sesquiterpene such as farnesene and a carotenoid, for example astaxanthin, a xanthophyll, a ketocarotenoid, or another carotenoid. In certain embodiments, the host cells are capable of producing farnesene and a carotenoid, such as astaxanthin, a xanthophyll, a ketocarotenoid, or another carotenoid. In certain embodiments, the host cells are capable of producing farnesene and astaxanthin.

In another aspect, provided herein are host cells capable of producing both a sesquiterpene such as farnesene and a carotenoid, for example astaxanthin, a xanthophyll, a ketocarotenoid, or another carotenoid. In certain embodiments, the host cells comprise one or more nucleic acids encoding at least one of each enzyme of the mevalonate pathway, described herein. In certain embodiments, the host cells further comprise a nucleic acid encoding a terpene synthase, as described herein. In certain embodiments, the terpene synthase is farnesene synthase. In certain embodiments, the host cells further comprise one or more nucleic acids encoding enzymes of a pathway capable of producing carotenoid, such as astaxanthin, a xanthophyll, a ketocarotenoid, or another carotenoid. In certain embodiments, the carotenoid is astaxanthin. In certain embodiments, these enzymes are selected from the group consisting of phytoene synthase/lycopene cyclase, phytoene desaturase, astaxanthin synthase cytochrome-P450 hydroxylase/ketolase, cytochrome-P450 reductase, β-carotene ketolase, β-carotene hydroxylase, β-carotene hydroxylase, β-carotene ketolase, β-carotene hydroxylase, and combinations thereof. In certain embodiments, the various enzymes of these embodiments are encoded by a plurality of nucleic acids. In certain embodiments, a single nucleic acid encodes each enzyme of these embodiments. In certain embodiments, the various enzymes of these embodiments are encoded by a plurality of heterologous nucleic acids. In certain embodiments, a single heterologous nucleic acid encodes each enzyme of these embodiments.

In certain embodiments, a substantial amount of the sesquiterpene is released from the cells where it can be recovered. In certain embodiments, a substantial amount of the carotenoid remains in the cells (or remains associated with the cell biomass) where it can be recovered by recovering the cell mass. In certain embodiments, production of the sesquiterpene and the carotenoid may occur at or around the same time (first embodiment of FIG. 4). In certain embodiments, there may be a genetic switch such that biomass and the sesquiterpene are produced initially followed by production of the carotenoid in the biomass after the genetic switch has been activated (second embodiment of FIG. 4). In certain embodiments, the sesquiterpene and biomass can be separated by differential centrifugation with the sesquiterpene in a low-density liquid phase, and biomass with pelleted solid material. In a first embodiment, the pelleted biomass contains the carotenoid. In a second embodiment, the biomass can be resuspended in medium and subjected to a genetic switch so as to activate carotenoid production. In the second embodiment, after incubation under suitable conditions for a suitable time period, the biomass can again be pelleted, and the pelleted biomass containing the carotenoid can be produced.

There are several advantages provided by present embodiments. One advantage of producing two or more isoprenoids (e.g., carotenoids such as astaxanthin in the same yeast cells that produce a sesquiterpene such as farnesene) is that multiple isoprenoid products can be made in a single fermentation run after inoculation. Therefore, the same cellular biomass grown during the initial phase of fermentation can be used to produce two or more isoprenoid products. If separate fermentations were to be run for two or more isoprenoids, then most operation units need to be duplicated (e.g., inoculation, growth of the seed strain, growth and operation of the production fermenters), leading to a concomitant increase in the overall cost of production of the two or more isoprenoids. Furthermore, the cost of carbon sources for fermentation would be significantly increased if two separate fermentations were run. This is because growth of biomass is a significant use of carbon source, and biomass production would be required in both fermentations, leading to a multi-fold increase in the requirement for carbon source to produce biomass.

There are additional advantages. For example, in certain embodiments, multiple isoprenoid products produced in host cells are predominantly present in different phases. For example, a larger isoprenoid (e.g., a C40 isoprenoid) is predominantly associated with cells as its size does not allow its release from cells into fermentation medium, and a smaller isoprenoid (e.g., C15 isoprenoid) is predominantly released into the fermentation medium. The presence of two target isoprenoids in different phases can allow easy separation of the two isoprenoid products. Furthermore, the host cells resulting from the production of the sesquiterpene are, without the production of carotenoids, of low value, being either a waste product to be disposed of, or of minimal value as an animal feed component. Production of carotenoids, for example astaxanthin, in the yeast cells dramatically increases the value of the yeast that results from the sesquiterpene production. The yeast containing carotenoids have significantly enhanced value. For example, astaxanthin-containing yeast could be sold into the salmon feed market to replace the use of synthetic astaxanthin which constitutes one of the largest costs of salmon feed, and is required for the red color of salmon flesh.

4. BRIEF DESCRIPTION OF THE FIGURES

Figure 6:
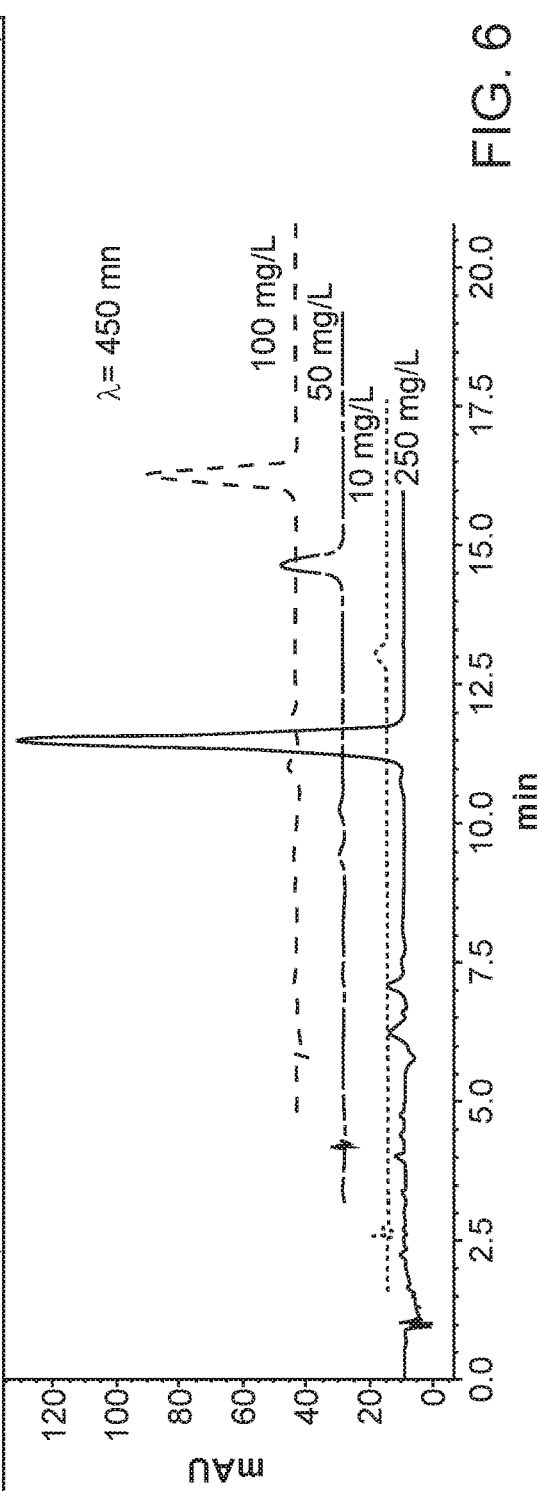

FIG. 6 illustrates that beta-carotene calibration standards show increase in the peak area with the increase in concentration. Shown in FIG. 6 is an overlay of raw HPLC chromatograms of the calibration standards at all levels. The peaks were separated and monitored at 450 nm as reported in the method section.

Figure 7:
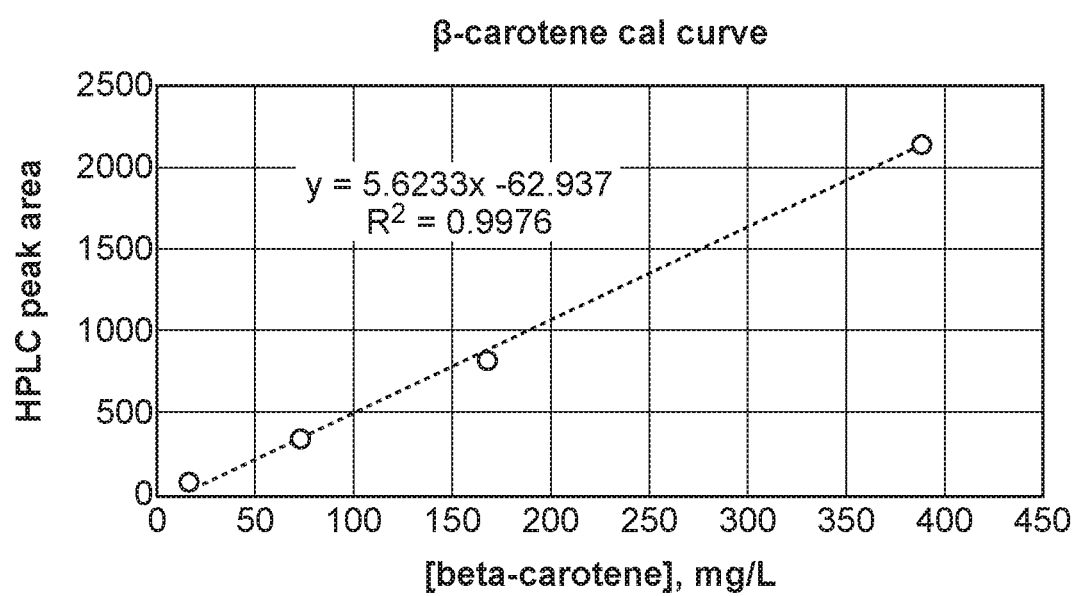

FIG. 7 illustrates the calibration curve showing a very good correlation of peak area vs. concentration of the analyte ($R^2$>0.99).

Figure 8:
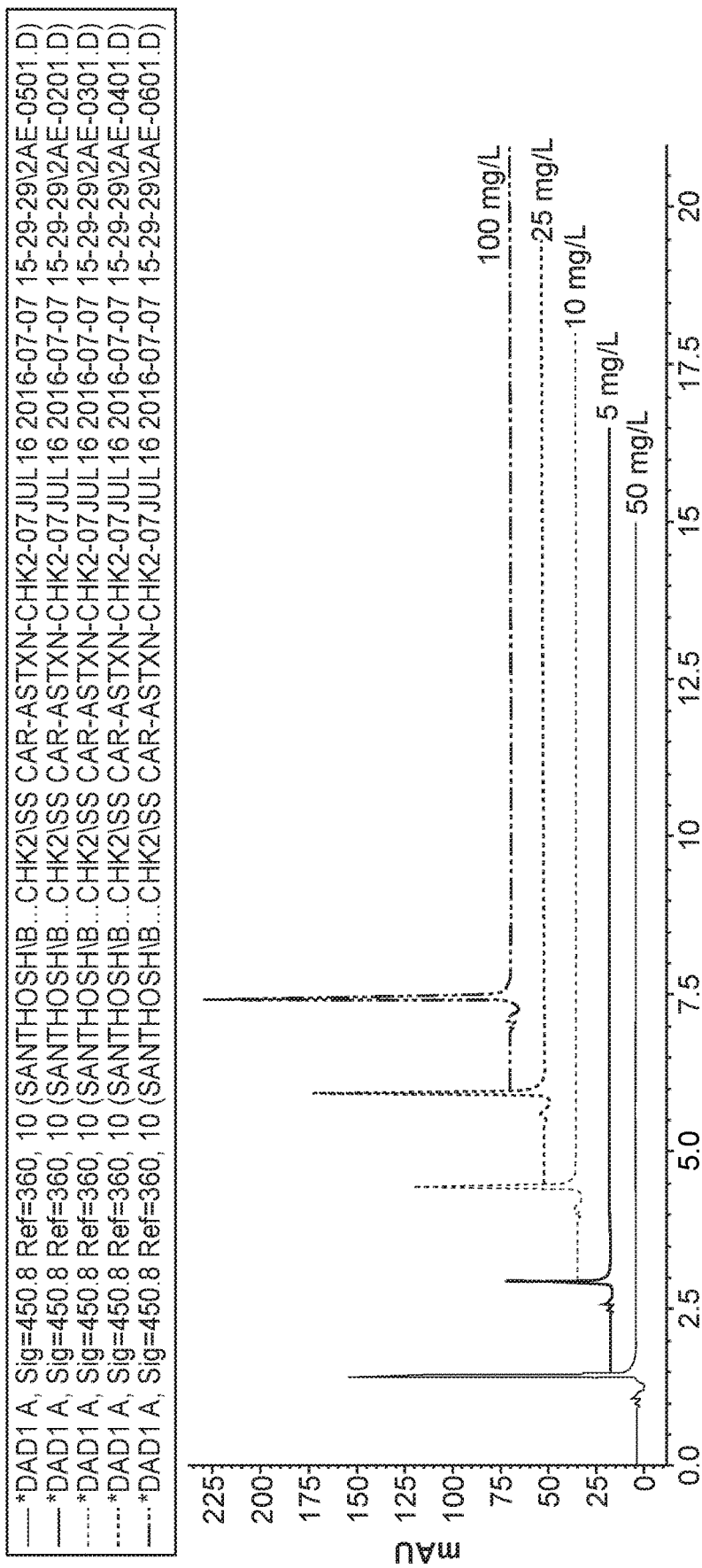

FIG. 8 illustrates that astaxanthin elutes around 1.4 min and shows a clear increase in peak area with the increase in concentration. The concentrations reported here are an estimate resulting from a serial dilution in acetone of an approximately 1 mg/mL stock in DMSO. Nevertheless, this figure clearly shows that astaxanthin and carotene can be separated from each other using the current conditions. The peaks were monitored at 480 nm and we did not observe any significant change in peak response even when it was measured at 450 nm (typically used for beta-carotene).

Figure 9:
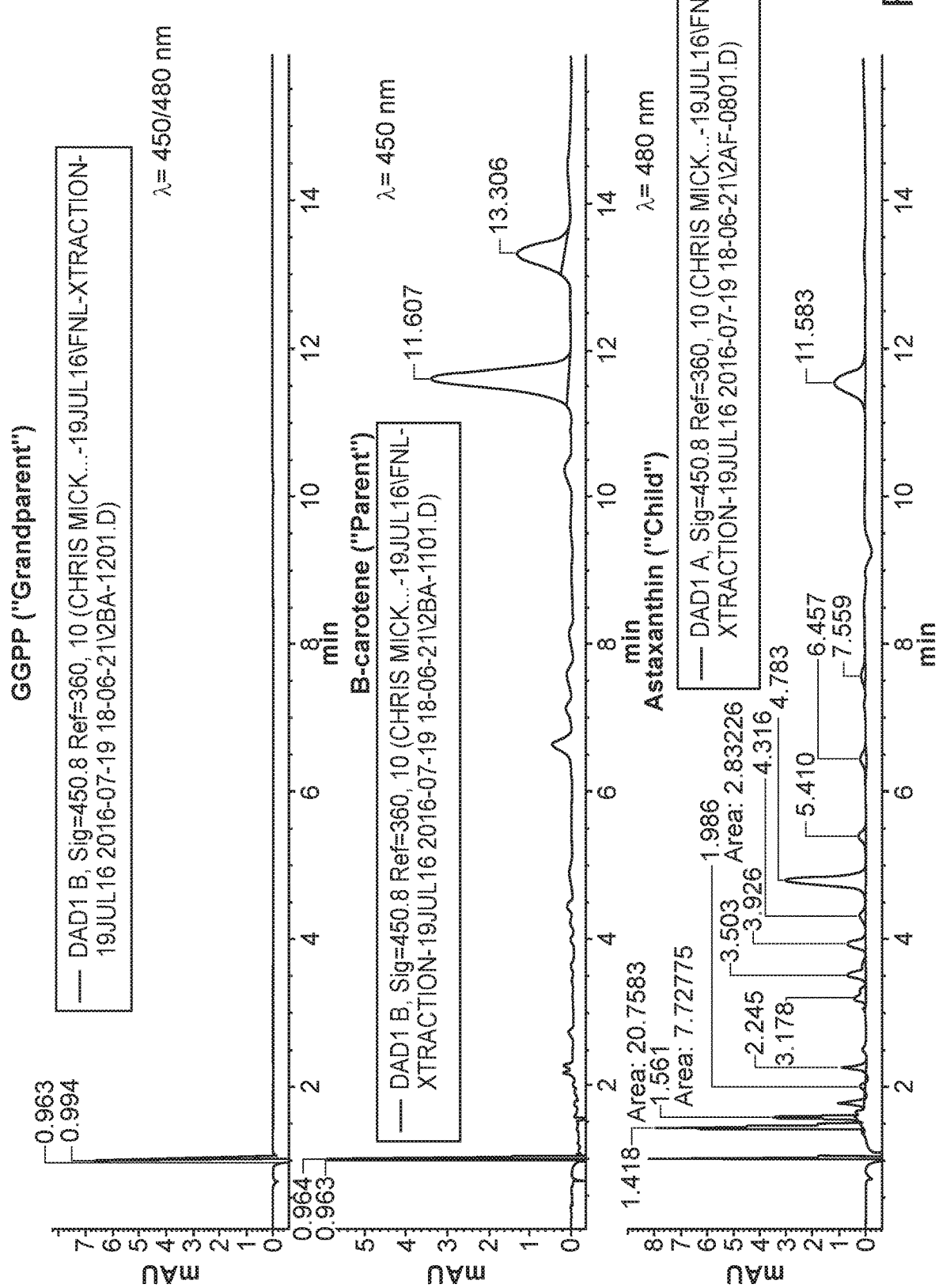

FIG. 9 shows various strain samples extracted and analyzed using the conditions mentioned in this report. A) GGPPS grandparent strain with no downstream genes, expectedly, showing no signs of beta-carotene or astaxanthin. B) Parent strain containing only genes encoding for beta-carotene clearly shows the presence of the same after extraction and analysis. The identity of the second peak at 13.3 min is not clear at the moment. It is likely to be the dihydro analog of beta-carotene which is a known by-product of crtYB gene (ref: Verwaal et al, 2007). C) Daughter strain clearly shows the presence of astaxanthin at 1.4 min along with beta-carotene and other potential carotenoids. The identities of other smaller peaks are not known and they could potentially be other downstream carotenoids (more polar than beta-carotene, likely oxygenated forms) or may also contain some degradation or transformed analogs of astaxanthin.

Figure 10:
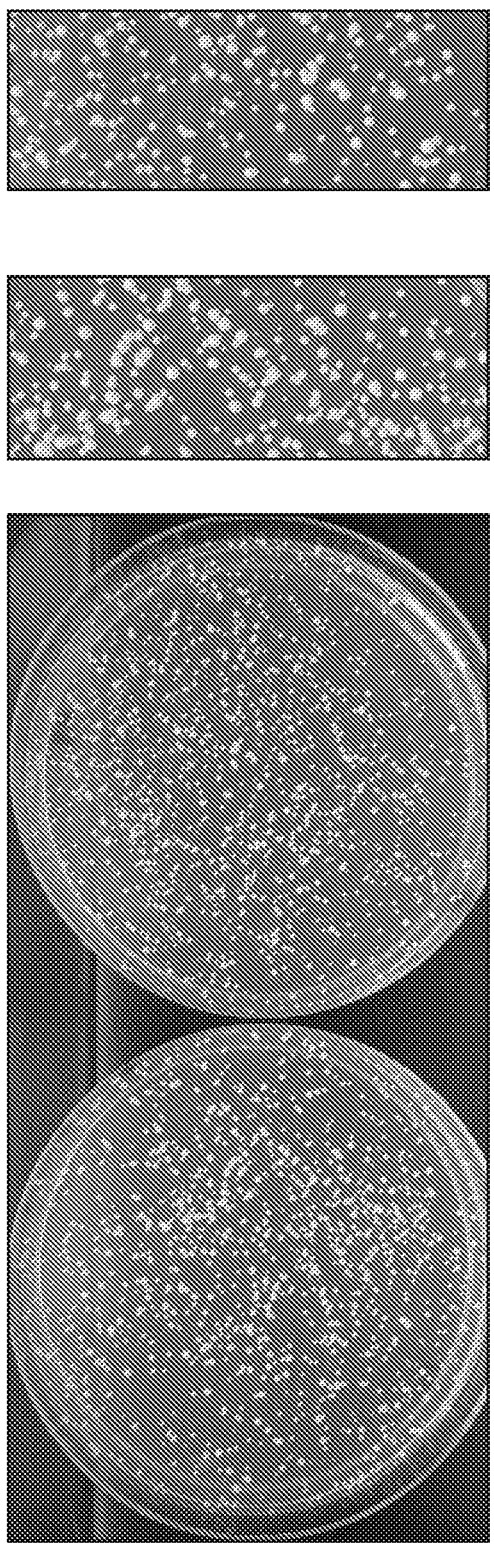

FIG. 10 illustrates representative plates showing the yellow/orange colonies. A, C. Colonies in this plate look light yellow. B. Colonies in this plate look orange.

Figure 11:
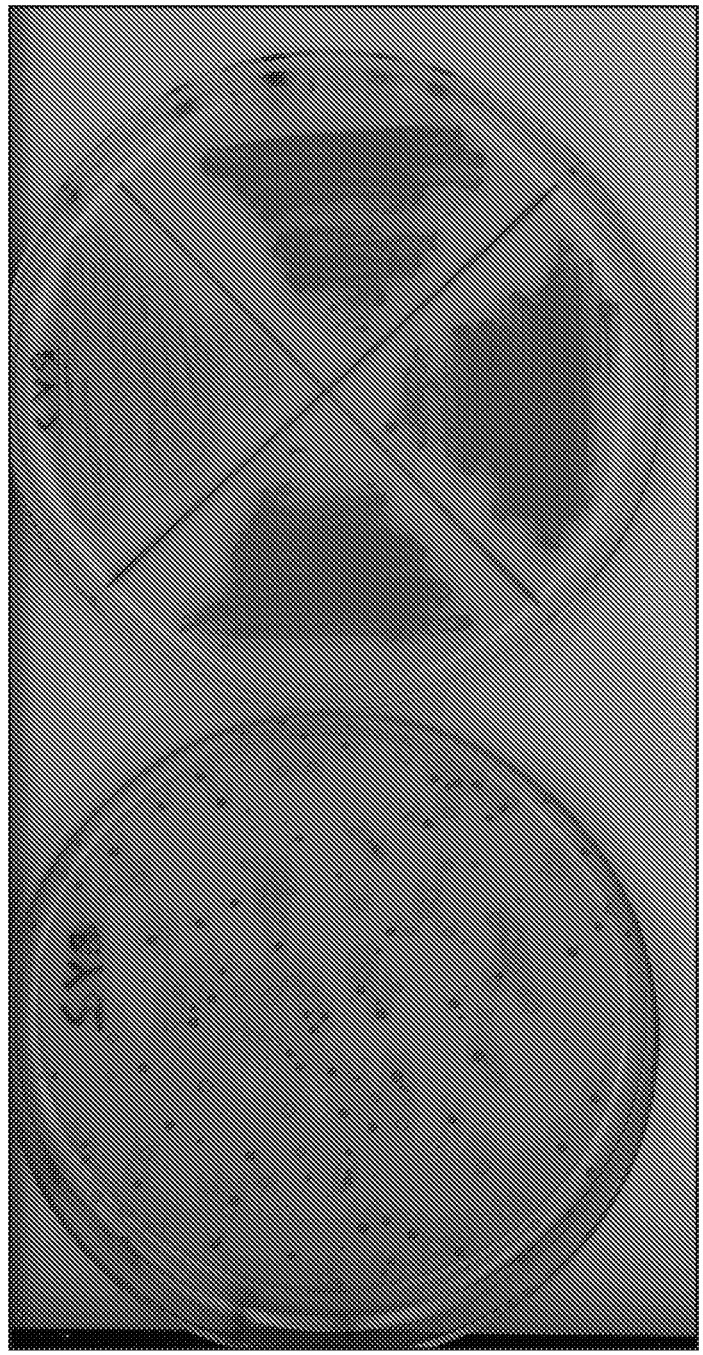

FIG. 11 illustrates Representative plates showing the red co-production strain colonies. Left, transformation plate with individual colonies. Right, restreaking of the selected clones. Yellow colonies comprises nucleic acids encoding the biosynthetic pathway to beta-carotene. Red colonies are the strains making astaxanthin.

Figure 12:
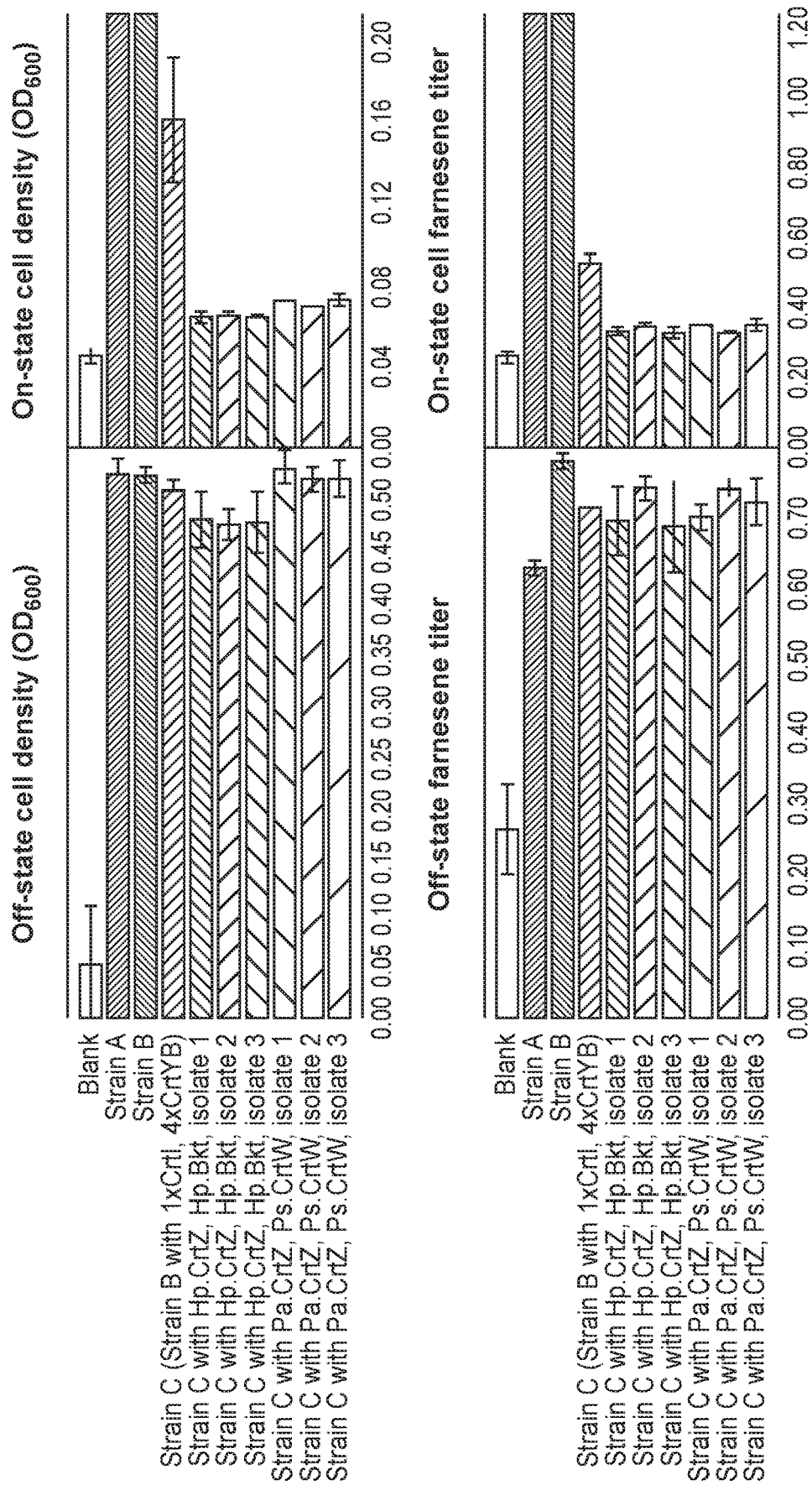

FIG. 12 shows production of farnesene by strains engineered to produce carotenoids (β-carotene or astaxanthin). The farnesene production strain engineered with carotenoid biosynthetic pathway produced farnesene as shown in FIG. 12. These strains also produced carotenoids (data not shown).

Figure 13A:
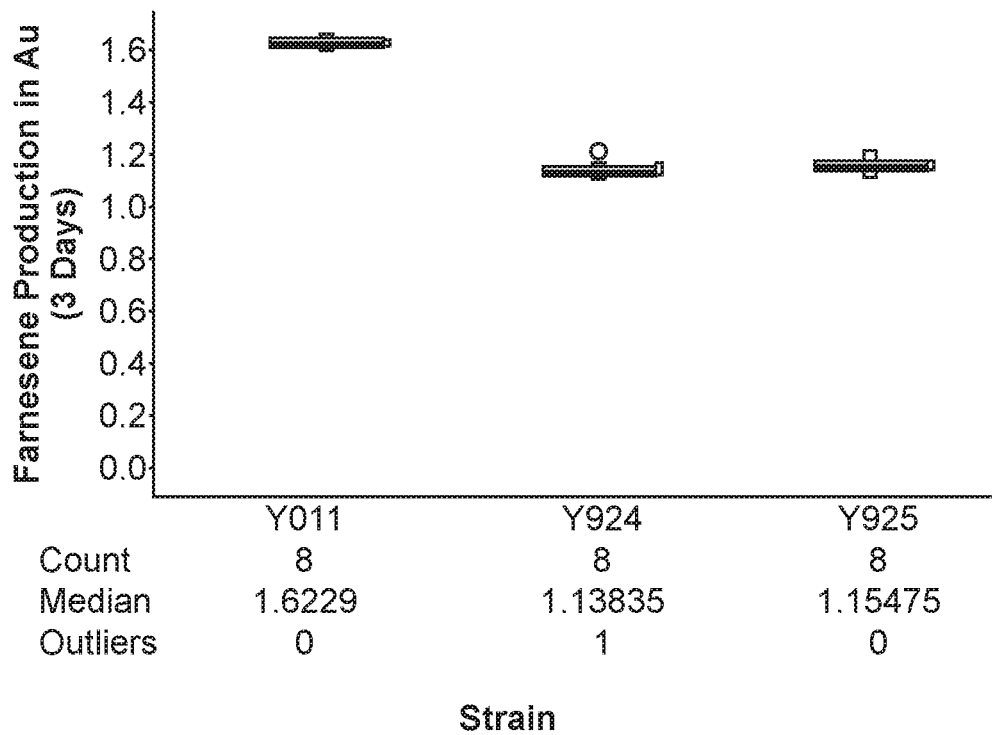
Figure 13B:
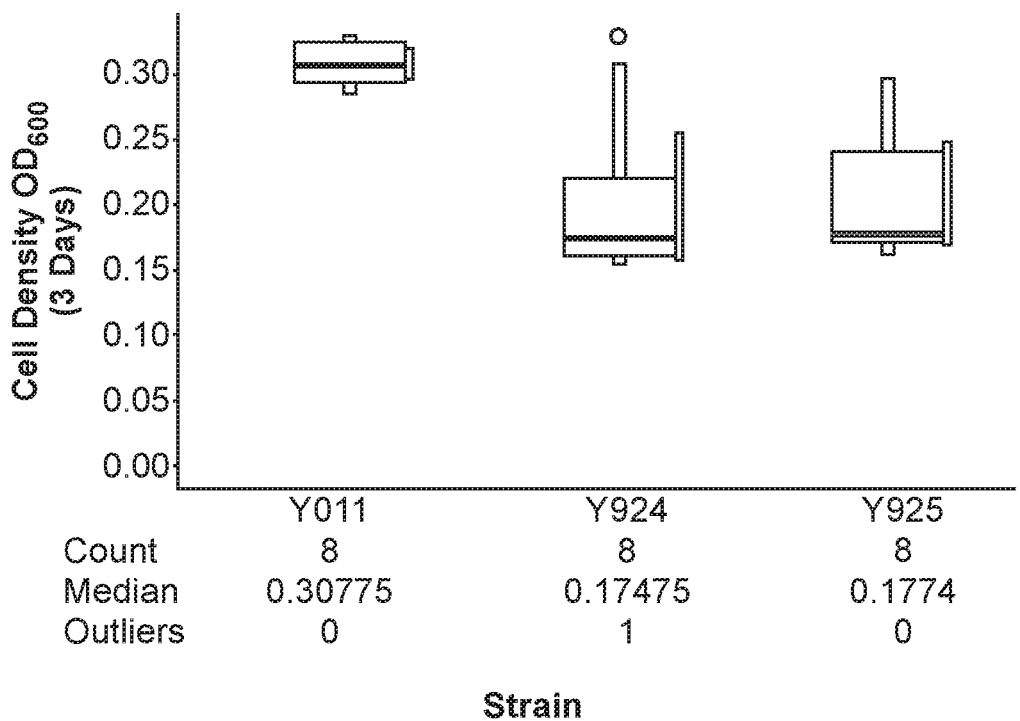

FIGS. 13A and 13B show farnesene production (13A) and growth (optical density: 13B) for several strains.

Figure 14A:
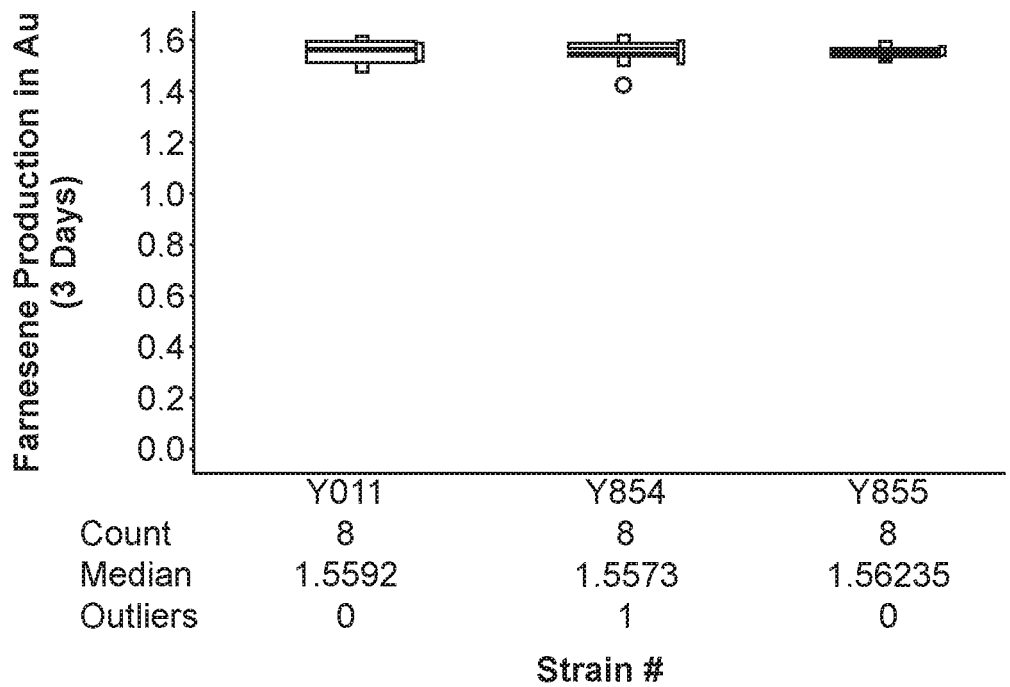
Figure 14B:
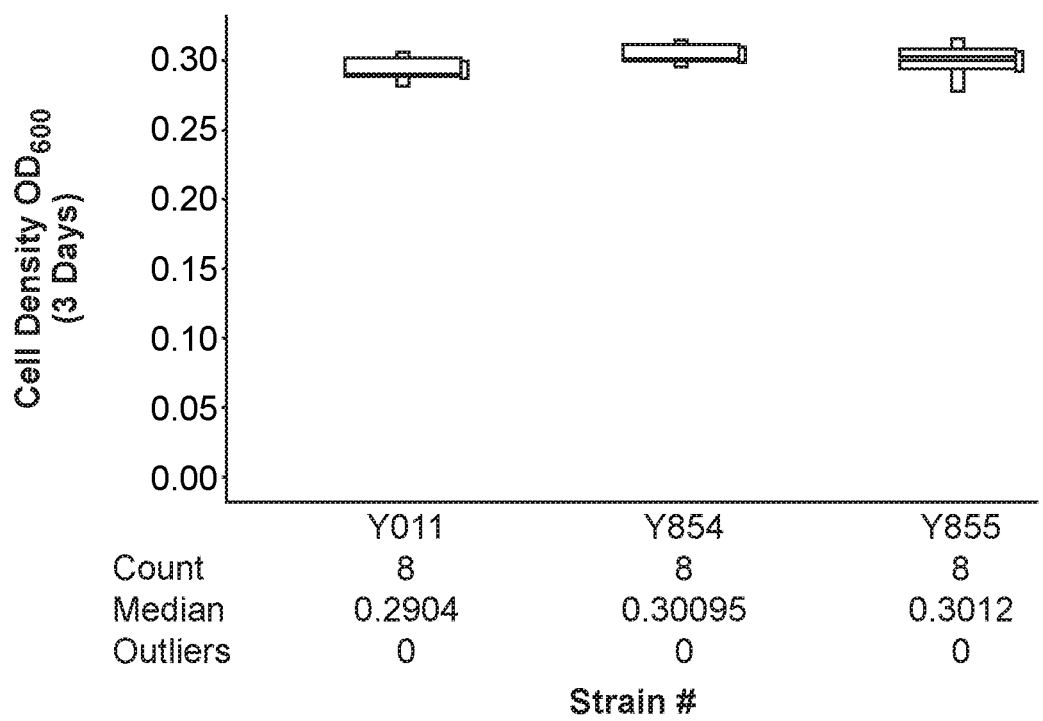

FIG. 14A shows farnesene production for several strains. FIG. 14B shows growth (optical density) for several strains.

5. DETAILED DESCRIPTION OF THE EMBODIMENTS

5.1 Definitions

The terms "isoprenoid," "isoprenoid compound," "terpene," "terpene compound," "terpenoid," and "terpenoid compound" are used interchangeably herein, and refer to any compound that is capable of being derived from isopentenyl pyrophosphate (IPP). The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid." Isoprenoid compounds include, but are not limited to, monoterpenes, diterpenes, triterpenes, sesquiterpenes, and polyterpenes.

The term "carotenoid" refers to a compound composed of a polyene backbone which is condensed from a five-carbon isoprene unit. Carotenoids can be acyclic or terminated with one (monocyclic) or two (bicyclic) cyclic end groups. The term "carotenoid" may include both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids that are particularly suitable in the present invention are monocyclic and bicyclic carotenoids.

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" refers to any enzyme that enzymatically modifies IPP, DMAPP, or a polyprenyl pyrophosphate, such that a terpenoid precursor compound is produced. The term "terpene synthase" includes enzymes that catalyze the conversion of a prenyl diphosphate into an isoprenoid or isoprenoid precursor.

The word "pyrophosphate" is used interchangeably herein with "diphosphate" and refers to two phosphate groups covalently bonded. Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The mevalonate pathway is illustrated schematically in FIG. 1. The "top half" of the mevalonate pathway refers to the enzymes responsible for the conversion of acetyl-CoA to mevalonate.

The term "I-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate, where DXP pathway comprises enzymes that catalyze the reaction. Typical enzymes of the DXP pathway include DXS, DXR, CMS, CMK, MCS, HDS, and HDR. Dxs is 1-deoxy-D-xylulose-5-phosphate synthase; Dxr is 1-deoxy-D-xylulose-5-phosphate reductoisomerase (also known as IspC); IspD (CMS) is 4-diphosphocytidyl-2C-methyl-D-erythritol synthase; IspE (CMK) is 4-diphosphocytidyl-2C-methyl-D-erythritol synthase; IspF (MCS) is 2C-methyl-D-erythritol 2,4-cyclodiphosphate synthase; IspG (HDS) is 1-hydroxy-2-methyl-2-(E)-butenyl 4-diphosphate synthase; and IspH (HDR) is isopentenyl/dimethylallyl diphosphate synthase.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the formation of prenyl diphosphates of various chain lengths.

As used herein, the term "target compound(s)" refers to compounds to be recovered from a host cell genetically modified with one or more heterologous nucleic acids encoding enzymes of a biosynthetic pathway for producing the target compound(s), and does not include metabolites which may be incidentally produced during the production of the target compound(s). In particular embodiments, two or more target compounds are recovered from a culture.

The term "fermentation run" refers to one complete cycle of a batch, semi-continuous or continuous fermentation. A fermentation run preferably begins when the fermentor is initially filled with starting materials and is inoculated with the proper organisms. A fermentation run preferably ends when the fermentor organisms are no longer active, or when the fermentor is emptied.

The term "inoculation" refers to the placement of host cells (e.g., genetically modified microbial cells) that will grow to form the microbial culture placed in a culture medium, such as a fermentation tank comprising media to be fermented.

The term "single inoculum" refers to the material used in an inoculation, for example, a composition comprising host cells (e.g., genetically modified microbial cells) placed in a culture medium, such as a fermentation tank comprising media, at an initial time point to grow biomass.

The term "co-production" refers to producing two or more target compounds from a single inoculum, i.e., from cells produced from a single host cell. As used herein, the term, co-production can refer to concurrent or simultaneous production of two or more compounds in a single fermentation run in a fermentor. The term, co-production, can also refer to a sequential production of two or more target compounds from a single inoculum, wherein at least one target compound produced by activating expression of enzymes of a biosynthetic pathway for the target compound in a first fermentation run, followed by activating expression of enzymes of another biosynthetic pathway for another target compound. In certain embodiments, a sequential production can be achieved in two separate fermentation runs.

As used herein, the term "carotenoid" refers to a class of hydrocarbons having a conjugated polyene carbon skeleton formally derived from isoprene. This class of molecules is composed of triterpenes and tetraterpenes and their oxygenated derivatives; and, these molecules typically have strong light absorbing properties and impart color.

The term "carotenoid" may include both carotenes and xanthophylls. A "carotene" refers to a hydrocarbon carotenoid (e.g., β-carotene and lycopene). In contrast, the term "xanthophyll" refers to a C40 carotenoid that contains one or more oxygen atoms in the form of hydroxy-, methoxy-, oxo-, epoxy-, carboxy-, or aldehydic functional groups. Examples of xanthophylls include, but are not limited to antheraxanthin, adonixanthin, astaxanthin (i.e., 3,3"-dihydroxy-β,β-carotene-4,4"-dione), canthaxanthin (i.e., β,β-carotene-4,4"-dione), β-cryptoxanthin, keto-γ-carotene, echinenone, 3-hydroxyechinenone, 3'-hydroxyechinenone, zeaxanthin, adonirubin, tetrahydroxy-β,β'-caroten-4,4'-dione, tetrahydroxy-β,β'-caroten-4-one, caloxanthin, erythroxanthin, nostoxanthin, flexixanthin, 3-hydroxy-γ-carotene, 3-hydroxy-4-keto-γ-carotene, bacteriorubixanthin, bacteriorubixanthinal and lutein.

As used herein, "a first isoprenoid" and "a second isoprenoid" refer to target compounds which are produced by a host cell which is genetically modified with heterologous nucleic acids encoding a biosynthetic pathway to produce the first isoprenoid and the second isoprenoid. Target compounds are compounds intended to be recovered from the host cell. Generally, they are not intermediates on pathways to make the host compounds. Those of skill will recognize that target compounds may have common intermediates.

As used herein, the term "genetic switch" refers to one or more genetic elements that allows controlled expression enzymes that produce the first isoprenoid compound and enzymes that produce the second isoprenoid compound. In a first configuration, the genetic switch could promote expression of enzymes that produce the first isoprenoid compound and suppress enzymes that produce the second isoprenoid compound. In a second configuration, the genetic switch could suppress expression of enzymes that produce the first isoprenoid compound and promote enzymes that produce the second isoprenoid compound. In a third configuration, the genetic switch could promote expression of enzymes that produce the first isoprenoid compound and promote enzymes that produce the second isoprenoid compound. In a fourth configuration, the genetic switch could suppress expression of enzymes that produce the first isoprenoid compound and suppress enzymes that produce the second isoprenoid compound. For example, a genetic switch can include one or more promoters operably linked to one or more genes encoding a biosynthetic enzyme or one or more promoters operably linked to a transcriptional regulator which regulates expression one or more biosynthetic enzymes.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus. The term "heterologous enzyme" refers to an enzyme that is not normally found in a given cell in nature. The term encompasses an enzyme that is: (a) exogenous to a given cell (i.e., encoded by a nucleotide sequence that is not naturally present in the host cell or not naturally present in a given context in the host cell); and (b) naturally found in the host cell (e.g., the enzyme is encoded by a nucleotide sequence that is endogenous to the cell) but that is produced in an unnatural amount (e.g., greater or lesser than that naturally found) in the host cell.

On the other hand, the term "native" or "endogenous" as used herein with reference to molecules, and in particular enzymes and nucleic acids, indicates molecules that are expressed in the organism in which they originated or are found in nature, independently of the level of expression that can be lower, equal, or higher than the level of expression of the molecule in the native microorganism. It is understood that expression of native enzymes or polynucleotides may be modified in recombinant microorganisms.

As used herein, the term "production" generally refers to an amount of isoprenoid or produced by a genetically modified host cell provided herein. In some embodiments, production is expressed as a yield of isoprenoid by the host cell. In other embodiments, production is expressed as a productivity of the host cell in producing the isoprenoid.

As used herein, the term "productivity" refers to production of an isoprenoid by a host cell, expressed as the amount of isoprenoid produced (by weight) per amount of fermentation broth in which the host cell is cultured (by volume) over time (per hour).

As used herein, the term "yield" refers to production of an isoprenoid by a host cell, expressed as the amount of isoprenoid produced per amount of carbon source consumed by the host cell, by weight.

As used herein, the term "variant" refers to a polypeptide differing from a specifically recited "reference" polypeptide (e.g., a wild-type sequence) by amino acid insertions, deletions, mutations, and substitutions, but retains an activity that is substantially similar to the reference polypeptide. In some embodiments, the variant is created by recombinant DNA techniques, such as mutagenesis. In some embodiments, a variant polypeptide differs from its reference polypeptide by the substitution of one basic residue for another (i.e. Arg for Lys), the substitution of one hydrophobic residue for another (i.e. Leu for Ile), or the substitution of one aromatic residue for another (i.e. Phe for Tyr), etc. In some embodiments, variants include analogs wherein conservative substitutions resulting in a substantial structural analogy of the reference sequence are obtained. Examples of such conservative substitutions, without limitation, include glutamic acid for aspartic acid and vice-versa; glutamine for asparagine and vice-versa; serine for threonine and vice-versa; lysine for arginine and vice-versa; or any of isoleucine, valine or leucine for each other.

As used herein, the term "sequence identity" or "percent identity," in the context or two or more nucleic acid or protein sequences, refer to two or more sequences or subsequences that are the same or have a specified percentage of amino acid residues or nucleotides that are the same. For example, the sequence can have a percent identity of at least 60%, at least 65%, at least 70%, at least 75%, at least 80%, at least 85%, at least 90%, at least 91% at least 92%, at least 93%, at least 94%, at least 95%, at least 96%, at least 97%, at least 98%, at least 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer program and mathematical algorithms known in the art. Such algorithms that calculate percent sequence identity generally account for sequence gaps and mismatches over the comparison region. Programs that compare and align sequences, like Clustal W (Thompson et al., (1994) Nucleic Acids Res., 22: 4673-4680), ALIGN (Myers et al., (1988) CABIOS, 4: 11-17), FASTA (Pearson et al., (1988) PNAS, 85:2444-2448; Pearson (1990), Methods Enzymol., 183: 63-98) and gapped BLAST (Altschul et al., (1997) Nucleic Acids Res., 25: 3389-3402) are useful for this purpose. The BLAST or BLAST 2.0 (Altschul et al., J. Mol. Biol. 215:403-10, 1990) is available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=1, Nucleic mismatch=−3, Expectation value=10.0, Word size=11). For polypeptide sequence alignment and sequence identity calculations, BLASTP program is used with its default parameters (Alignment matrix=BLOSUM62; Gap costs: Existence=11, Extension=1; Compositional adjustments=Conditional compositional score, matrix adjustment; Expectation value=10.0; Word size=6; Max matches in a query range=0). Alternatively, the following program and parameters are used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

5.2 Description

Provided herein are methods and host cells for co-production of two or more isoprenoids in a culture medium. The host cells comprise one or more enzymes in a first biosynthetic pathway to produce a first isoprenoid. The host cells further comprise one or more heterologous nucleic acid encoding one or more enzymes in a second biosynthetic pathway to produce a second isoprenoid. In the methods, the first isoprenoid is recovered, and the second isoprenoid is recovered.

Carotenoids are red, yellow, and orange pigments that are widely distributed in nature. C40 carotenoids belong to the category of tetraterpenes (i.e., they have 40 carbon atoms, being built from four terpene units each containing 10 carbon atoms). There are two general classes of carotenoids: carotenes and xanthophylls. Carotenes consist only of carbon and hydrogen atoms. Xanthopylls have one or more oxygen atoms. Hydrocarbon carotenoids are classified as carotenes while those containing oxygen are known as xanthopylls. Astaxanthin is an oxidized carotenoid known as a xanthophyll or ketocarotenoid (i.e., a carotenoid with a ketone group).

Figure 1A:
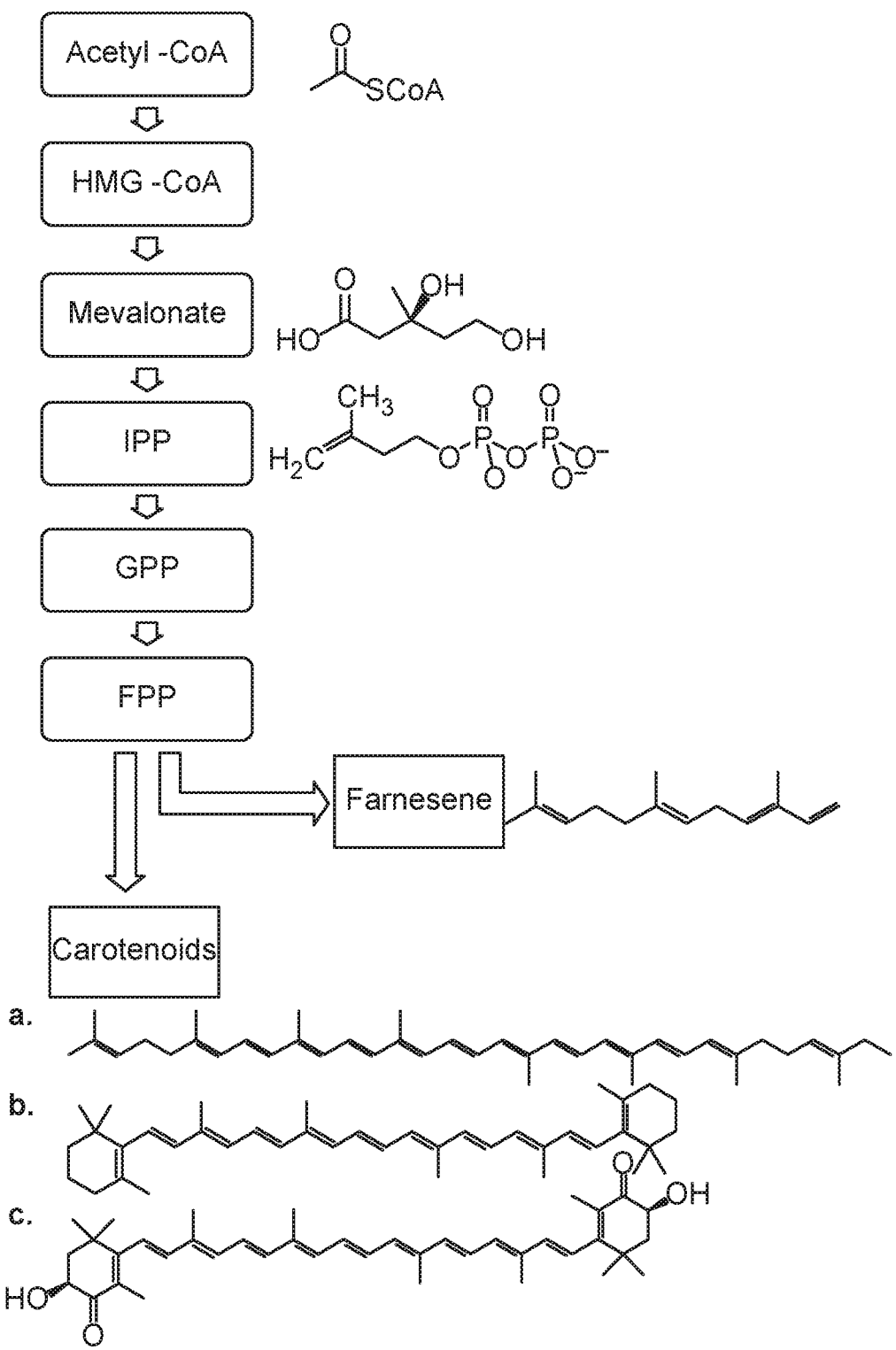
FIG. 1A illustrates an overview of an abbreviated mevalonate pathway and a split of carbon flow for farnesene and carotenoid biosynthesis. Structures of 3 carotenoids are shown: (a) lycopene, (b) β-carotene, and (c) astaxanthin.
Figure 1B:
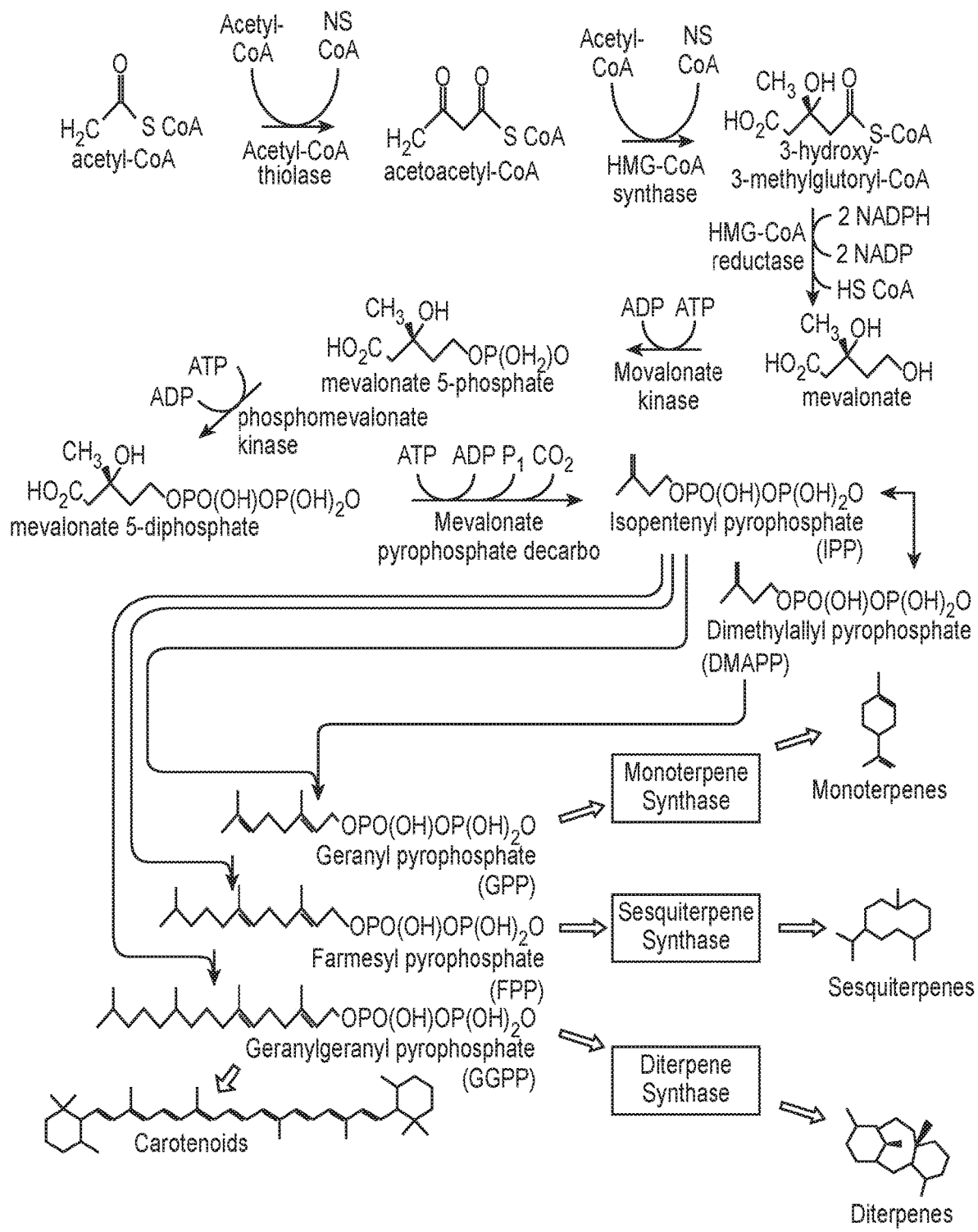
FIG. 1B illustrates the mevalonate pathway and production of isoprenoids of various carbon numbers.

Farnesene (or other sesquiterpenes) and all carotenoids, including astaxanthin, are isoprenoids that can be produced in yeast via the mevalonate pathway. The split of carbon flux to farnesene or to carotenoids (including astaxanthin), is shown diagrammatically in FIG. 1A. Abbreviations used in FIG. 1A includes HMG-CoA (3-Hydroxy 3-MethylGlutaryl Coenzyme A), IPP (isopentenyl diphosphate), GPP (geranyl diphosphate), and FPP (farnesyl diphosphate). The arrows in FIG. 1A represent enzymatic conversions, and may be catalyzed by a single enzyme or more than one enzyme. FIG. 1A includes an abbreviated version of the mevalonate pathway, and the complete mevalonate pathway and production of other terpenes are illustrated in FIG. 1B. The enzymes of the mevalonate pathway (from acetyl-CoA to IPP) are further described in Section 5.5. While FIGS. 1A and 1B illustrate the mevalonate pathway to produce isoprenoid precursors such as IPP, the DXP pathway can be used to produce isoprenoid precursors.

The over-expression of the mevalonate pathway in yeast (*Saccharomyces cerevisiae*) has been described in the scientific literature (e.g., Notman et al., *J. Am. Chem. Soc.*, 128, 2006, 13982-13983; He et al., *Mol. Membr. Biol.* 3-4, 2012, 107-113). In certain embodiments, one or more enzymes of the mevalonate pathway are over-expressed as previously described.

Production of β-carotene in engineered *S. cerevisiae* has been described. Kim et al., *Food Sci. Biotechnol.* 19, 2010, 263-266. The β-carotene biosynthetic pathway is reproduced as FIG. 2. As illustrated in the exemplary β-carotene biosynthetic pathway shown in FIG. 2, after IPP is formed from the mevalonate pathway, it can be converted into dimethylallyl pyrophosphate (DMAPP) by an IPP isomerase. IPP and DMAPP are condensed by geranyl pyrophosphate synthase (GPPS) to produce geranyl pyrophosphate (GPP). GPP and IPP can be combined by farnesyl pyrophosphate synthase (FPPS) to produce farnesyl pyrophosphate (FPP). FPP and IPP can be combined by a geranyl pyrophosphate synthase (GGPP synthase) to produce GGPP. Exemplary nucleic acids that encode GGPP synthases include BTS1 gene (*S. cerevisiae*) and CrtE gene (*X. dendrohous*). GGPP and GGPP can be combined by phytoene synthase (encoded by CrtB) to produce phytoene. In the exemplary β-carotene biosynthetic pathway shown in FIG. 2, a bifunctional enzyme (phytoene synthase/lycopene cyclase) encoded by CrtYB is shown for this enzymatic reaction step. Phytoene can be converted to neurosporene by the enzymatic action of a phytoene desaturase which can be encoded by CrtI gene. Neurosporene can be converted to 7,8-dihydro-β-carotene by the enzymatic action of lycopene cyclase (encoded by CrtY gene) or a bifunctional enzyme (encoded by CrtYB gene). Neurosporene can also be converted to lycopene by the enzymatic action of a phytoene desaturase (encoded by CrtI gene). Lycopene can be converted to β-carotene by the enzymatic action of a lycopene cyclase (encoded by CrtB gene). In the exemplary β-carotene biosynthetic pathway shown in FIG. 2, a bifunctional enzyme (phytoene synthase/lycopene cyclase) encoded by CrtYB gene is shown for this enzymatic reaction step. It is noted that phytoene shown in FIG. 2 does not impart any color, and therefore is not considered a carotenoid, whereas neurosporene, lycopene, β-carotene, and 7,8-dihyro-β-carotene are considered as carotenoids.

Figure 3A:
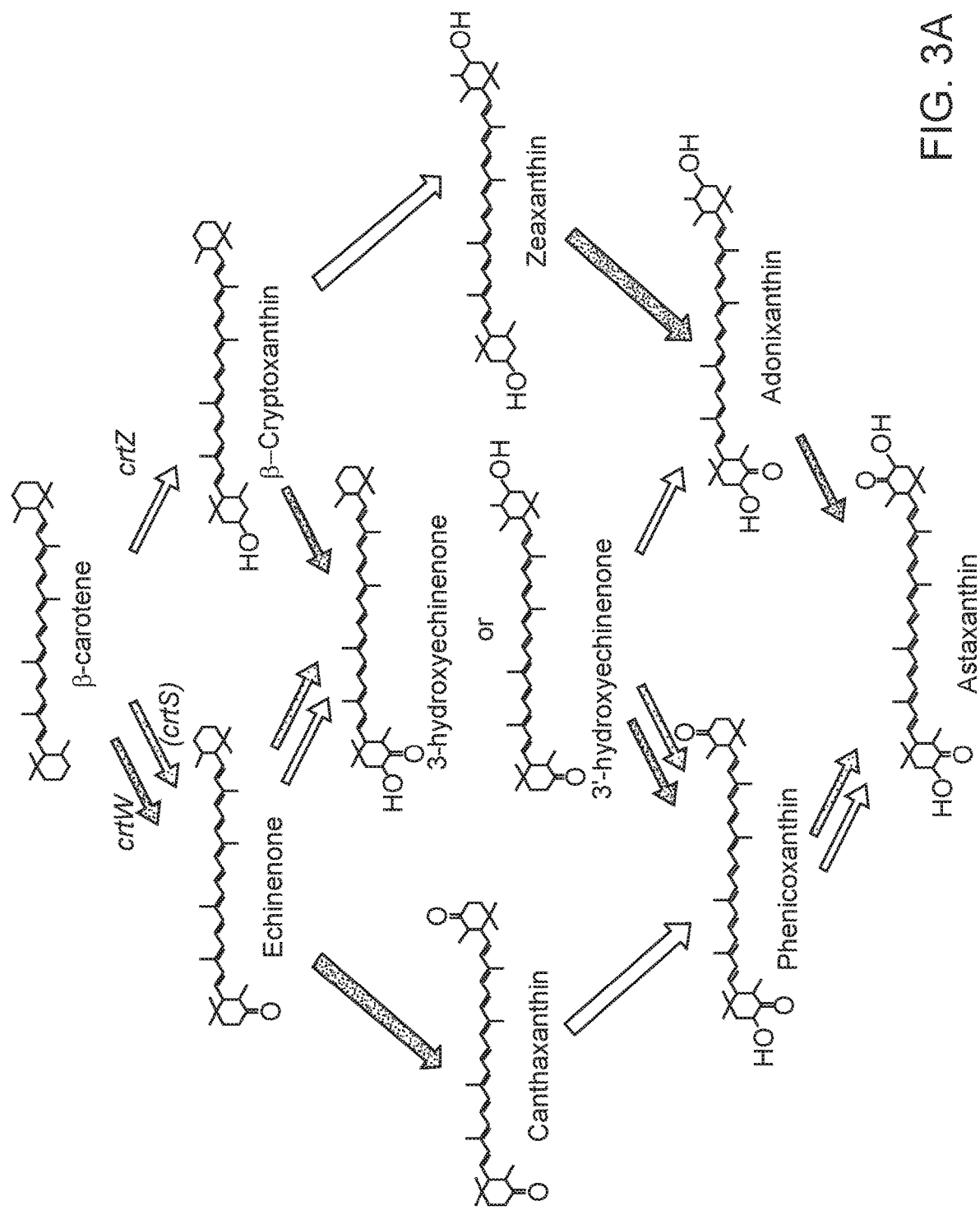
FIG. 3A illustrates the pathway engineered for astaxanthin biosynthesis in *S. cerevisiae* using genes from *X. dendrorhous*.

The production of astaxanthin starting from beta-carotene is shown in FIG. 3A. FIG. 3A illustrates an exemplary biosynthetic pathway for astaxanthin starting from β-carotene. The black, white, and gray thick arrows indicate the reactions catalyzed by the enzymes encoded by crtW, crtZ, and crtS, respectively. See Ukibe et al., *Applied and Environ. Microbiol.* November 2009, p. 7025-7211. Beta-carotene is converted to astaxanthin in four steps in which two keto and hydroxyl groups are added to each ring by beta-carotene ketolase encoded by crtW and beta-carotene hydroxylase encoded by crtZ, respectively. As shown in FIG. 3A, a single *X. dendrorhous* gene, CrtYB, encodes a bifunctional enzyme phytoene synthase/lycopene cyclase. See Verdoes et al., 1999, *Mol. Gen. Genet.* 262:453-461. CrtS encodes astaxanthin synthase, catalysing ketolation and hydroxylation of beta-carotene. It is believed that crtS is presumed to encode a cytochrome p450 protein. Ojima et al. (2006) *Mol. Genet. Genomics* 275: 148-158. It is believed that the introduction of crtR, encoding the cytochrome p450 reductase, is important for the functional expression of CrtS and astaxanthin production in host cells such as *S. cerevisiae*. See Ukibe et al., *Applied and Environ. Microbiol.* November 2009, p. 7025-7211.

Figure 3B:
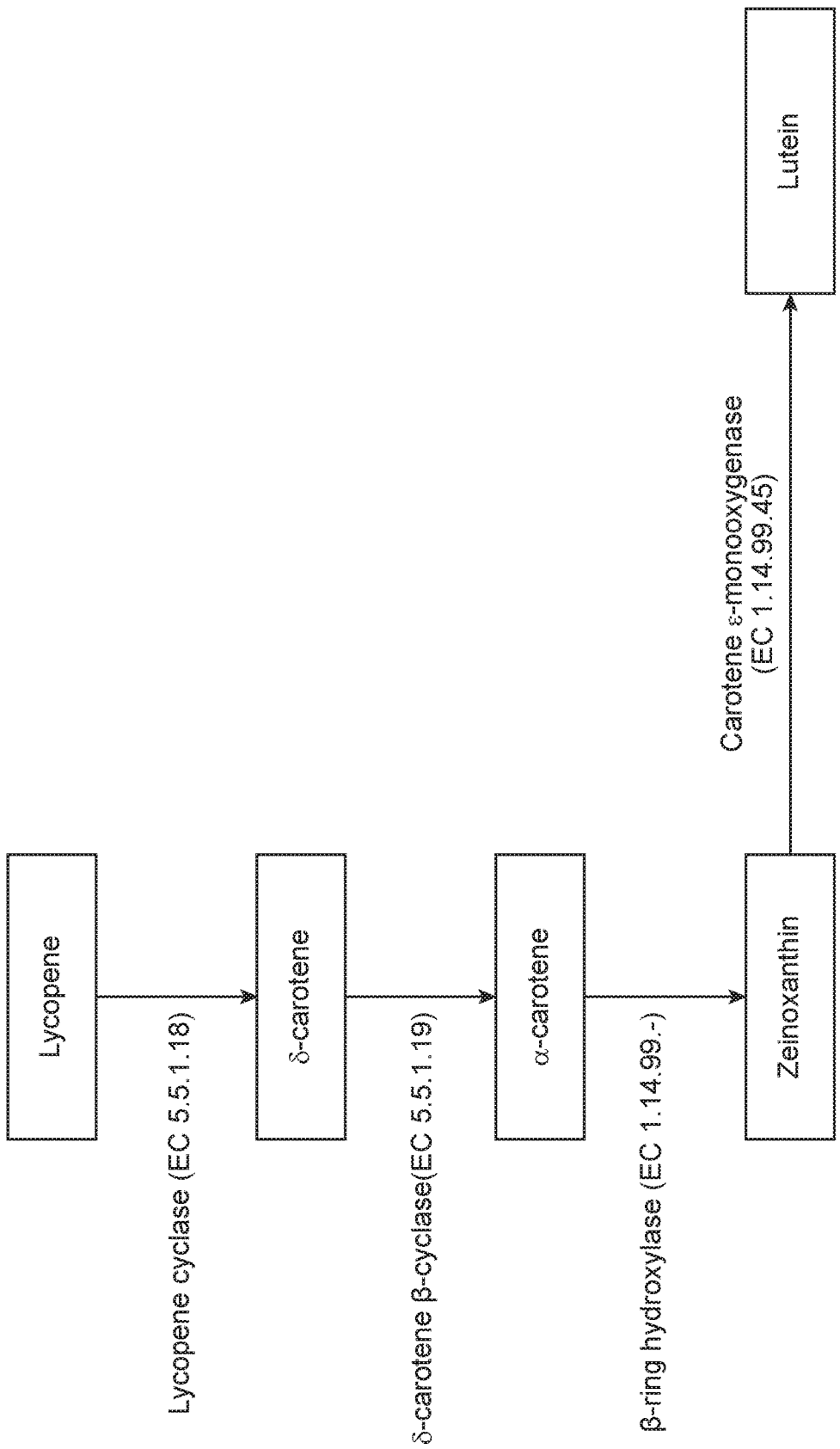
FIG. 3B illustrates an exemplary pathway for production of lutein and other carotenoids.

FIG. 3B illustrates another exemplary biosynthetic pathway for production of carotenoids. In particular, FIG. 3B illustrates production of lutein from lycopene. Lycopene can be converted to δ-carotene by a lycopene cyclase (EC 5.5.1.18). δ-carotene can be converted α-carotene by δ-carotene β-cyclase (EC 5.5.1.19). α-carotene can be converted to zeinoxanthin by β-ring hydroxylase (EC 1.14.99.-). Zeinoxanthin can be converted to lutein by carotene ε-monooxygenase (EC 1.14.99.45). Examples of these enzymes are CitHYb, CitCYP97A, CitCYP97B, and CitCYP97C from citrus fruits (Ma et al. 2016, *BMC Plant Biology* 16:148) In certain embodiments, any suitable nucleic acid(s) encoding enzymes in the lutein biosynthetic pathway can be used in producing genetically modified host cells or methods for co-production of lutein with another isoprenoid.

In certain embodiments, any suitable nucleic acid(s) encoding enzymes in the β-carotene/astaxanthin biosynthetic pathway can be used in producing genetically modified host cells or methods for co-production of one or more carotenoids with another isoprenoid. The exemplary nucleic acids encoding such enzymes useful in present embodiments are shown in Table 1 below. Additional nucleic acids useful in the production of beta-carotene/astaxanthin pathways are further described in Section 5.6 below.

during the first time period, followed by separation of host cells and production of the engineered carotenoid during a second period of incubation of the host cells. Co-production by fermentation has been described previously for 1,4-butanediol and gamma-butyrolactone (U.S. Pat. No. 9,222,113), and also co-production of a terpene and various named products (US 2015/0211024), but there are no known examples of co-production of isoprenoids, such as sesquiterpenes and carotenoids.

5.3 Host Cells

Provided herein are host cells capable of co-producing two or more isoprenoids. In certain embodiments, the host cell is genetically modified with one or more heterologous nucleic acids encoding one or more enzymes in a first biosynthetic pathway to produce a first isoprenoid and one or more heterologous nucleic acids encoding one or more enzymes in a second biosynthetic pathway to produce a second isoprenoid, which has a molecular weight that is

TABLE 1

Figure 2:
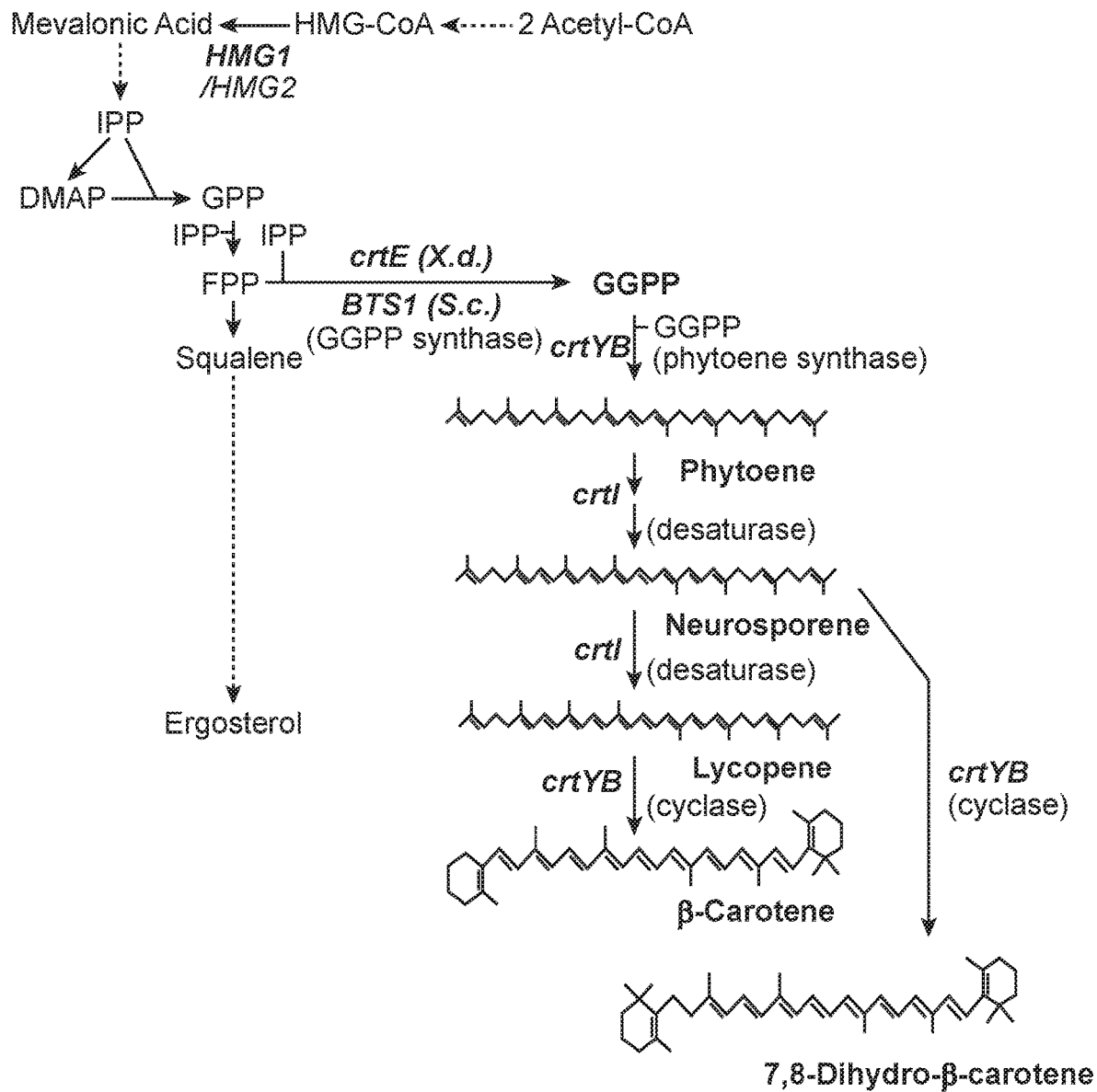
FIG. 2 illustrates the production pathway of β-carotene in the carotogenic yeast, *Xanthophyllomyces dendrorhus*, also showing GGPS from *Saccharomyces cerevisiae* encoded by BTS1.

List of nucleic acids and encoded enzymes suitable for enzymatic reactions shown in FIGS. 2 and 3A

| Gene Name | Enzyme Activity | Organism | GenBank ID | UniProt | Reference |
|---|---|---|---|---|---|
| CrtYB | Phytoene synthase/ Lycopene cyclase | *Xanthophyllomyces dendrorhous* | | | Verwaal et al. *App. Environ. Microbiol.* 73(13): 4342-50 (2007) |
| CrtI | Phytoene desaturase | *Xanthophyllomyces dendrorhous* | | | Verwaal et al (2007) |
| CrtS | astaxanthin Cytochrome-P450 Hydroxylase/ ketolase | *Xanthophyllomyces dendrorhous* | AAY20975.1 | Q3HR17_PHARH | |
| CrtR | Cytochrome-P450 Reductase | *Xanthophyllomyces dendrorhous* | AIP94032.1 | A0A0C4MWF8_PHARH | |
| CrtW | β-Carotene Ketolase | *Paracoccus* sp. Strain N81106 (*Agrobacterium aurantiacum*) | BAE47465.1 | CRTW_PARSN | Ukibe et al, *Appl. Environ. Microbiol.* 75(22): 7205-7211 (2009) |
| CrtZ | β-Carotene Hydroxylase | *Paracoccus* sp. Strain N81106 (*Agrobacterium aurantiacum*) | BAE47466.1 | CRTZ_PARSN | |
| CrtZ | β-Carotene Hydroxylase | *Pantoea ananatis* | ADD79330.1 | D4GFL0_PANAM | Ukibe et ai. (2009) |
| HpBkt | β-Carotene Ketolase | *Haematococcus pluvialis* | D45881.1 | GenBank: BAA08300.1 | |
| HpCrtZ | β-Carotene Hydroxylase | *Haematococcus pluvialis* | KP866868.1 | GenBank: AKQ20654.1 | |

As described above, production of carotenoids in genetically modified microorganisms were previously reported. For example, astaxanthin has been produced by engineering of the oleaginous yeast, *Yarrowia lipolytica* (U.S. Pat. No. 7,851,199). Embodiments of the present invention differ from these previous studies in that in present embodiments, one host cell (e.g., yeast cell) can co-produce two different isoprenoids (that are substantially different in molecular weight) during a single fermentation run after inoculation or in two fermentation runs after inoculation. For example, the two products, farnesene and a carotenoid or mixture of carotenoids (e.g., as defined in U.S. Pat. No. 7,851,199) such as astaxanthin, may be co-produced simultaneously (embodiment 1 of FIG. 4), or may be produced sequentially (embodiment 2 of FIG. 4), with farnesene being produced different from the first isoprenoid. In certain embodiments, the host cell is genetically modified with one or more heterologous nucleic acids encoding one or more enzymes in a third biosynthetic pathway to produce a third isoprenoid. In certain embodiments, the host cell is genetically modified with one or more heterologous nucleic acids encoding one or more enzymes in a fourth biosynthetic pathway to produce a fourth isoprenoid. In certain embodiments, the host cell is similarly modified to produce a fifth, sixth, seventh, eighth, ninth or tenth isoprenoid, or more.

In certain embodiments, the first isoprenoid is not an endogenous compound produced by a parent host cell which is not genetically modified. In certain embodiments, the second isoprenoid is not an endogenous compound produced by a parent host cell which is not genetically modified. In certain embodiments, when the host cell is similarly modified to produce a third, fourth, fifth, sixth, seventh, eighth, ninth, or tenth isoprenoid, or more, these additional isoprenoids are not endogenously produced by the parent host cell.

In certain embodiments, the host cell is not genetically modified with to produce a target compound for recovery other than a compound derived from IPP. In these embodiments, the host cell is modified to only produce the isoprenoid target compounds. These are the compounds that are intended to be, or are, recovered from a culture of the host cell. The host cells are not modified to produce other compounds for recovery.

In certain embodiments, first isoprenoid is a C5, C10, C15, or C20 isoprenoid, and the second isoprenoid is a C30, C35, C40 or higher carbon isoprenoid. In certain embodiments, the first isoprenoid is a C15 isoprenoid and the second isoprenoid is a C40 isoprenoid. In certain embodiments, the first isoprenoid is a sesquiterpene, and the second isoprenoid is a tetraterpene. In particular embodiments, the first isoprenoid is farnesene, and the second isoprenoid is a carotenoid. In certain embodiments, the first isoprenoid is β-farnesene and the second carotenoid is a C40 carotenoid. In certain embodiments, the second isoprenoid is a carotenoid or a mixture of carotenoids. In certain embodiments, the second isoprenoid is astaxanthin, xanthophyll, or ketocarotenoid. In certain embodiments, the second isoprenoid is astaxanthin, canthaxanthin, zeaxanthin, beta-carotene, lycopene, lutein, or any combination thereof. In certain embodiments, any combination of first isoprenoid and second isoprenoid, or any additional isoprenoids described herein can be selected for production as target compounds from genetically modified host cell.

While not intending to be bound by any particular theory of operation, during the course of isoprenoid co-production, it was discovered that co-production of one or more second isoprenoids (e.g., carotenoids) with a first isoprenoid (e.g., farnesene) can reduce the biomass yield (e.g., cell density) and the first isoprenoid production amount, compared to a parent host cell which is genetically modified to produce only the first isoprenoid. Such results were observed with host cells which are genetically modified to provide a relatively high carbon flux towards the carotenoid production. Without wishing to be bound by a theory, it is believed that a relatively high production of carotenoids or intermediates towards carotenoids (e.g., GGPP) may be toxic to host cells or may slow down the cell growth. It was further discovered by the present inventors that the negative impact on the accumulation of biomass by the co-production of carotenoid with a first isoprenoid as target compounds can be overcome by adjusting the carbon flux towards production of carotenoids relative to the carbon flux towards production of the first isoprenoid.

Thus, in certain embodiments, provided herein are host cells that are genetically modified such that co-production of a second isoprenoid does not substantially affect the production of a first isoprenoid or the biomass yield during co-production. In these embodiments, a host cell can be first genetically modified by introducing a heterologous nucleic acid encoding a terpene synthase to produce a first isoprenoid at a desired target amount. After building a parent host cell capable of producing the first isoprenoid at a target amount, the parent host cell can be further genetically modified by introducing a heterologous nucleic acid encoding a terpene synthase to produce a second isoprenoid at a level that does not substantially affect the production of the first isoprenoid production or the biomass yield during co-production. As described in the Example section, when the carbon flux towards the production of the second isoprenoid (e.g., one or more carotenoids) is reduced compared to the carbon flux towards the first isoprenoid (e.g., a sesquiterpene), the co-production of the second isoprenoid does not substantially impact the first isoprenoid production amount or the biomass yield. In some embodiments, the relative ratio of the two isoprenoids can be adjusted between about 0.001% to about 2% by weight.

Thus, in certain embodiments, the host cell is genetically modified such that it is capable of co-producing a second isoprenoid and a first isoprenoid at a ratio of between about 0.001% and about 2% by weight. In certain embodiments, the method for co-production of isoprenoids comprises producing a second isoprenoid and a first isoprenoid at a ratio of between about 0.001% and about 1% by weight. In certain embodiments, the method for co-production of isoprenoids comprises producing a second isoprenoid and a first isoprenoid at a ratio of between about 0.1% and about 1% by weight. In particular embodiments, the ratio is based on weight %. In particular embodiments, the ratio is based on mass of the compounds per volume of media. In particular embodiments, the ratio is based on mass of the compounds per mass of dry cell weight.

In certain embodiments, the host cell is genetically modified such that it is capable of co-producing the first isoprenoid at an amount of about 2.5 g/L to about 200 g/L. In certain embodiments, the host cell is genetically modified such that it is capable of co-producing the second isoprenoid at an amount of about 1 mg/L to about 4000 mg/L. In certain embodiments, the host cell is genetically modified such that it is capable of co-producing the first isoprenoid in an amount of about 30 g/L to about 170 g/L, about 50 g/L to about 160 g/L, or any number in between these ranges. In certain embodiments, the host cell is genetically modified such that it is capable of co-producing the second isoprenoid at an amount of about 1 mg/L to about 3000 mg/L, about 1 mg/L to about 2000 mg/L, about 1 mg/L to about 1000 mg/L, about 1 mg/L to about 800 mg/L, about 1 mg/L to about 500 mg/L, about 1 mg/L to about 400 mg/L, about 1 mg/L to about 300 mg/L, or any number in between these ranges. In certain embodiments, the host cell is genetically modified such that it is capable of co-producing the first isoprenoid at an amount of about 2.5 g/L to about 200 g/L and the second isoprenoid at an amount of about 1 mg/L to about 4000 mg/L. In certain embodiments, the host cell is genetically modified such that it is capable of co-producing the first isoprenoid in an amount of about 2.5 g/L to about 200 g/L and the second isoprenoid in an amount of about 1 mg/L to about 500 mg/L. In certain embodiments, the host cell is genetically modified such that it is capable of co-producing the first isoprenoid at an amount of about 100 g/L to about 120 g/L. In certain embodiments, the host cell is genetically modified such that it is capable of co-producing the second isoprenoid at an amount of about 20 mg/L to about 1250 mg/L. In certain embodiments, the host cell is genetically modified such that it is capable of co-producing the first isoprenoid at an amount of about 100 g/L to about 120 g/L and the second isoprenoid at an amount of about 20 mg/L to about 1250 mg/L. In certain embodiments, the host cell is genetically modified such that it is capable of co-producing the second isoprenoid at an amount of about 75 mg/L. In certain embodiments, the host cell is genetically modified such that it is capable of co-producing the first isoprenoid at an amount of about 100 g/L to about 120 g/L and the second isoprenoid at an amount of about 75 mg/L. In certain embodiments, the host cells genetically modified such that it is capable of co-producing any combination amounts of the first isoprenoid and the second isoprenoid described herein.

In certain embodiments, the host cell is genetically modified such that it is capable of co-producing the first isoprenoid at an amount of about 100 g to 5 kg per kg of dry cell mass. In certain embodiments, the host cell is genetically modified such that it is capable of co-producing the second isoprenoid at an amount of about 1 mg to about 100 g per kg of dry cell mass. In certain embodiments, the host cell is genetically modified such that it is capable of co-producing the first isoprenoid at an amount of about 100 g to 5 kg per kg of dry cell mass and the second isoprenoid at an amount of about 1 mg to about 50 g per kg of dry cell mass. In certain embodiments, the host cell is genetically modified such that it is capable of co-producing the first isoprenoid at an amount of about 100 g to 5 kg per kg of dry cell mass and the second isoprenoid at an amount of about 1 mg to about 40 g per kg of dry cell mass. In certain embodiments, the host cell is genetically modified such that it is capable of co-producing the first isoprenoid at an amount of about 100 g to 5 kg per kg of dry cell mass and the second isoprenoid at an amount of about 1 mg to about 30 g per kg of dry cell mass. In certain embodiments, the host cell is genetically modified such that it is capable of co-producing the first isoprenoid at an amount of about 100 g to 5 kg per kg of dry cell mass and the second isoprenoid at an amount of about 1 mg to about 20 g per kg of dry cell mass. In certain embodiments, the host cell is genetically modified such that it is capable of co-producing the first isoprenoid at an amount of about 100 g to 5 kg per kg of dry cell mass and the second isoprenoid at an amount of about 3 g per kg of dry cell mass. In certain embodiments, the host cell is genetically modified such that it is capable of co-producing the first isoprenoid and the second isoprenoid in any combination of ranges described herein.

The first isoprenoid can be any isoprenoid known to those of skill. In particular embodiments, the first isoprenoid is a C15 isoprenoid. In certain embodiments, the first isoprenoid is selected from the group consisting of farnesene, farnesol, farnesyl diphosphate, nerolidol, bisabolene, bisabolol, capsidiol, and patchoulol. In particular embodiments, the first isoprenoid is farnesene.

In certain embodiments, the first isoprenoid is a sesquiterpene and the second isoprenoid is one or more carotenoids. In certain embodiments, the first isoprenoid is a sesquiterpene and the second isoprenoid is one or more C40 carotenoids. In certain embodiments, the first isoprenoid is a sesquiterpene and the second isoprenoid is one or more of astaxanthin, canthaxanthin, zeaxanthin, beta-carotene, lycopene, and lutein. In certain embodiments, the first isoprenoid is farnesene, and the second isoprenoid is one or more of astaxanthin, canthaxanthin, zeaxanthin, beta-carotene, lycopene, and lutein. In certain embodiments, the ratio of the second isoprenoid in relation to the first isoprenoid is based on the weight of a single carotenoid. In certain embodiments, the ratio of the second isoprenoid in relation to the first isoprenoid is based on the weight of the combination of carotenoids produced by the host cell. In these embodiments, the weight ratio of the first isoprenoid and the second isoprenoid are measured based on the dry cell weight from which the first isoprenoid and the second isoprenoids are produced.

In certain embodiments, the first isoprenoid is predominantly released from the host cell into the culture medium. In particular embodiments, the first isoprenoid is of a size or composition that enables its release from the cell. This can be predicted in advance or determined empirically. In particular embodiments, when the host cells are separated from the culture medium, at least 70%, 75%, 80%, 85%, 90%, or 95% of the first isoprenoid is found in the culture medium.

In certain embodiments, the second isoprenoid is predominantly associated with the host cell. In certain embodiments, the second isoprenoid is predominantly retained within the host cell. In particular embodiments, the second isoprenoid is of a size or composition that reduces or prevents its release from the cell. This can be predicted in advance or determined empirically. In particular embodiments, when the host cells are separated from the culture medium, at least 70%, 75%, 80%, 85%, 90%, or 95% of the second isoprenoid is found with the cell mass.

In certain embodiments, the host cell is capable of producing the first isoprenoid during co-production with the second isoprenoid in an amount of at least about 85%, 90%, 95%, 96%, 97%, 98%, or 99% of the amount of the first isoprenoid produced by a parent cell which is genetically modified to produce the first isoprenoid but not the second isoprenoid.

In certain embodiments, a cell density (or biomass yield) of the host cell during co-production of the first isoprenoid and the second isoprenoid is at least about 85%, 90%, 95%, 96%, 98%, or 99% of a cell density of a parent cell which is genetically modified to produce the first isoprenoid but not the second isoprenoid.

In certain embodiments, the host cell is genetically modified to produce two isoprenoids as target compounds, and is not genetically modified to produce a target compound which is not derived from IPP. In certain embodiments, the host cell is genetically modified to produce a sesquiterpene and one or more C40 carotenoids, and is not genetically modified to produce another target molecule which is not derived from IPP. In certain embodiments, the host cell is genetically modified to produce a C10, C15, or C20 isoprenoid as the first isoprenoid and one or more C40 carotenoids as a second isoprenoid, and is not genetically modified to produce another target molecule which is not derived from IPP. Genetically modifying a target molecule other than isoprenoids derived from IPP can divert the carbon flux away from IPP, therefore, reducing the carbon flux towards the production of isoprenoids as target compounds.

In certain embodiments, the host cell is further genetically modified to comprise: (a) a heterologous nucleic acid encoding a first polyprenyl synthase and a heterologous nucleic acid for encoding a first terpene synthase for the production of the first isoprenoid; and (b) a nucleic acid encoding a second polyprenyl synthase and a heterologous nucleic acid encoding a second terpene synthase for the production of the second isoprenoid.

In certain embodiments, the host cell is further genetically modified to comprise: (a) a heterologous nucleic acid encoding a FPP synthase and a sesquiterpene synthase to produce a sesquiterpene as the first isoprenoid; and (b) a heterologous nucleic acid encoding a GGPP synthase and a carotenoid synthase to produce a carotenoid.

In certain embodiments, the genetically modified host cell is genetically modified to overexpress one or more enzymes of the mevalonate pathway. In certain embodiments, the genetically modified host cell is genetically modified to overexpress, all of the enzymes of the mevalonate pathway.

In certain embodiments, the genetically modified host cell further comprises a heterologous nucleic acid encoding a polyprenyl synthase for producing a polyprenyl diphosphate. In certain embodiments, the genetically modified host cell further comprises a heterologous nucleic acid encoding a FPP synthase. In certain embodiments, the genetically modified host cell further comprises a heterologous nucleic acid encoding a GGPP synthase. In certain embodiments, the genetically modified host cell further comprises a heterologous nucleic acid encoding a FPP synthase and comprises an endogenous nucleic acid encoding a GGPP synthase but does not comprise a heterologous nucleic acid encoding a GGPP synthase.

Any combination of heterologous nucleic acids described herein can be introduced into the host cell depending on which carotenoid is desired for co-production with a first isoprenoid.

In certain embodiments, the second isoprenoid is lycopene, and the host cell comprises a heterologous nucleic acid encoding a phytoene synthase; and a heterologous nucleic acid encoding a phytoene desaturase.

In certain embodiments, the second isoprenoid is β-carotene, and the host cell comprises: (i) a heterologous nucleic acid encoding a phytoene synthase; and (ii) a heterologous nucleic acid encoding a lycopene cyclase or (iii) a heterologous nucleic acid encoding a bifunctional enzyme having phytoene synthase and lycopene cyclase activities; and a heterologous nucleic acid encoding a phytoene desaturase.

In certain embodiments, the second isoprenoid is cantaxanthin, and the host cell comprises (i) a heterologous nucleic acid encoding a phytoene synthase; and (ii) a heterologous nucleic acid encoding a lycopene cyclase or (iii) a heterologous nucleic acid encoding a bifunctional enzyme having phytoene synthase and lycopene cyclase activities; a heterologous nucleic acid encoding a phytoene desaturase; and a heterologous nucleic acid encoding a β-carotene ketolase.

In certain embodiments, the second isoprenoid is zeaxanthin, and the host cell comprises: (i) a heterologous nucleic acid encoding a phytoene synthase; and (ii) a heterologous nucleic acid encoding a lycopene cyclase or (iii) a heterologous nucleic acid encoding a bifunctional enzyme having phytoene synthase and lycopene cyclase activities; a heterologous nucleic acid encoding a phytoene desaturase; and a heterologous nucleic acid encoding β-carotene hydroxylase.

In certain embodiments, the second isoprenoid is astaxanthin, and the host cell comprises: (i) a heterologous nucleic acid encoding a phytoene synthase; and (ii) a heterologous nucleic acid encoding a lycopene cyclase or (iii) a heterologous nucleic acid encoding a bifunctional enzyme having phytoene synthase and lycopene cyclase activities; a heterologous nucleic acid encoding a phytoene desaturase; (i) a heterologous nucleic acid encoding a β-carotene ketolase; and (ii) a heterologous nucleic acid encoding a β-carotene hydroxylase or (iii) a heterologous nucleic acid encoding a cytochrome p450 hydroxylase and ketolase capable of converting β-carotene to echinenone and to β-cryptoxanthin and subsequently to astaxanthin; and (iv) a heterologous nucleic acid encoding a cytochrome p450 reductase which interacts with the cytochrome p450 hydroxylase and ketolase.

In certain embodiments, the second isoprenoid is lutein, and the host cell comprises: a heterologous nucleic acid encoding a lycopene cyclase; a heterologous nucleic acid encoding a δ-carotene β-cyclase; a heterologous nucleic acid encoding β-ring hydroxylase; and a heterologous nucleic acid encoding a carotene ε-monooxygenase.

5.4 Cell Strains

The host cells can be any cells deemed useful by those of skill. Host cells useful in the compositions and methods provided herein include archae, prokaryotic, or eukaryotic cells.

Suitable prokaryotic hosts include, but are not limited, to any of a variety of gram-positive, gram-negative, or gram-variable bacteria. Examples include, but are not limited to, cells belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphylococcus, Strepromyces, Synnecoccus*, and *Zymomonas*. Examples of prokaryotic strains include, but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei*, and *Staphylococcus aureus*. In a particular embodiment, the host cell is an *Escherichia coli* cell.

Suitable archae hosts include, but are not limited to, cells belonging to the genera: *Aeropyrum, Archaeglobus, Halobacterium, Methanococcus, Methanobacterium, Pyrococcus, Sulfolobus*, and *Thermoplasma*. Examples of archae strains include, but are not limited to: *Archaeoglobus fulgidus, Halobacterium* sp., *Methanococcus jannaschii, Methanobacterium thermoautotrophicum, Thermoplasma acidophilum, Thermoplasma volcanium, Pyrococcus horikoshii, Pyrococcus abyssi*, and *Aeropyrum pernix*.

Suitable eukaryotic hosts include, but are not limited to, fungal cells, algal cells, insect cells, and plant cells. In some embodiments, yeasts useful in the present methods include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis*, and *Zygozyma*, among others.

In some embodiments, the host cell is *Saccharomyces cerevisiae, Pichia pastoris, Schizosaccharomyces pombe, Dekkera bruxellensis, Kluyveromyces lactis* (previously called *Saccharomyces lactis*), *Kluveromyces marxianus,*

*Arxula adeninivorans*, or *Hansenula polymorpha* (now known as *Pichia angusta*). In some embodiments, the host cell is a strain of the genus *Candida*, such as *Candida lipolytica, Candida guilliermondii, Candida krusei, Candida pseudotropicalis*, or *Candida utilis*.

In a particular embodiment, the host cell is *Saccharomyces cerevisiae*. In some embodiments, the host is a strain of *Saccharomyces cerevisiae* selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, CEN.PK, CEN.PK2, and AL-1. In some embodiments, the host cell is a strain of *Saccharomyces cerevisiae* selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the host cell is a microbe that is suitable for industrial fermentation. In particular embodiments, the microbe is conditioned to subsist under high solvent concentration, high temperature, expanded substrate utilization, nutrient limitation, osmotic stress due to sugar and salts, acidity, sulfite and bacterial contamination, or combinations thereof, which are recognized stress conditions of the industrial fermentation environment.

5.5 Mevalonate Pathway

In some embodiments, the cell provided herein comprises one or more enzymes of the mevalonate (MEV) pathway. In some embodiments, the one or more enzymes of the MEV pathway comprise an enzyme that condenses acetyl-CoA with malonyl-CoA to form acetoacetyl-CoA. In some embodiments, the one or more enzymes of the MEV pathway comprise an enzyme that condenses two molecules of acetyl-CoA to form acetoacetyl-CoA. In some embodiments, the one or more enzymes of the MEV pathway comprise an enzyme that condenses acetoacetyl-CoA with acetyl-CoA to form HMG-CoA. In some embodiments, the one or more enzymes of the MEV pathway comprise an enzyme that converts HMG-CoA to mevalonate. In some embodiments, the one or more enzymes of the MEV pathway comprise an enzyme that phosphorylates mevalonate to mevalonate 5-phosphate. In some embodiments, the one or more enzymes of the MEV pathway comprise an enzyme that converts mevalonate 5-phosphate to mevalonate 5-pyrophosphate. In some embodiments, the one or more enzymes of the MEV pathway comprise an enzyme that converts mevalonate 5-pyrophosphate to isopentenyl pyrophosphate.

In some embodiments, the one or more enzymes of the MEV pathway are selected from the group consisting of acetyl-CoA thiolase, acetoacetyl-CoA synthetase, HMG-CoA synthase, HMG-CoA reductase, mevalonate kinase, phosphomevalonate kinase and mevalonate pyrophosphate decarboxylase. In some embodiments, with regard to the enzyme of the MEV pathway capable of catalyzing the formation of acetoacetyl-CoA, the genetically modified host cell comprises either an enzyme that condenses two molecules of acetyl-CoA to form acetoacetyl-CoA, e.g., acetyl-CoA thiolase; or an enzyme that condenses acetyl-CoA with malonyl-CoA to form acetoacetyl-CoA, e.g., acetoacetyl-CoA synthase. In some embodiments, the genetically modified host cell comprises both an enzyme that condenses two molecules of acetyl-CoA to form acetoacetyl-CoA, e.g., acetyl-CoA thiolase; and an enzyme that condenses acetyl-CoA with malonyl-CoA to form acetoacetyl-CoA, e.g., acetoacetyl-CoA synthase.

In some embodiments, the host cell comprises more than one enzyme of the MEV pathway. In some embodiments, the host cell comprises two enzymes of the MEV pathway. In some embodiments, the host cell comprises an enzyme that can convert HMG-CoA into mevalonate and an enzyme that can convert mevalonate into mevalonate 5-phosphate. In some embodiments, the host cell comprises three enzymes of the MEV pathway. In some embodiments, the host cell comprises four enzymes of the MEV pathway. In some embodiments, the host cell comprises five enzymes of the MEV pathway. In some embodiments, the host cell comprises six enzymes of the MEV pathway. In some embodiments, the host cell seven enzymes of the MEV pathway. In some embodiments, the host cell comprises all of the enzymes of the MEV pathway.

In some embodiments, the cell further comprises an enzyme that can convert isopentenyl pyrophosphate (IPP) into dimethylallyl pyrophosphate (DMAPP). In some embodiments, the cell further comprises an enzyme that can condense IPP and/or DMAPP molecules to form a polyprenyl compound. In some embodiments, the cell further comprises an enzyme that can modify IPP or a polyprenyl to form an isoprenoid compound.

5.5.1. Conversion of Acetyl-CoA to Acetoacetyl-CoA

In some embodiments, the genetically modified host cell comprises an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*). Acetyl-CoA thiolase catalyzes the reversible condensation of two molecules of acetyl-CoA to yield acetoacetyl-CoA, but this reaction is thermodynamically unfavorable; acetoacetyl-CoA thiolysis is favored over acetoacetyl-CoA synthesis. Acetoacetyl-CoA synthase (AACS) (alternately referred to as acetyl-CoA:malonyl-CoA acyltransferase; EC 2.3.1.194) condenses acetyl-CoA with malonyl-CoA to form acetoacetyl-CoA. In contrast to acetyl-CoA thiolase, AACS-catalyzed acetoacetyl-CoA synthesis is essentially an energy-favored reaction, due to the associated decarboxylation of malonyl-CoA. In addition, AACS exhibits no thiolysis activity against acetoacetyl-CoA, and thus the reaction is irreversible. Thus, in other embodiments, the genetically modified host cell provided herein utilizes an acetoacetyl-CoA synthase to form acetoacetyl-CoA from acetyl-CoA and malonyl-CoA.

In some embodiments, the AACS is from *Streptomyces* sp. strain CL190 (Okamura et al., *Proc Natl Acad Sci USA* 107(25): 11265-70 (2010). Representative AACS nucleotide sequences of *Streptomyces* sp. strain CL190 include accession number AB540131.1, and SEQ ID NO:19 of U.S. Pat. Pub. No. 2014/0273144. Representative AACS protein sequences of *Streptomyces* sp. strain CL190 include accession numbers D7URV0, BAJ10048, and SEQ ID NO:20 of U.S. Pat. Pub. No. 2014/0273144. Other acetoacetyl-CoA synthases useful for the compositions and methods provided herein include, but are not limited to, *Streptomyces* sp. (AB183750; KO-3988 BAD86806); *S. anulatus* strain 9663 (FN178498; CAX48662); *Streptomyces* sp. KO-3988

(AB212624; BAE78983); *Actinoplanes* sp. A40644 (AB113568; BAD07381); *Streptomyces* sp. C (NZ_ACEW010000640; ZP_05511702); *Nocardiopsis dassonvillei* DSM 43111 (NZ_ABUI01000023; ZP_04335288); *Mycobacterium ulcerans* Agy99 (NC_008611; YP_907152); *Mycobacterium marinum* M (NC_010612; YP_001851502); *Streptomyces* sp. Mg1 (NZ_DS570501; ZP_05002626); *Streptomyces* sp. AA4 (NZ_ACEV01000037; ZP_05478992); *S. roseosporus* NRRL 15998 (NZ_ABYB01000295; ZP_04696763); *Streptomyces* sp. ACTE (NZ_ADFD01000030; ZP_06275834); *S. viridochromogenes* DSM 40736 (NZ_ACEZ01000031; ZP_05529691); *Frankia* sp. CcI3 (NC_007777; YP_480101); *Nocardia brasiliensis* (NC_018681; YP_006812440.1); and *Austwickia chelonae* (NZ_BAGZ01000005; ZP_10950493.1). Additional suitable acetoacetyl-CoA synthases include those described in U.S. Patent Application Publication Nos. 2010/0285549 and 2011/0281315, the contents of which are incorporated by reference in their entireties.

Acetoacetyl-CoA synthases also useful in the compositions and methods provided herein include those molecules which are said to be "derivatives" of any of the acetoacetyl-CoA synthases described herein. Such a "derivative" has the following characteristics: (1) it shares substantial homology with any of the acetoacetyl-CoA synthases described herein; and (2) is capable of catalyzing the irreversible condensation of acetyl-CoA with malonyl-CoA to form acetoacetyl-CoA. A derivative of an acetoacetyl-CoA synthase is said to share "substantial homology" with acetoacetyl-CoA synthase if the amino acid sequences of the derivative is at least 80%, and more preferably at least 90%, and most preferably at least 95%, the same as that of acetoacetyl-CoA synthase.

5.5.2. Conversion of Acetoacetyl-CoA to HMG-CoA

In some embodiments, the host cell comprises an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

5.5.3. Conversion of HMG-CoA to Mevalonate

In some embodiments, the host cell comprises an enzyme that can convert HMG-CoA into mevalonate, e.g., a HMG-CoA reductase. In some embodiments, HMG-CoA reductase is an NADPH-using hydroxymethylglutaryl-CoA reductase-CoA reductase. Illustrative examples of nucleotide sequences encoding an NADPH-using HMG-CoA reductase include, but are not limited to: (NM 206548; *Drosophila melanogaster*), (NC_002758, Locus tag SAV2545, GeneID 1122570; *Staphylococcus aureus*), (AB015627; *Streptomyces* sp. KO 3988), (AX128213, providing the sequence encoding a truncated HMG-CoA reductase; *Saccharomyces cerevisiae*), and (NC_001145: complement (115734.118898; *Saccharomyces cerevisiae*).

In some embodiments, HMG-CoA reductase is an NADH-using hydroxymethylglutaryl-CoA reductase-CoA reductase. HMG-CoA reductases (EC 1.1.1.34; EC 1.1.1.88) catalyze the reductive deacylation of (S)-HMG-CoA to (R)-mevalonate, and can be categorized into two classes, class I and class II HMGrs. Class I includes the enzymes from eukaryotes and most archaea, and class II includes the HMG-CoA reductases of certain prokaryotes and archaea. In addition to the divergence in the sequences, the enzymes of the two classes also differ with regard to their cofactor specificity. Unlike the class I enzymes, which utilize NADPH exclusively, the class II HMG-CoA reductases vary in the ability to discriminate between NADPH and NADH. See, e.g., Hedl et al., *Journal of Bacteriology* 186 (7): 1927-1932 (2004). Co-factor specificities for select class II HMG-CoA reductases are provided below.

TABLE 2

Co-factor specificities for select class II HMG-CoA reductases

| Source | Coenzyme specificity | $K_m^{NADPH}$ (μM) | $K_m^{NADH}$ (μM) |
|---|---|---|---|
| *P. mevalonii* | NADH | | 80 |
| *A. fulgidus* | NAD(P)H | 500 | 160 |
| *S. aureus* | NAD(P)H | 70 | 100 |
| *E. faecalis* | NADPH | 30 | |

Useful HMG-CoA reductases for the compositions and methods provided herein include HMG-CoA reductases that are capable of utilizing NADH as a cofactor, e.g., HMG-CoA reductase from *P. mevalonii, A. fulgidus* or *S. aureus*. In particular embodiments, the HMG-CoA reductase is capable of only utilizing NADH as a cofactor, e.g., HMG-CoA reductase from *P. mevalonii, S. pomeroyi* or *D. acidovorans*.

In some embodiments, the NADH-using HMG-CoA reductase is from *Pseudomonas mevalonii*. The sequence of the wild-type mvaA gene of *Pseudomonas mevalonii*, which encodes HMG-CoA reductase (EC 1.1.1.88), has been previously described. See Beach and Rodwell, *J. Bacteriol.* 171:2994-3001 (1989). Representative mvaA nucleotide sequences of *Pseudomonas mevalonii* include accession number M24015, and SEQ ID NO: 21 of U.S. Pat. Pub. No. 2014/0273144. Representative HMG-CoA reductase protein sequences of *Pseudomonas mevalonii* include accession numbers AAA25837, P13702, MVAA_PSEMV, and SEQ ID NO: 22 of U.S. Pat. Pub. No. 2014/0273144.

In some embodiments, the NADH-using HMG-CoA reductase is from *Silicibacter pomeroyi*. Representative HMG-CoA reductase nucleotide sequences of *Silicibacter pomeroyi* include accession number NC_006569.1, and SEQ ID NO: 23 of U.S. Pat. Pub. No. 2014/0273144. Representative HMG-CoA reductase protein sequences of *Silicibacter pomeroyi* include accession number YP_164994, and SEQ ID NO: 24 of U.S. Pat. Pub. No. 2014/0273144.

In some embodiments, the NADH-using HMG-CoA reductase is from *Delftia acidovorans*. A representative HMG-CoA reductase nucleotide sequences of *Delftia acidovorans* includes NC_010002 REGION: complement (319980.321269), and SEQ ID NO: 25 of U.S. Pat. Pub. No. 2014/0273144. Representative HMG-CoA reductase protein sequences of *Delftia acidovorans* include accession number YP_001561318, and SEQ ID NO: 26 of U.S. Pat. Pub. No. 2014/0273144.

In some embodiments, the NADH-using HMG-CoA reductases is from *Solanum tuberosum* (Crane et al., *J. Plant Physiol.* 159:1301-1307 (2002)).

NADH-using HMG-CoA reductases also useful in the compositions and methods provided herein include those molecules which are said to be "derivatives" of any of the NADH-using HMG-CoA reductases described herein, e.g., from *P. mevalonii, S. pomeroyi* and *D. acidovorans*. Such a "derivative" has the following characteristics: (1) it shares substantial homology with any of the NADH-using HMG-CoA reductases described herein; and (2) is capable of catalyzing the reductive deacylation of (S)-HMG-CoA to (R)-mevalonate while preferentially using NADH as a cofactor. A derivative of an NADH-using HMG-CoA reductase is said to share "substantial homology" with NADH-using HMG-CoA reductase if the amino acid sequences of the derivative is at least 80%, and more preferably at least 90%, and most preferably at least 95%, the same as that of NADH-using HMG-CoA reductase.

As used herein, the phrase "NADH-using" means that the NADH-using HMG-CoA reductase is selective for NADH over NADPH as a cofactor, for example, by demonstrating a higher specific activity for NADH than for NADPH. In some embodiments, selectivity for NADH as a cofactor is expressed as a $k_{cat}^{(NADH)}/k_{cat}^{(NADPH)}$ ratio. In some embodiments, the NADH-using HMG-CoA reductase has a $k_{cat}^{(NADH)}/k_{cat}^{(NADPH)}$ ratio of at least 5, 10, 15, 20, 25 or greater than 25. In some embodiments, the NADH-using HMG-CoA reductase uses NADH exclusively. For example, an NADH-using HMG-CoA reductase that uses NADH exclusively displays some activity with NADH supplied as the sole cofactor in vitro, and displays no detectable activity when NADPH is supplied as the sole cofactor. Any method for determining cofactor specificity known in the art can be utilized to identify HMG-CoA reductases having a preference for NADH as cofactor, including those described by Kim et al., *Protein Science* 9:1226-1234 (2000); and Wilding et al., *J. Bacteriol.* 182(18):5147-52 (2000), the contents of which are hereby incorporated in their entireties.

In some embodiments, the NADH-using HMG-CoA reductase is engineered to be selective for NADH over NAPDH, for example, through site-directed mutagenesis of the cofactor-binding pocket. Methods for engineering NADH-selectivity are described in Watanabe et al., *Microbiology* 153:3044-3054 (2007), and methods for determining the cofactor specificity of HMG-CoA reductases are described in Kim et al., *Protein Sci.* 9:1226-1234 (2000), the contents of which are hereby incorporated by reference in their entireties.

In some embodiments, the NADH-using HMG-CoA reductase is derived from a host species that natively comprises a mevalonate degradative pathway, for example, a host species that catabolizes mevalonate as its sole carbon source. Within these embodiments, the NADH-using HMG-CoA reductase, which normally catalyzes the oxidative acylation of internalized (R)-mevalonate to (S)-HMG-CoA within its native host cell, is utilized to catalyze the reverse reaction, that is, the reductive deacylation of (S)-HMG-CoA to (R)-mevalonate, in a genetically modified host cell comprising a mevalonate biosynthetic pathway. Prokaryotes capable of growth on mevalonate as their sole carbon source have been described by: Anderson et al., *J. Bacteriol*, 171(12):6468-6472 (1989); Beach et al., *J. Bacteriol.* 171: 2994-3001 (1989); Bensch et al., *J. Biol. Chem.* 245:3755-3762; Fimongnari et al., *Biochemistry* 4:2086-2090 (1965); Siddiqi et al., *Biochem. Biophys. Res. Commun.* 8:110-113 (1962); Siddiqi et al., *J. Bacteriol.* 93:207-214 (1967); and Takatsuji et al., *Biochem. Biophys. Res. Commun.* 110:187-193 (1983), the contents of which are hereby incorporated by reference in their entireties.

In some embodiments of the compositions and methods provided herein, the host cell comprises both a NADH-using HMGr and an NADPH-using HMG-CoA reductase.

5.5.4. Conversion of Mevalonate to Mevalonate-5-Phosphate

In some embodiments, the host cell comprises an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

5.5.5. Conversion of Mevalonate-5-Phosphate to Mevalonate-5-Pyrophosphate

In some embodiments, the host cell comprises an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM_006556; *Homo sapiens*), and (NC_001145. complement 712315.713670; *Saccharomyces cerevisiae*).

5.5.6. Conversion of Mevalonate-5-Pyrophosphate to IPP

In some embodiments, the host cell comprises an enzyme that can convert mevalonate 5-pyrophosphate into isopentenyl diphosphate (IPP), e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

5.5.7. Conversion of IPP to DMAPP

In some embodiments, the host cell further comprises an enzyme that can convert IPP generated via the MEV pathway into dimethylallyl pyrophosphate (DMAPP), e.g., an IPP isomerase. Illustrative examples of nucleotide sequences encoding such an enzyme include, but are not limited to: (NC_000913, 3031087.3031635; *Escherichia coli*), and (AF082326; *Haematococcus pluvialis*).

5.5.8. Polyprenyl Synthases

In some embodiments, the host cell further comprises a polyprenyl synthase that can condense IPP and/or DMAPP molecules to form polyprenyl compounds containing more than five carbons.

In some embodiments, the host cell comprises an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus API11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha×piperita*), (AF182827; *Mentha×pip-* erita), (MPI249453; *Mentha×piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

In some embodiments, the host cell comprises an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *Schizosaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM 202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar Copenhageni str. Fiocruz L1-130), (AB003187; *Micrococcus luteus*), (NC_002946, Locus YP 208768; *Neisseria gonorrhoeae* FA 1090), (U00090, Locus AAB91752; *Rhizobium* sp. NGR234), (J05091; *Saccharomyces cerevisiae*), (CP000031, Locus AAV93568; *Silicibacter pomeroyi* DSS-3), (AE008481, Locus AAK99890; *Streptococcus pneumoniae* R6), and (NC_004556, Locus NP 779706; *Xylella fastidiosa* Temecula1).

In some embodiments, the host cell further comprises an enzyme that can combine IPP and DMAPP or IPP and FPP to form geranylgeranyl pyrophosphate ("GGPP"), also referred to as GGPP synthase (EC 2.5.1.29). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensis* serovar *israelensis*, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides* f. *lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; Synechococcus elongates), (SAGGPS; *Sinapis alba*), (SSOGDS; *Sulfolobus acidocaldarius*), (NC_007759, Locus YP_461832; *Syntrophus aciditrophicus* SB), (NC_006840, Locus YP_204095; *Vibrio fischeri* ES114), (NM_112315; *Arabidopsis thaliana*), (ER-WCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), (NC_004350, Locus NP_721015; *Streptococcus mutans* UA159), (NP_015256; *Saccharomyces cerevisiae*); (AFC92798; *Blakeslea trispora*), (BAA14124; *Pantoea ananatis*), (AAM21639; *Cistus creticus*); (AAY33921; *Xanthophyllomyces dendrorhous*), (XP_019067954; *Solanum lycopersicum*).

5.5.9. Terpene Synthases

In some embodiments, the host cell further comprises an enzyme that can modify a polyprenyl to form a hemiterpene, a monoterpene, a sesquiterpene, a diterpene, a triterpene, a tetraterpene, a polyterpene, a steroid compound, a carotenoid, or a modified isoprenoid compound.

In some embodiments, the host cell further comprises a carene synthase. Illustrative examples of suitable nucleotide sequences include, but are not limited to: (AF461460, REGION 43.1926; *Picea abies*) and (AF527416, REGION: 78.1871; *Salvia stenophylla*).

In some embodiments, the host cell further comprises a geraniol synthase. Illustrative examples of suitable nucleotide sequences include, but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*).

In some embodiments, the host cell further comprises a linalool synthase. Illustrative examples of a suitable nucleotide sequence include, but are not limited to: (AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; Mentha citrate), (AY693647; *Ocimum basilicum*), (XM_463918; *Oryza sativa*), (AP004078, Locus BAD07605; *Oryza sativa*), (XM_463918, Locus XP_463918; *Oryza sativa*), (AY917193; *Perilla citriodora*), (AF271259; *Perilla frutescens*), (AY473623; *Picea abies*), (DQ195274; *Picea sitchensis*), and (AF444798; *Perilla frutescens* var. *crispa* cultivar No. 79).

In some embodiments, the host cell further comprises a limonene synthase. Illustrative examples of suitable nucleotide sequences include, but are not limited to: (+)-limonene synthases (AF514287, REGION: 47.1867; *Citrus limon*) and (AY055214, REGION: 48.1889; *Agastache rugosa*) and (−)-limonene synthases (DQ195275, REGION: 1.1905; *Picea sitchensis*), (AF006193, REGION: 73.1986; *Abies grandis*), and (MHC4SLSP, REGION: 29.1828; *Mentha spicata*).

In some embodiments, the host cell further comprises a myrcene synthase. Illustrative examples of suitable nucleotide sequences include, but are not limited to: (U87908; *Abies grandis*), (AY195609; *Antirrhinum majus*), (AY195608; *Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

In some embodiments, the host cell further comprises an ocimene synthase. Illustrative examples of suitable nucleotide sequences include, but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

In some embodiments, the host cell further comprises an α-pinene synthase. Illustrative examples of suitable nucleotide sequences include, but are not limited to: (+) α-pinene synthase (AF543530, REGION: 1.1887; *Pinus taeda*), (−) α-pinene synthase (AF543527, REGION: 32.1921; *Pinus taeda*), and (+)/(−) α-pinene synthase (AGU87909, REGION: 6111892; *Abies grandis*).

In some embodiments, the host cell further comprises a β-pinene synthase. Illustrative examples of suitable nucleotide sequences include, but are not limited to: (−) β-pinene synthases (AF276072, REGION: 1.1749; *Artemisia annua*) and (AF514288, REGION: 26.1834; *Citrus limon*).

In some embodiments, the host cell further comprises a sabinene synthase. An illustrative example of a suitable nucleotide sequence includes but is not limited to AF051901, REGION: 26.1798 from *Salvia officinalis*.

In some embodiments, the host cell further comprises a γ-terpinene synthase. Illustrative examples of suitable nucleotide sequences include: (AF514286, REGION: 30.1832 from *Citrus limon*) and (AB110640, REGION 1.1803 from *Citrus unshiu*).

In some embodiments, the host cell further comprises a terpinolene synthase. Illustrative examples of a suitable nucleotide sequence include, but are not limited to: (AY693650 from *Oscimum basilicum*) and (AY906866, REGION: 10.1887 from *Pseudotsuga menziesii*).

In some embodiments, the host cell further comprises an amorphadiene synthase. An illustrative example of a suitable nucleotide sequence is SEQ ID NO. 37 of U.S. Pat. Pub. No. 2004/0005678.

In some embodiments, the host cell further comprises an α-farnesene synthase. Illustrative examples of suitable nucleotide sequences include, but are not limited to DQ309034 from *Pyrus communis* cultivar d'Anjou (pear; gene name AFS1) and AY182241 from *Malus domestica* (apple; gene AFS1). Pechouus et al., *Planta* 219(1):84-94 (2004).

In some embodiments, the host cell further comprises a β-farnesene synthase. Illustrative examples of suitable nucleotide sequences include but is not limited to accession number AF024615 from *Mentha×piperita* (peppermint; gene Tspa11), and AY835398 from *Artemisia annua*. Picaud et al., *Phytochemistry* 66(9): 961-967 (2005).

In some embodiments, the host cell further comprises a farnesol synthase. Illustrative examples of suitable nucleotide sequences include, but are not limited to accession number AF529266 from *Zea mays* and YDR481C from *Saccharomyces cerevisiae* (gene Pho8). Song, L., *Applied Biochemistry and Biotechnology* 128:149-158 (2006).

In some embodiments, the host cell further comprises a nerolidol synthase. An illustrative example of a suitable nucleotide sequence includes, but is not limited to AF529266 from *Zea mays* (maize; gene tps1).

In some embodiments, the host cell further comprises a patchouliol synthase. Illustrative examples of suitable nucleotide sequences include, but are not limited to AY508730 REGION: 1.1659 from *Pogostemon cablin*.

In some embodiments, the host cell further comprises a nootkatone synthase. Illustrative examples of suitable nucleotide sequences include, but are not limited to AF441124 REGION: 1.1647 from *Citrus sinensis* and AY917195 REGION: 1.1653 from *Perilla frutescens*.

In some embodiments, the host cell further comprises an abietadiene synthase. Illustrative examples of suitable nucleotide sequences include, but are not limited to: (U50768; *Abies grandis*) and (AY473621; *Picea abies*).

In certain embodiments, the host cell produces a C5, C10, C15, or C20 as a first isoprenoid, and C30, C35, C40 or higher carbon isoprenoid as a second isoprenoid. In certain embodiments, In some embodiments, the host cell produces a C5 isoprenoid. These compounds are derived from one isoprene unit and are also called hemiterpenes. An illustrative example of a hemiterpene is isoprene. In other embodiments, the isoprenoid is a $C_{10}$ isoprenoid. These compounds are derived from two isoprene units and are also called monoterpenes. Illustrative examples of monoterpenes are limonene, citranellol, geraniol, menthol, perillyl alcohol, linalool, thujone, and myrcene. In other embodiments, the isoprenoid is a C15 isoprenoid. These compounds are derived from three isoprene units and are also called sesquiterpenes. Illustrative examples of sesquiterpenes are periplanone B, gingkolide B, amorphadiene, artemisinin, artemisinic acid, valencene, nootkatone, epi-cedrol, epi-aristolochene, farnesol, gossypol, sanonin, periplanone, forskolin, and patchoulol (which is also known as patchouli alcohol). In other embodiments, the isoprenoid is a $C_{20}$ isoprenoid. These compounds are derived from four isoprene units and also called diterpenes. Illustrative examples of diterpenes are casbene, eleutherobin, paclitaxel, prostratin, pseudopterosin, and taxadiene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene.

In yet other examples, the isoprenoid is a $C_{20+}$ isoprenoid. These compounds are derived from more than four isoprene units and include: triterpenes ($C_{30}$ isoprenoid compounds derived from 6 isoprene units) such as arbruside E, bruceantin, testosterone, progesterone, cortisone, digitoxin, and squalene; tetraterpenes ($C_{40}$ isoprenoid compounds derived from 8 isoprenoids) such as β-carotene; and polyterpenes ($C_{40+}$ isoprenoid compounds derived from more than 8 isoprene units) such as polyisoprene. Isoprenoid compounds also include, but are not limited to, carotenoids (such as lycopene, α- and β-carotene, α- and β-cryptoxanthin, bixin, zeaxanthin, astaxanthin, and lutein), steroid compounds, and compounds that are composed of isoprenoids modified by other chemical groups, such as mixed terpene-alkaloids, and coenzyme Q-10.

5.6 Carotenoid Pathway

Exemplary carotenoid biosynthetic pathways are shown in FIGS. 2, 3A, and 3B. In certain embodiments, in addition to one or more heterologous nucleic acids encoding enzymes in a biosynthetic pathway to produce a first isoprenoid, the host cell can further comprise one or more heterologous nucleic acids encoding one or more enzymes of the carotenoid biosynthetic pathway to co-produce one or more carotenoids. In certain embodiments, the carotenoid biosynthetic pathway produces one or more C40 carotenoids.

In some embodiments, the host cell comprises a heterologous nucleic acid encoding a phytoene synthase which can catalyze the conversion of geranylgeranyl pyrophosphate to phytoene. Illustrative examples of suitable polypeptide sequences or polynucleotides that encode a phytoene synthase include, but are not limited to: CrtB (*Lamprocystis purpurea*; GenBank Protein Acc.: WP_020503292) (EC 2.5.1.99 or EC 2.5.1.32).

In some embodiments, the host cell comprises a heterologous nucleic acid encoding a lycopene cyclase which can catalyse the conversion of lycopene to beta-carotene and/or the conversion of neurosporene to 7,8-dihydro-beta-carotene. Illustrative examples of suitable polypeptide sequences or polynucleotides that encode a lycopene cyclase include, but are not limited to: CrtY (*Pantoea ananatis*; GenBank Protein Acc.: BAA14126) (EC 5.5.1.19).

In some embodiments, the host cell comprises a heterologous nucleic acid encoding a bifunctional enzyme which can catalyse the conversion of geranylgeranyl pyrophosphate to phytoene (phytoene synthase) and the conversion of lycopene to β-carotene (lycopene cyclase) and/or the conversion of neurosporene to 7,8-dihydro-beta-carotene. Illustrative examples of suitable polypeptide sequences or polynucleotides that encode such a bifunctional enzyme include: CrtY/B (*Xanthophyllomyces dendrohous*; Verwaal et al. App. Environ. 733(13):4342-50 (2007); CrtY/B (*Phycomyces blakesleeanus*; GenBank Protein Acc.: XP_018294563), CrtY/B (*Neurospora crassa*; GenBank Protein Acc.: XP_965725), and CrtY/B (*Blakeslea trispora*; GenBank Protein Acc.: AA046893).

In some embodiments, the host cell comprises a heterologous nucleic acid encoding a phytoene desaturase which can catalyse the conversion of phytoene to neurosporene and/or the conversion of neurosporene to lycopene. Illustrated examples of suitable polypeptide sequences or polynucleotides that encode a phytoene desaturase include, but are not limited to: CrtI (*Xanthophyllomyces dendrohous*; Verwaal et al. *App. Environ. Microbiol.* 73(130:4342-50, 2007) CrtI (*Xanthophyllomyces dendrohous*; GenBank Protein Acc.: CAA75240), CrtI (*Mycobacterium goodie*; GenBank Protein Acc.: WP_049747535), CrtI (*Neurospora crassa*; GenBank Protein Acc.: XP_964713), CrtI (*Paenibacillus*_sp; GenBank Protein Acc.: WP_042140268), and CrtI (*Bradyrhizobium*_sp; GenBank Protein Acc.: WP_011924720) (EC 1.3.99.31 or EC 1.3.5.5 or EC 1.3.5.6 or EC 1.3.99.28 or EC 1.3.99.30).

In some embodiments, the host cell comprises a heterologous nucleic acid encoding beta-carotene ketolase which can catalyze the conversion of beta-carotene to echinenone, the conversion of echinenone to canthaxanthin, the conversion of beta-cryptoxanthin to 3-hydroxyechinenone/3'-hydroxyechinenone, the conversion of 3-hycroxyechinenone/3'-hydroxyechinenone to phenicoxanthin, the conversion of zeaxanthin to adonixanthin, and/or the conversion of adonixanthin to astaxanthin. Illustrated examples of suitable polypeptide sequences or polynucleotides include, but are not limited to: CrtW (*Paracoccus*_sp.; GenBank Protein Acc.: BAA09591), CrtW (*Brevundimonas* sp; GenBank Protein Acc.: BAD99406), CrtW (*Haematococcus lacustris*; GenBank Protein Acc.: ADN43075), CrtW (*Chlamydomonas reinhardtii*; XP_001698699), CrtW (*Sphingomonas* sp. 1PNM-20; GenBank Protein Acc.:WP_095996876); CrtW (*Paracoccus* sp. Strain N81106 (*Agrobacterium aurantiacum*) GenBank ID: BAE47465.1; UniProt CRTW_PARSN; Ukibe et al., *Appl. Environ. Microbiol.* 75(22): 7205-7211 (2009)); HpBkt (*Haematococcus pluvialis*; GenBank ID D45881.1; BAA08300.1) (EC 1.14.11.B16 or EC 1.3.5.B4).

In certain embodiments, the host cell comprises a heterologous nucleic acid encoding a beta-carotene hydroxylase which can catalyse the conversion of beta-carotene to beta-cryptoxanthin, the conversion of beta-cryptoxanthin to zeaxanthin, the conversion of echinenone to 3-hydroxyechinenone/3'-hydroxyechinenone, the conversion of 3-hydroxyechinenone/3'-hydroxyechinenone to adonixanthin, the conversion of canthaxanthin to phenicoxanthin, and/or the conversion of phenicoxanthin to astaxanthin. Illustrated examples of suitable polypeptide sequences or polynucleotides include, but are not limited to: CrtZ (*Escherichia vulneris*; GenBank Protein Acc.: WP_042387980), CrtZ (*Pantoea ananatis*; GenBank Protein Acc.: WP_013027996), CrtZ (*Paracoccus* sp.; GenBank Protein Acc.:Q44262), CrtZ (*Haematococcus lacustris*; GenBank Protein Acc.:AKQ20654); CrtZ (*Paracoccus* sp. Strain N81106 (*Agrobacterium aurantiacum*) GenBank ID BAE47466.1; CRTZ_PARSN); CrtZ (*Pantoea ananatis*; GenBank ID ADD79330.1; UnitPro D4GFL0_PANAM; Ukibe et al. (2009); HpCrtZ (*Haematococcus pluvialis*; GenBank KP866868.1; AKQ20654.1) (EC 1.14.13.129).

In certain embodiments, the host cell comprises a heterologous nucleic acid encoding a cytochrome p450 hydroxylase which can catalyse the conversion of α-carotene to echinenone, the conversion of echinenone to 3-hydroxyechinenone/3'-hydroxyechinenone, the conversion of 3-hydroxyechinenone/3'-hydroxyechinenone to phenicoxanthin, and/or the conversion of phenicoxanthin to astaxanthin. Illustrative examples of suitable polypeptide sequences or polynucleotides include, but are not limited to: CrtS (*Xanthophyllomyces dendrorhous*; AAY20974; UniProt Q3HR17_PHARH).

In certain embodiments, the host cell comprises a heterologous nucleic acid encoding a cytochrome-p450 reductase which can interact with a cytochrome p450 hydroxylase (CrtS) in host cells in catalysing the conversion of β-carotene to astaxanthin in the astaxanthin pathway as shown in FIG. 3A. Illustrative examples of suitable polypeptide sequences or polynucleotides include, but are not limited to: CrtR (*Xanthophyllomyces dendrorhous*; ACI43097); and (*Xanthophyllomyces dendrohous*; Gen Bank ID AIP94032.1; UniProt A0A0C4MWF8_PHARH) (EC 1.6.2.4).

A host cell can comprise any one or combination of heterologous nucleic acids encoding enzymes of the carotenoid pathway described herein to produce a target carotenoid compound.

5.7 Modifications to Increase Acetyl-CoA Levels

In certain embodiments, any of the above cells producing compounds from acetyl-CoA, comprise modifications to their acetyl-CoA pathways according to U.S. 2014/0273144 A1. In certain embodiments, the cells comprise a phosphoketolase (PK; EC 4.1.2.9) and a functional disruption of an endogenous enzyme that converts acetyl phosphate to acetate. In certain embodiments, the cells comprise a phosphotransacetylase (PTA; EC 2.3.1.8); and a functional disruption of an endogenous enzyme that converts acetyl phosphate to acetate. In some embodiments, the enzyme that converts acetyl phosphate to acetate is a glycerol-1-phosphatase (EC 3.1.3.21). In some embodiments, the glycerol-1-phosphatase is selected from the group consisting of GPP1/RHR2, GPP2HOR2, and homologues and variants thereof. In some embodiments, the host cell comprises a functional disruption of GPP1/RHR2. In some embodiments, the host cell comprises a functional disruption of GPP2/HOR2. In some embodiments, the host cell comprises a functional disruption of both GPP1/RHR2 and GPP2/HOR2. In some embodiments, the host cell further comprises an acylating acetylaldehyde dehydrogenase (ADA; EC 1.2.1.10). In some embodiments, host cell further comprises a functional disruption of one or more enzymes of the native pyruvate dehydrogenase (PDH)-bypass. In some embodiments, the one or more enzymes of the PDH-bypass are selected from acetyl-CoA synthetase 1 (ACS1), acetyl-CoA synthetase 2 (ACS2), and aldehyde dehydrogenase 6 (ALD6).

5.8 Methods of Producing Isoprenoids

In certain embodiments, provided herein is a method for the production of two or more isoprenoids as target compounds. The method comprises: (a) culturing, in a culture medium with a carbon source, a host cell genetically modified with one or more heterologous nucleic acids encoding one or more enzymes in a first biosynthetic pathway to produce a first isoprenoid and one or more heterologous nucleic acid encoding one or more enzymes in a second biosynthetic pathway to produce second isoprenoid, which has a molecular weight that is different from the first isoprenoid; and (b) recovering the first isoprenoid, and (c) recovering the second isoprenoid. In certain embodiments, the host cell is not genetically modified to produce a target compound which is not derived from IPP. In certain embodiments, the fermentation is performed by culturing the genetically modified host cells in a culture medium comprising a carbon source under suitable culture conditions for a period of time sufficient to produce a desired biomass of the host cells and/or a desired amount of isoprenoids.

In certain embodiments, the fermentation process is carried out in two stages—a build stage and a production stage. The build stage is carried out for a period of time sufficient to produce an amount of cellular biomass that can support production of target isoprenoids during the production stage. The build stage is carried out for a period of time sufficient for the population present at the time of inoculation to undergo a plurality of doublings until a desired cell density is reached. In some embodiments, the build stage is carried out for a period of time sufficient for the host cell population to reach a cell density ($OD_{600}$) of between 0.01 and 400 in the fermentation vessel or container in which the build stage is being carried out. In some embodiments, the build stage is carried out until an $OD_{600}$ of at least 0.01 is reached. In some embodiments, the build stage is carried out until an $OD_{600}$ of at least 0.1 is reached. In some embodiments, the build stage is carried out until an $OD_{600}$ of at least 1.0 is reached. In some embodiments, the build stage is carried out until an $OD_{600}$ of at least 10 is reached. In some embodiments, the build stage is carried out until an $OD_{600}$ of at least 100 is reached. In some embodiments, the build stage is carried out until an $OD_{600}$ of between 0.01 and 100 is reached. In some embodiments, the build stage is carried out until an $OD_{600}$ of between 0.1 and 10 is reached. In some embodiments, the build stage is carried out until an $OD_{600}$ of between 1 and 100 is reached. In other embodiments, the build stage is carried for a period of at least 12, 24, 36, 48, 60, 72, 84, 96 or more than 96 hours.

In some embodiments, the production stage is carried out for a period of time sufficient to produce a desired amount of target isoprenoids. In some embodiments, the production stage is carried out for a period of at least 12, 24, 36, 48, 60, 72, 84, 96 or more than 96 hours. In some embodiments, the production stage is carried out for a period of between 3 and 20 days. In some embodiments, the production stage is carried for a period of 1, 2, 3, 4, 5, 6, 7, 8, 9, 10, 11, 12, 13, 14, 15, 16, 17, 18, 19, 20 or more than 20 days.

In a particular embodiment, the method of producing target isoprenoids comprises conducting fermentation of the genetically modified host cell under aerobic conditions sufficient to allow growth and maintenance of the genetically modified host cell; then subsequently providing microaerobic fermentation conditions sufficient to induce production of target isoprenoids, and maintaining the microaerobic conditions throughout the fermentation run. In certain embodiments, the microaerobic conditions are used throughout the fermentation run. In certain embodiments, the aerobic conditions are used throughout the fermentation run.

In certain embodiments, the production of the elevated level of target isoprenoids by the host cell is inducible by an inducing compound. Such a host cell can be manipulated with ease in the absence of the inducing compound. The inducing compound is then added to induce the production of the elevated level of isoprenoid by the host cell. In other embodiments, production of the elevated level of isoprenoid by the host cell is inducible by changing culture conditions, such as, for example, the growth temperature, media constituents, and the like.

In certain embodiments, an inducing agent is added during the production stage to activate a promoter or to relieve repression of a transcriptional regulator associated with a biosynthetic pathway to promote production of target isoprenoids. In certain embodiments, an inducing agent is added during the build stage to repress a promoter or to activate a transcriptional regulator associated with a biosynthetic pathway to repress the production of target isoprenoids, and an inducing agent is removed during the production stage to activate a promoter to relieve repression of a transcriptional regulator to promote the production of target isoprenoids. The term "genetic switch" is used herein to refer to the use of a promoter or other genetic elements to control activation or de-activation of the biosynthetic pathway for the isoprenoid production. Illustrative examples of useful inducing agent or a genetic switch for controlling target isoprenoid production are described in, e.g., PCT Application Publications WO2015/020649, WO2016/210343, and WO2016210350, which are incorporated herein by reference in their entirety.

In another embodiment, the method of producing target isoprenoids comprises culturing host cells in separate build and production culture media. For example, the method can comprise culturing the genetically modified host cell in a build stage wherein the cell is cultured under non-producing conditions (e.g., non-inducing conditions) to produce an inoculum, then transferring the inoculum into a second fermentation medium under conditions suitable to induce target isoprenoid production (e.g., inducing conditions), and maintaining steady state conditions in the second fermentation stage to produce a cell culture containing target isoprenoids.

Figure 4:
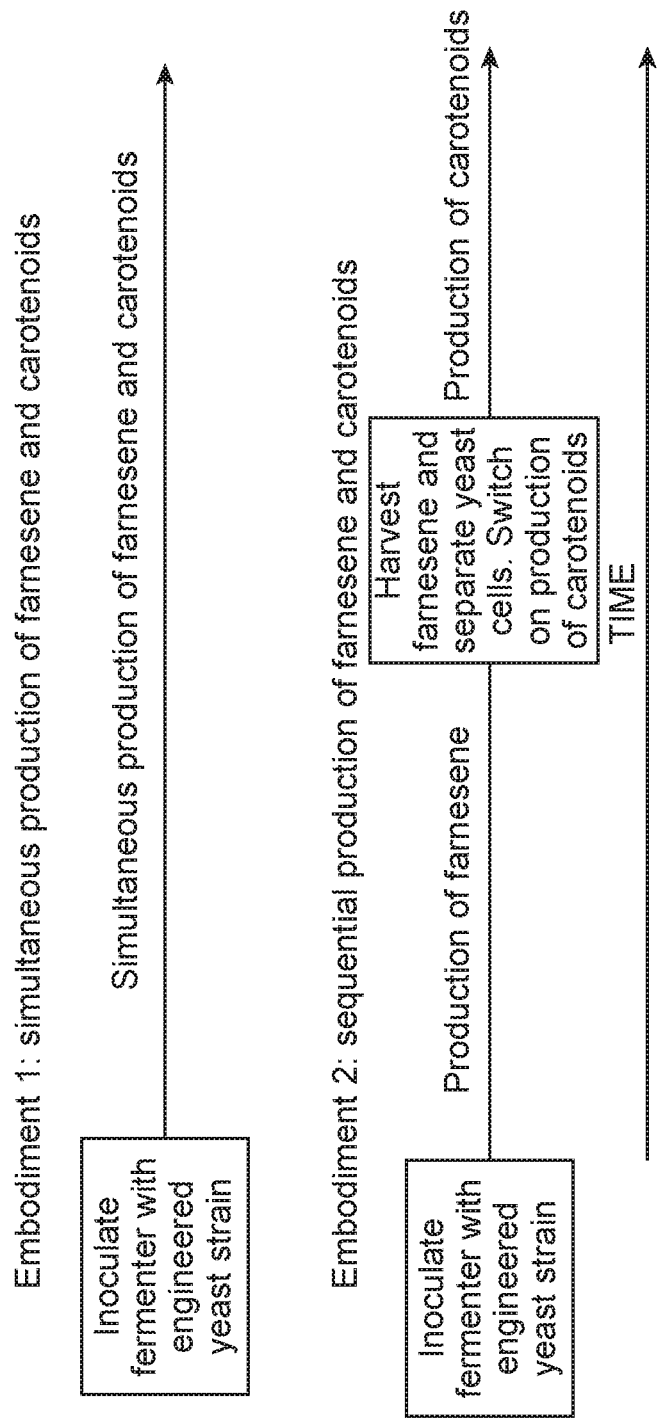
FIG. 4 illustrates two different embodiments of co-production of farnesene and carotenoids.
Figure 5:
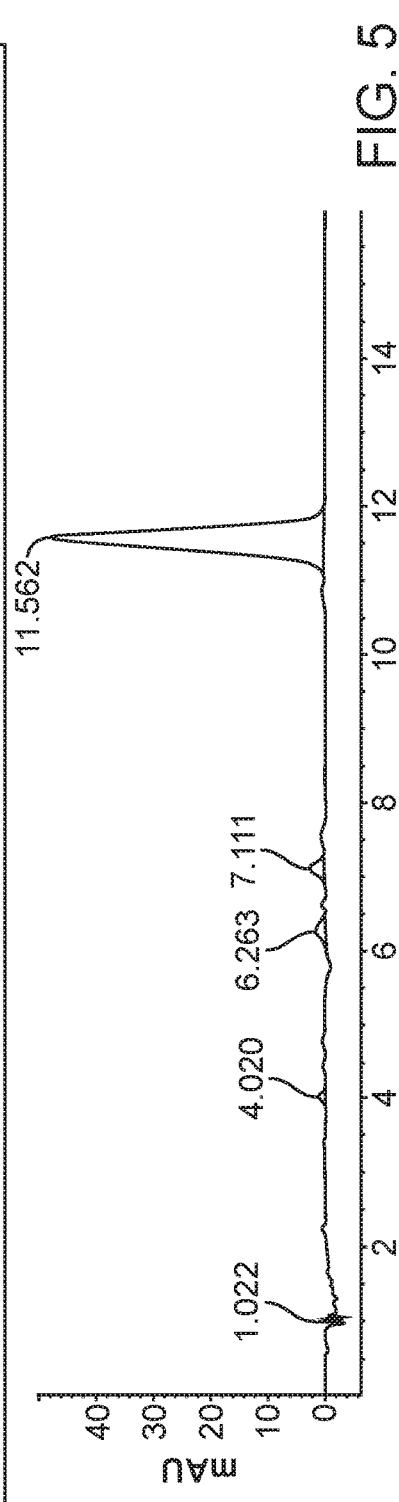
FIG. 5 illustrates the elution of beta-carotene at 11.5 min from the column in an HPLC.

As illustrated in FIG. 4, the two or more target isoprenoids can be produced concurrently or sequentially. Embodiment 1 of FIG. 4 illustrates co-production of target isoprenoids (e.g., farnesene and carotenoids) simultaneously or concurrently in a single fermentation run. For concurrent co-production of target isoprenoids, in some embodiments, the biosynthetic pathways for the target isoprenoids are constitutively active. In other embodiments, for concurrent co-production of target isoprenoids, the biosynthetic pathway for the target isoprenoids can be under the control of the same genetic switch or an inducer. For example, the biosynthetic pathways for the production of farnesene and carotenoids may be under the control of pGal promoters, which are regulated by the Gal regulon. Examples of the Gal regulon which are further repressed or induced by a maltose are described in PCT Application Publications WO2015/020649, WO2016/210343, and WO2016210350. In certain embodiments, the production of a first isoprenoid can be induced first, followed by induction of the production of the second isoprenoid in a single fermentation run.

Embodiment 2 of FIG. 4 illustrates a sequential production of isoprenoids from in two fermentation runs after inoculation. In this embodiment, the first isoprenoid can be produced during the first fermentation run, and the second isoprenoid can be produced during the second fermentation run. In some embodiments, the first isoprenoid can be produced during the first fermentation run, and both first and second isoprenoids can be produced during the second fermentation run.

In certain embodiments, the culturing and recovering comprises: (a) culturing a single inoculum comprising the host cell to build a population of the host cell; (b) culturing the population of the host cell under conditions to produce the first isoprenoid from the population of the host cells, wherein the conditions do not activate production of the second isoprenoid; (c) separating and recovering the first isoprenoid from the population; (d) after separating the first isoprenoid, culturing the population or a subpopulation of the host cell under conditions to activate production of the second isoprenoid; and recovering the second isoprenoid.

In certain embodiments, the first isoprenoid is predominantly released from the host cell into the culture medium, and the second isoprenoid predominantly remains with the cell fraction (e.g., inside the cell). In certain embodiments, the second isoprenoid is recovered together with the host cell.

In some embodiments, the genetically modified host cell produces an increased amount of an isoprenoid compared to a parent cell not comprising the one or more modifications, or a parent cell comprising only a subset of the one or more modifications of the genetically modified host cell, but is otherwise genetically identical. In some embodiments, the increased amount is at least 1%, 5%, 10%, 15%, 20%, 25%, 30%, 35%, 40%, 45%, 50%, 55%, 60%, 65%, 70%, 75%, 80%, 85%, 90%, 95%, 100% or greater than 100%, as measured, for example, in yield, production, productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the host cell produces an elevated level of a first isoprenoid that is greater than about 10 grams per liter of fermentation medium. In some such embodiments, the isoprenoid is produced in an amount from about 10 to about 50 grams, more than about 15 grams, more than about 20 grams, more than about 25 grams, or more than about 30 grams per liter of cell culture.

In some embodiments, the host cell produces an elevated level of a first isoprenoid that is greater than about 50 milligrams per gram of dry cell weight. In some such embodiments, the isoprenoid is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the host cell produces an elevated level of an isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by a parent cell, on a per unit volume of cell culture basis.

In some embodiments, the host cell produces an elevated level of an isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by the parent cell, on a per unit dry cell weight basis.

In some embodiments, the host cell produces an elevated level of an isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by the parent cell, on a per unit volume of cell culture per unit time basis.

In some embodiments, the host cell produces an elevated level of an isoprenoid that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the level of isoprenoid produced by the parent cell, on a per unit dry cell weight per unit time basis.

In some embodiments, the genetically modified host cell produces comparable amount of the first isoprenoid compared to a parent cell not producing the second isoprenoid. In some embodiments, the comparable amount is at least 90%, 95%, 100% or greater than 100% compared to the parent amount, as measured, for example, in yield, production, productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

In some embodiments, the genetically modified host cell produces comparable amount of the second isoprenoid compared to a parent cell not producing the first isoprenoid. In some embodiments, the comparable amount is at least 90%, 95%, 100% or greater than 100% compared to the parent amount, as measured, for example, in yield, production, productivity, in grams per liter of cell culture, milligrams per gram of dry cell weight, on a per unit volume of cell culture basis, on a per unit dry cell weight basis, on a per unit volume of cell culture per unit time basis, or on a per unit dry cell weight per unit time basis.

5.9 Culture Media and Conditions

Materials and methods for the maintenance and growth of microbial cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing isoprenoids provided herein may be performed in a suitable culture medium (e.g., with or without pantothenate supplementation) in a suitable container, including but not limited to a cell culture plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany.

In some embodiments, the culture medium is any culture medium in which a genetically modified microorganism capable of producing an isoprenoid can subsist, i.e., maintain growth and viability. In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients, are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, xylose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol.

The concentration of a carbon source, such as glucose, in the culture medium should promote cell growth, but not be so high as to repress growth of the microorganism used. Typically, cultures are run with a carbon source, such as glucose, being added at levels to achieve the desired level of growth and biomass, but at undetectable levels (with detection limits being about <0.1 g/l). In other embodiments, the concentration of a carbon source, such as glucose, in the culture medium is greater than about 1 g/L, preferably greater than about 2 g/L, and more preferably greater than about 5 g/L. In addition, the concentration of a carbon source, such as glucose, in the culture medium is typically less than about 100 g/L, preferably less than about 50 g/L, and more preferably less than about 20 g/L. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Typically, the concentration of the nitrogen sources, in the culture medium is greater than about 0.1 g/L, preferably greater than about 0.25 g/L, and more preferably greater than about 1.0 g/L. Beyond certain concentrations, however, the addition of a nitrogen source to the culture medium is not advantageous for the growth of the microorganisms. As a result, the concentration of the nitrogen sources, in the culture medium is less than about 20 g/L, preferably less than about 10 g/L and more preferably less than about 5 g/L. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Typically, the concentration of phosphate in the culture medium is greater than about 1.0 g/L, preferably greater than about 2.0 g/L and more preferably greater than about 5.0 g/L. Beyond certain concentrations, however, the addition of phosphate to the culture medium is not advantageous for the growth of the microorganisms. Accordingly, the concentration of phosphate in the culture medium is typically less than about 20 g/L, preferably less than about 15 g/L and more preferably less than about 10 g/L.

A suitable culture medium can also include a source of magnesium, preferably in the form of a physiologically acceptable salt, such as magnesium sulfate heptahydrate, although other magnesium sources in concentrations that contribute similar amounts of magnesium can be used. Typically, the concentration of magnesium in the culture medium is greater than about 0.5 g/L, preferably greater than about 1.0 g/L, and more preferably greater than about 2.0 g/L. Beyond certain concentrations, however, the addition of magnesium to the culture medium is not advantageous for the growth of the microorganisms. Accordingly, the concentration of magnesium in the culture medium is typically less than about 10 g/L, preferably less than about 5 g/L, and more preferably less than about 3 g/L. Further, in some instances it may be desirable to allow the culture medium to become depleted of a magnesium source during culture.

In some embodiments, the culture medium can also include a biologically acceptable chelating agent, such as the dihydrate of trisodium citrate. In such instance, the concentration of a chelating agent in the culture medium is greater than about 0.2 g/L, preferably greater than about 0.5 g/L, and more preferably greater than about 1 g/L. Beyond certain concentrations, however, the addition of a chelating agent to the culture medium is not advantageous for the growth of the microorganisms. Accordingly, the concentration of a chelating agent in the culture medium is typically less than about 10 g/L, preferably less than about 5 g/L, and more preferably less than about 2 g/L.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

The culture medium can also include a biologically acceptable calcium source, including, but not limited to, calcium chloride. Typically, the concentration of the calcium source, such as calcium chloride, dihydrate, in the culture medium is within the range of from about 5 mg/L to about 2000 mg/L, preferably within the range of from about 20 mg/L to about 1000 mg/L, and more preferably in the range of from about 50 mg/L to about 500 mg/L.

The culture medium can also include sodium chloride. Typically, the concentration of sodium chloride in the culture medium is within the range of from about 0.1 g/L to about 5 g/L, preferably within the range of from about 1 g/L to about 4 g/L, and more preferably in the range of from about 2 g/L to about 4 g/L.

In some embodiments, the culture medium can also include trace metals. Such trace metals can be added to the culture medium as a stock solution that, for convenience, can be prepared separately from the rest of the culture medium. Typically, the amount of such a trace metals solution added to the culture medium is greater than about 1 ml/L, preferably greater than about 5 mL/L, and more preferably greater than about 10 mL/L. Beyond certain concentrations, however, the addition of a trace metals to the culture medium is not advantageous for the growth of the microorganisms. Accordingly, the amount of such a trace metals solution added to the culture medium is typically less than about 100 mL/L, preferably less than about 50 mL/L, and more preferably less than about 30 mL/L. It should be noted that, in addition to adding trace metals in a stock solution, the individual components can be added separately, each within ranges corresponding independently to the amounts of the components dictated by the above ranges of the trace metals solution.

The culture media can include other vitamins, such as pantothenate, biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture, including pantothenate during the production stage of the fermentation. In some embodiments, the culture may be supplemented with relatively high concentrations of such components at the outset, for example, of the production stage, so that growth and/or isoprenoid production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of isoprenoid. For example, prior to inoculation of the culture medium with an inoculum, the culture medium can be brought to and maintained at a temperature in the range of from about 20° C. to about 45° C., preferably to a temperature in the range of from about 25° C. to about 40° C., and more preferably in the range of from about 28° C. to about 32° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, more preferably from about 3.5 to about 7.0, and most preferably from about 4.0 to about 6.5.

In some embodiments, the carbon source concentration, such as the glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium. As stated previously, the carbon source concentration should be kept below the level at which cell growth inhibition occurs. Although such concentration may vary from organism to organism, for glucose as a carbon source, cell growth inhibition occurs at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, more preferably in the range of from about 2 g/L to about 50 g/L, and yet more preferably in the range of from about 5 g/L to about 20 g/L. Although the carbon source concentration can be maintained within desired levels by addition of, for example, a substantially pure glucose solution, it is acceptable, and may be preferred, to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

5.10 Recovery of Isoprenoids

Once an isoprenoid is produced by the host cell, it may be recovered or isolated for subsequent use using any suitable separation and purification methods known in the art. In some embodiments, an organic phase comprising the isoprenoid is separated from the fermentation by centrifugation. In other embodiments, an organic phase comprising the isoprenoid separates from the fermentation spontaneously. In other embodiments, an organic phase comprising the isoprenoid is separated from the fermentation by adding a demulsifier and/or a nucleating agent into the fermentation reaction. Illustrative examples of demulsifiers include flocculants and coagulants. Illustrative examples of nucleating agents include droplets of the isoprenoid itself and organic solvents such as dodecane, isopropyl myristrate, and methyl oleate.

The isoprenoid produced in these cells may be present in the culture supernatant and/or associated with the host cells. In embodiments where the isoprenoid is associated with the host cell, the recovery of the isoprenoid may comprise a method of permeabilizing or lysing the cells. Alternatively or simultaneously, the isoprenoid in the culture medium can be recovered using a recovery process including, but not limited to, chromatography, extraction, solvent extraction, membrane separation, electrodialysis, reverse osmosis, distillation, chemical derivatization and crystallization.

In some embodiments, the isoprenoid is separated from other products that may be present in the organic phase. In some embodiments, separation is achieved using adsorption, distillation, gas-liquid extraction (stripping), liquid-liquid extraction (solvent extraction), ultrafiltration, and standard chromatographic techniques.

In some embodiments, the first isoprenoid produced in these cells may be present in the culture supernatant and the second isoprenoid produced in these cells may be associated with the host cells. In these embodiments, since two isoprenoid products are in different phases, it is easier to separate and recover the two isoprenoid products. The methods for separating and recovering the second isoprenoids, such as carotenoids, are described in the Example section below.

Methods of Making Genetically Modified Cells

Also provided herein are methods for producing a host cell that is genetically engineered to comprise one or more of the modifications described above, e.g., one or more heterologous nucleic acids encoding biosynthetic pathway enzymes, e.g., for co-production of isoprenoid compounds. Expression of a heterologous enzyme in a host cell can be accomplished by introducing into the host cells a nucleic acid comprising a nucleotide sequence encoding the enzyme under the control of regulatory elements that permit expression in the host cell. In some embodiments, the nucleic acid is an extrachromosomal plasmid. In other embodiments, the nucleic acid is a chromosomal integration vector that can integrate the nucleotide sequence into the chromosome of the host cell.

Nucleic acids encoding these proteins can be introduced into the host cell by any method known to one of skill in the art without limitation (see, for example, Hinnen et al. (1978) *Proc. Natl. Acad. Sci.* USA 75:1292-3; Cregg et al. (1985) *Mol. Cell. Biol.* 5:3376-3385; Goeddel et al. eds, 1990, Methods in Enzymology, vol. 185, Academic Press, Inc., CA; Krieger, 1990, Gene Transfer and Expression—A Laboratory Manual, Stockton Press, NY; Sambrook et al., 1989, Molecular Cloning—A Laboratory Manual, Cold Spring Harbor Laboratory, NY; and Ausubel et al., eds., Current Edition, Current Protocols in Molecular Biology, Greene Publishing Associates and Wiley Interscience, NY). Exemplary techniques include, but are not limited to, spheroplasting, electroporation, PEG 1000 mediated transformation, and lithium acetate or lithium chloride mediated transformation.

The copy number of an enzyme in a host cell may be altered by modifying the transcription of the gene that encodes the enzyme. This can be achieved for example by modifying the copy number of the nucleotide sequence encoding the enzyme (e.g., by using a higher or lower copy number expression vector comprising the nucleotide sequence, or by introducing additional copies of the nucleotide sequence into the genome of the host cell or by deleting or disrupting the nucleotide sequence in the genome of the host cell), by changing the order of coding sequences on a polycistronic mRNA of an operon or breaking up an operon into individual genes each with its own control elements, or by increasing the strength of the promoter or operator to which the nucleotide sequence is operably linked. Alternatively or in addition, the copy number of an enzyme in a host cell may be altered by modifying the level of translation of an mRNA that encodes the enzyme. This can be achieved for example by modifying the stability of the mRNA, modifying the sequence of the ribosome binding site, modifying the distance or sequence between the ribosome binding site and the start codon of the enzyme coding sequence, modifying the entire intercistronic region located "upstream of" or adjacent to the 5' side of the start codon of the enzyme coding region, stabilizing the 3'-end of the mRNA transcript using hairpins and specialized sequences, modifying the codon usage of enzyme, altering expression of rare codon tRNAs used in the biosynthesis of the enzyme, and/or increasing the stability of the enzyme, as, for example, via mutation of its coding sequence.

The activity of an enzyme in a host cell can be altered in a number of ways, including, but not limited to, expressing a modified form of the enzyme that exhibits increased or decreased solubility in the host cell, expressing an altered form of the enzyme that lacks a domain through which the activity of the enzyme is inhibited, expressing a modified form of the enzyme that has a higher or lower Kcat or a lower or higher Km for the substrate, or expressing an altered form of the enzyme that is more or less affected by feed-back or feed-forward regulation by another molecule in the pathway.

In some embodiments, a nucleic acid used to genetically modify a host cell comprises one or more selectable markers useful for the selection of transformed host cells and for placing selective pressure on the host cell to maintain the foreign DNA.

In some embodiments, the selectable marker is an antibiotic resistance marker. Illustrative examples of antibiotic resistance markers include, but are not limited to, the BLA, NAT1, PAT, AUR1-C, PDR4, SMR1, CAT, mouse dhfr, HPH, DSDA, KAN$^R$, and SH BLE gene products. The BLA gene product from *E. coli* confers resistance to beta-lactam antibiotics (e.g., narrow-spectrum cephalosporins, cephamycins, and carbapenems (ertapenem), cefamandole, and cefoperazone) and to all the anti-gram-negative-bacterium penicillins except temocillin; the NAT1 gene product from *S. noursei* confers resistance to nourseothricin; the PAT gene product from *S. viridochromogenes* Tu94 confers resistance to bialophos; the AUR1-C gene product from *Saccharomyces cerevisiae* confers resistance to Auerobasidin A (AbA); the PDR4 gene product confers resistance to cerulenin; the SMR1 gene product confers resistance to sulfometuron methyl; the CAT gene product from Tn9 transposon confers resistance to chloramphenicol; the mouse dhfr gene product confers resistance to methotrexate; the HPH gene product of *Klebsiella pneumonia* confers resistance to Hygromycin B; the DSDA gene product of *E. coli* allows cells to grow on plates with D-serine as the sole nitrogen source; the KAN$^R$ gene of the Tn903 transposon confers resistance to G418; and the SH BLE gene product from *Streptoalloteichus hindustanus* confers resistance to Zeocin (bleomycin). In some embodiments, the antibiotic resistance marker is deleted after the genetically modified host cell disclosed herein is isolated.

In some embodiments, the selectable marker rescues an auxotrophy (e.g., a nutritional auxotrophy) in the genetically modified microorganism. In such embodiments, a parent microorganism comprises a functional disruption in one or more gene products that function in an amino acid or nucleotide biosynthetic pathway and that when non-functional renders a parent cell incapable of growing in media without supplementation with one or more nutrients. Such gene products include, but are not limited to, the HIS3, LEU2, LYS1, LYS2, MET15, TRP1, ADE2, and URA3 gene products in yeast. The auxotrophic phenotype can then be rescued by transforming the parent cell with an expression vector or chromosomal integration construct encoding a functional copy of the disrupted gene product, and the genetically modified host cell generated can be selected for based on the loss of the auxotrophic phenotype of the parent cell. Utilization of the URA3, TRP1, and LYS2 genes as selectable markers has a marked advantage because both positive and negative selections are possible. Positive selection is carried out by auxotrophic complementation of the URA3, TRP1, and LYS2 mutations, whereas negative selection is based on specific inhibitors, i.e., 5-fluoro-orotic acid (FOA), 5-fluoroanthranilic acid, and aminoadipic acid (aAA), respectively, that prevent growth of the prototrophic strains but allows growth of the URA3, TRP1, and LYS2 mutants, respectively. In other embodiments, the selectable marker rescues other non-lethal deficiencies or phenotypes that can be identified by a known selection method.

Described herein are specific genes and proteins useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutations and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias."

Optimized coding sequences containing codons preferred by a particular prokaryotic or eukaryotic host (Murray et al., 1989, *Nucl Acids Res.* 17: 477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al., 1996, *Nucl Acids Res.* 24: 216-8).

Those of skill in the art will recognize that, due to the degenerate nature of the genetic code, a variety of DNA molecules differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA molecules of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as the modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for the compositions and methods provided herein are encompassed by the disclosure. In some embodiments, two proteins (or a region of the proteins) are substantially homologous when the amino acid sequences have at least about 30%, 40%, 50%, 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol Biol* 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. A typical algorithm used comparing a molecule sequence to a database containing a large number of sequences from different organisms is the computer program BLAST. When searching a database containing sequences from a large number of different organisms, it is typical to compare amino acid sequences.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorpha*, *Candida* spp., *Trichosporon* spp., *Yamadazyma* spp., including *Y.* spp. *stipitis*, *Torulaspora pretoriensis*, *Issatchenkia orientalis*, *Schizosaccharomyces* spp., including *S. pombe*, *Cryptococcus* spp., *Aspergillus* spp., *Neurospora* spp., or *Ustilago* spp. Sources of genes from anaerobic fungi include, but are not limited to, *Piromyces* spp., *Orpinomyces* spp., or *Neocallimastix* spp. Sources of prokaryotic enzymes that are useful include, but are not limited to, *Escherichia coli*, *Zymomonas mobilis*, *Staphylococcus aureus*, *Bacillus* spp., *Clostridium* spp., *Corynebacterium* spp., *Pseudomonas* spp., *Lactococcus* spp., *Enterobacter* spp., *Salmonella* spp., or *X. dendrorhous*

Techniques known to those skilled in the art may be suitable to identify additional homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous PK, PTA, RHR2, HOR2, or carotenogic genes, proteins, or enzymes, techniques may include, but are not limited to, cloning a gene by PCR using primers based on a published sequence of a gene/enzyme of interest, or by degenerate PCR using degenerate primers designed to amplify a conserved region among a gene of interest. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity (e.g. as described herein or in Kiritani, K., *Branched-Chain Amino Acids Methods Enzymology*, 1970), then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein.

6. EXAMPLES

6.1 Parent Farnesene Production Strain

A "non-switchable" farnesene production strain was derived from a wild-type *Saccharomyces cerevisiae* strain (CEN.PK2) and also comprises the following chromosomally integrated mevalonate pathway genes from *S. cerevisiae* under the control of GAL promoters: acetyl-CoA thiolase, HMG-CoA synthase, HMG-CoA reductase, mevalonate kinase, phosphomevalonate kinase, and mevalonate pyrophosphate decarboxylase; and six copies of farnesene synthase mutants from *Artemisia annua*. The non-switchable farnesene production strain has GAL80 gene deleted and an additional copy of GAL4 under GAL4oc promoter, wherein the coding sequence of the GAL4 gene of *Saccharomyces cerevisiae* is under regulatory control of an "operative constitutive" version of its native promoter (PGAL4oc; see, e.g., Griggs & Johnston (1991) PNAS 88(19):8597-8601).

Farnesene production in the "non-switchable" strain was then made "switchable," that is, repressible in the presence of maltose. The maltose switchable strain is built on top of the non-switchable strain by chromosomally integrating a copy of GAL80 under the control of maltose-responsive promoter such as pMAL32. Additional description of switchable farnesene producing switchable strains are described in U.S. Patent Application Publication No. US 2016/0177341 and PCT Application Publication No. WO 2016/210350, which are incorporated herein by reference.

In certain strains, the switchable farnesene strains were further genetically engineered according to Meadows et al. (2016), U.S. Pat. Nos. 8,603,800, 9,410,214, which are incorporated herein by reference.

6.2 UV-Based Farnesene Quantitation and Cell Density Measurements

The farnesene titer was measured according to methods described in Meadows et al. (2016). 600 μL of 2-butoxyethanol was added to 150 μL of whole-cell broth in three additions of 200 μl each, with 90 s of shaking at 1,000 r.p.m. on a 96-well plate shaker between each addition. The samples were then incubated for 40 min. 8 μl of the 2-butoxyethanol extract was mixed with 200 μl of isopropyl alcohol in a 96-well UV plate (Costar 3635), then read on a plate reader for absorbance at 222 nM. Farnesene titer was calculated based on absorbance of a standard dilution series.

$OD_{600}$ was measured as previously described in Meadows et al. (2016) and Sandoval et al. (2015) *Metabol. Eng.* 25, 215-226 (2014).

6.3 β-Carotene Production by Farnesene Production Strain

To test if carotenoids could be co-produced in addition to farnesene, as valorization molecules, five pathway genes were introduced into the farnesene production strain under pGAL promoters. The introduced genes include: GGPPS, Xd.CrtYB, Xd.CrtI, Hp.CrtZ, and Hp.Bkt (or GGPPS, Xd.CrtYB, Xd.CrtI, Pa.CrtZ, and Ps.CrtW) into the switchable farnesene production strain described above. Twenty-seven combinations of different gene dosage (e.g., different copies of pathway genes) were tested. In all of the twenty-seven transformation plates, yellow or orange colonies were observed (FIG. 10), indicating the accumulation of β-carotene, but none in red which is the color of astaxanthin. Notably, the color only started to appear 6 days after plating, likely due to the low expression of carotenoid biosynthesis pathway genes under the control of the maltose switch. Genetic analysis by colony PCR showed that the astaxanthin biosynthesis genes had not integrated. Representative β-carotene-producing colonies were subsequently chosen for transformation with astaxanthin biosynthesis genes.

6.4 Astaxanthin Production by Farnesene Production Strain

Astaxanthin production strain was built on top of the farnesene production strain comprising pGAL 3 operably linked to GGPPS, one copy of nucleic acid encoding CrtI and four copies of nucleic acids encoding CrtYB. The astaxanthin pathway was completed by adding either Hp.CrtZ and Hp.Bkt gene or Pa.CrtZ and Ps.CrtW. Both sets of enzymes led to red colonies indicative of the production of astaxanthin (FIG. 11). This experiment illustrates that astaxanthin could remain inside the cells in the presence of farnesene. After production and recovery of farnesene, spent microbial cells with astaxanthin inside the cells can be valorized as an animal feed (e.g., farmed salmon).

6.5 Concurrent Production of Astaxanthin and Farnesene by Yeast Strains

FIG. 12 shows production of farnesene by strains engineered to produce carotenoids β-carotene or astaxanthin). Strain A (also referred to as strain Y021) is the base farnesene production strain described in Section 6.1, and Strain B is a variant of Strain A used for introduction of the carotenoid pathway genes. Strain C is derived from Strain B comprising additional genes as shown in FIG. 12. Additional strains shown in FIG. 12 are derived from Strain C. In the "off-state" of production, all the strains grow (measured by off-state cell density $OD_{600}$) and produce farnesene (measured by off-state farnesene titer as shown by the UV-based assay). See Section 6.2. In the off-state all strains engineered for the production of carotenoids also produce carotenoids (data not shown). During the on-state (when the isoprenoid production is activated), the cultures containing the carotenoid genes do not grow as well as in the off-state (when the isoprenoid production is not activated). See FIG. 12. The strains also produce much less farnesene than strain A, or their parental Strain B. This result illustrates that farnesene can be produced first, and then the carotenoid production can be turned on.

In FIG. 12, the cell density ($OD_{600}$) was measured as follows. An 8 μL sample of a cell culture was combined with 92 μL of Triton OD Diluent (20 g/L Triton X-114, 200 mL/L PEG 200, 200 mL/L 100% ethanol, rest water) in a clear 96-well plate, the solution was agitated at 1,000 RPM for 6 minutes, and the $OD_{600}$ was determined by measuring absorbance at 600 nm on an M5 spectrophotometer (Molecular Devices, Sunnyvale, CA).

In FIG. 12, the farnesene titer was measured using the whole broth using the UV-based assay described herein. See Section 6.2. Other suitable methods such as gas chromatography can be used to measure the farnesene titer.

In general, for preculture conditions, the strains were cultured were gown in sterile 96-well plates (1.1 ml working volume; Axygen) containing 360 μl of Bird Seed Media (BSM, originally described by van Hoek et al. (2000). For the preculture conditions, the carbon source was typically a mixture of 1.4% sucrose and 0.7% maltose, unless indicated otherwise. Single colonies were picked into each well and incubated for approximately 72 hours at 33.5° C., 80% humidity and 1000 rpm (Infors Multitron; ATR Biotec).

For farnesene production experiments, the aforementioned saturated cultures were diluted 1/25 into sterile 1.1 ml plates containing 145 μl of BSM. Typically, the carbon source was either 4% sucrose, or a mixture of 2.3% sucrose and 1.7% maltose, unless indicated otherwise. After 72 hours of culture, farnesene extraction was performed by adding 600 μl of isopropyl alcohol (IPA) to each well. After 30-minute incubation, 8 μl was transferred to a clear bottom assay plate containing 192 μl IPA. Farnesene concentration was measured by UV absorbance at 222 nm on a SpectraMax plate reader.

6.6 β-Carotene and Astaxanthin Production Verified by HPLC

6.6.1. Extraction Method Development

Various extraction methods were attempted to extract beta-carotene and astaxanthin out of the cells. The idea is to pellet the cells and extract the compounds from the pellet since carotenoids do not seem to be secreted out of the cells, as judged by the color of the supernatant. Initially, pellets were solubilized in DMSO and compounds extracted using various non-polar solvents which was further diluted into methanol-THF solution before being injected onto the HPLC. The solvent combinations tried were as follows: a) 100% heptane b) 1:1 mixture of met hanol-THF c) 1:1 mixture of heptane-THF d) 1:1 mixture of methanol-acetone and d) 100% pentane. The extractions were also compared with the "no extraction" condition, in which the DMSO extract was directly diluted into methanol-THF solution and analyzed by HPLC.

Sample prep protocol: In a typical sample prep, 120 μL of the whole cell broth was centrifuged at 13000 rpm for 60 s. The clear supernatant was discarded and the resulting bright yellow/orange pellet was then reconstituted in approximately 400 μL DMSO and vortexed for 15 s to mix the contents. The resulting mixture was centrifuged at the same speed for 30 s and 100 μL of this DMSO extract was then added to 200 μL of the 1:1 methanol-THF solution and analyzed by HPLC-UV.

Results and discussion: All extractions were done using the same sample. The sample size and solvent volumes also remained the same throughout. The best possible extraction condition was chosen by comparing the relative peak areas from different extractions. It should be noted that no other corrections were done to account for the differences in the densities of the solvents. We noticed that the extractions using a neat heptane or pentane resulted in the maximum peak area of beta-carotene and this was comparable to the "no extraction" condition. The DMSO only condition was chosen in order to avoid an additional step in the extraction procedure. Furthermore, DMSO has been reported to rupture the cell membranes that may already play a role in an efficient extraction/dissociation of carotenoids from the cells. The single extraction step, however, is not complete as it did not result in the complete de-coloration of the resulting cell pellet (by visual inspection). Treating the DMSO extract at 70° C. for about 10 min also did not lead to a complete extraction (carotenoids are stable up to 80° C.)[3]. In a follow-up experiment, the extraction can be repeated at least thrice to verify the amounts of material still left in the pellet.

6.6.2. Standards Preparation

Beta-carotene was very hard to dissolve in solvents like ethyl acetate, methanol or isopropanol even at 50 mg/L level. While it would be ideal to use highly non-polar solvents such as heptane, hexane or pentane to dissolve the compound, the solvents' immiscibility with the HPLC mobile phase made it a difficult choice. In this example, dichloromethane was used to make a stock solution of beta-carotene followed by further dilution of that stock in acetone to obtain required final concentrations of the beta-carotene solution for the calibration standards. The solutions were immediately transferred to the amber bottle, purged with nitrogen (to remove any air in the headspace) and capped. Calibrators were then aliquoted into GC vials (~300 μL each) and stored in the −80° C. freezer. Each aliquot is taken out, thawed at room temperature and analyzed when required. The vials were discarded after a single use.

6.6.3. HPLC Method Development

Initial attempts to elute beta-carotene standards using a C18 or C8 reverse phase HPLC column with the mobile phase solvent combinations of methanol, acetonitrile and water did not work.[4] Majority of the literature suggest using either non-polar chlorinated solvents or an ether in the mobile phase to elute beta-carotene using the reverse phase column.[5,6] Since using a chloroform or dichloromethane poses an elevated health risk compared to using an ether, we chose tetrahydrofuran as a co-solvent in the mobile phase. The column and elution parameters are as follows:

TABLE 3

HPLC column and elution parameters.

| Column | Zorbax-SB-C18 |
|---|---|
| specification | 100 mm × 3.5 u × 4.6 mm i.d. |
| Mobile phase A | 100% acetonitrile |
| Mobile phase B | Methanol with 25% THF (v/v) |
| Ramp | 60% A:40% B |
| flow rate | 1 mL/min - isocratic |
| Time | 16 min |
| Injection volume | 3 μL |
| detector wavelength | 450 nm, 480 nm and 210 nm |

FIG. 9 shows various strain samples extracted and analyzed using the conditions mentioned in this report: A) GGPPS grandparent strain with no downstream genes, expectedly, showing no signs of beta-carotene or astaxanthin; B) parent strain containing only genes encoding for beta-carotene clearly shows the presence of the same after extraction and analysis. The identity of the second peak at 13.3 min is not clear at the moment. We suspect this to be the dihydro analog of beta-carotene which is a known by-product of crtYB gene (ref: Verwaal et al, 2007) C) daughter strain clearly shows the presence of astaxanthin at 1.4 min along with beta-carotene and other potential carotenoids. It is not surprising to find beta-carotene in the daughter strain. The identities of other smaller peaks are not known and they could potentially be other downstream carotenoids (more polar than beta-carotene, likely oxygenated forms) or may also contain some degradation or transformed analogs of astaxanthin.

6.7 Final Carotenoid Extraction Method and Analytical Results

Table 4 illustrates various strains which were built on top of an isogenic strain comprising the chromosomally integrated mevalonate pathway genes from S. cerevisiae. The additional genes (e.g., farnesene synthase, GGPP synthase, beta-carotene or astaxanthin biosynthetic pathway genes) incorporated into different strains are shown in Table 4.

Cells were grown in flasks for 48 hours then switched to 1.8% glucose 0.2% galactose for 48 hours before extraction. Strains from which carotenoids were extracted are described in Table 4.

TABLE 4

Strains from which carotenoids were extracted. These strains were generated from a farnesene-producing strain derived from Y337 (Westfall et al, 2012) in which amorphadiene synthase had been removed and replaced with farnesene synthase.

| Strains | Description |
| --- | --- |
| Grandparent strain 1 | (5X FS + GGPPS) |
| Grandparent strain 2 | (15X FS + GGPPS) |
| Parent strain 1 | (5X FS + GGPPS) + (2 CrtI:1 Crt YB) + Empty plasmid |
| Parent strain 2 | (15X FS + GGPPS) + (2 CrtI:1 Crt YB) + Empty plasmid |
| Child strain 1 | (5X FS + GGPPS) + (2 CrtI:1 Crt YB) + (Ps.CrtW_3 + Ps.CrtZ_3) |
| Child strain 2 | (15X FS + GGPPS) + (2 CrtI:1 Crt YB) + (Ps.CrtW_3 + Ps.CrtZ_3) |

The 6 steps used for sample extraction are as follows:
1. 400 uL WCB added to 2.2 mL microcentrifuge tube.
2. Pellet remaining after samples are spun 45 seconds at 13,000 rpm in a bench-top microcentrifuge.
3. Colorless supernatant removed by pipette.
4. 1000 uL DMSO added to pellet, vortexed for 30 seconds twice.
5. Spun 45 seconds at 13,000 rpm on bench top microcentrifuge.
6. Pellet checked for remaining colour—150 uL of supernatant added to 150 ul 1:1 MeOH:THF mix in amber GC vial with insert, ready for HPLC.

HPLC traces from Grandparent strain 1, Parent strain 1, and Child strain 1 clearly showing that no carotenoids are present without the β-carotene genes, that two clear peaks (β-carotene at 11.6 minutes and a peak thought to be hydroxyl β-carotene at 13.3 minutes), and that astaxanthin (1.42 minutes) and a number of other carotenoids, as well as some α-carotene, are present in the reddest colonies (FIG. 9). FIG. 9 demonstrates that Child strain 1 produces astaxanthin.

6.8 Example: Co-Production of Carotenoids and a Sesquiterpene and its Impact on the Sesquiterpene Production and Cell Density This example illustrates that a high flux farnesene strain can be further genetically engineered to coproduce carotenoids without substantially reducing the production of farnesene and the cell biomass yield.

6.8.1. DNA Assembly and Transformations

Multi-component DNA constructs were generated using DNA assembly methods as previously described (De Kok et al. (2014) ACS Synth. Biol. 21; 3(2):97-106. doi: 10.1021/sb4001992; Serber et al., U.S. Pat. No. 8,221,982). Linear fragments of donor DNA cassettes are transformed into a host cell for integration into the host cell genome according to methods described in Horwitz et al. Cell Syst. July 29; 1(1):88-96 (2015) and DiCarlo et al. Nucleic Acids Res., 41 (2013), pp. 4336-4343). Transformation into a host for genomic integration was executed using the optimized S. cerevisiae LiAc methods (Gietz and Woods, Methods Enzymol. 2002; 350:87-96). Each marker-less integrations were confirmed using a colony PCR.

6.8.2. Media and Strain Cultivation

Co-production of farnesene and carotenoids was conducted in 96-well microtiter plate at 1,000 rpm shaking with 80% relative humidity. Cultures used for the inoculation of the microtiter plates were maintained on synthetic complete medium agar plates at 28° C. with 2% glucose, 1% maltose, 2 g/L lysine and 50 µg/mL G418. Colonies were picked into wells in sterile, 96-well microtiter plates (1.1 mL working volume; Axygen) containing 360 mL of defined liquid growth bird seed media (BSM) with 2% total carbon (1.4% sucrose, 0.7% maltose) and 1 g/L lysine. This pre-culture plate was incubated for 72 hrs. at 28° C., 80% humidity and 1000 rpm (Infors Multitron; ATR Biotec). The initial biomass build was diluted 1/25 into two sterile 1.1 mL plates containing (i) 360 mL of defined liquid growth bird seed media containing 4% sucrose as a carbon source and this plate was used to measure biomass yield and carotenoid species and (ii) 150 uL of defined growth media with 4% sucrose as a carbon source. The first plate was incubated for four days before it was used to measure biomass yield and carotenoids production using the UV-UPLC assay. Farnesene was measured after incubating the second plate for 3 days and extracting the full well with isopropanol and measured using a UV-based assay. See Section 6.2.

6.8.3. Results: Production of Canthaxanthin and Other Carotenoid Intermediates In this experiment, farnesene producing strain Y011 was used as the base farnesene producing strain. Strain Y011 is another switchable farnesene producing strain comprising genetic elements described in Example 6.1, and is a variant of strain Y021 described in Section 6.5. The S. cerevisiae codon optimized sequences of Phycomyces blakesleeanus phytoene synthase/lycopene cyclase, Neurospora crassa phytoene synthase/lycopene cyclase, Xanthophyllomyces dendrorhous (Phaffia rhodozyma) phytoene desaturase and Paracoccus sp. β-carotene ketolase were initially integrated into the host cell genome using constructs designed as convergent, split expression cassettes. In addition, the native S. cerevisiae BTS1 (geranylgeranyl diphosphate synthase), ERG8 (phosphomevalonate kinase) and MVD1 (mevalonate pyrophosphate decarboxylase) were also overexpressed after integrating a second split construct into the host cell genome. Both constructs were integrated into the genome of Y011 as described above and gene expression of each construct was driven using the strong native strong pGAL1/10 bidirectional promoter. Strains were constructed as described above (see Materials and Methods) and transformants were selected on agar plate containing 50 µg/mL G418. Correct integrations were verified by colony PCR. Strains Y924 and Y925 are two resulting clones with correct integrations.

We assessed farnesene and carotenoid production after growing the cells in defined Bird Seed media with 4% sucrose for 3 days (farnesene) or media with 4% sucrose only for 4 days (carotenoid and biomass).

Our data indicate that carotenoid co-producer strains Y924 and Y925 (derived from Y011) can make a substantial amount of each of canthaxanthin, lycopene, phytoene, and β-carotene. However, the biomass yield was significantly lower than the parent (producing only farnesene). As a result, these strains produced less farnesene than the parent in 96 wells plate. A substantial reduction of both farnesene production and the biomass yield is shown in FIG. 13. The negative effects of co-producing a high level of carotenoids in farnesene producing strains led us to our next hypothesis that expression of carotenoid pathway encoding genes at lower level will direct us to generation of healthier strains.

6.9 Example: Co-Production of Carotenoids and Sesquiterpene without Reducing the Sesquiterpene and Biomass Yield This example illustrates that the carotenoid pathway can be modified such that the primary isoprenoid product, farnesene, can be co-produced with a carotenoid without sacrificing the amount of farnesene or biomass yield, compared to a parent host cell genetically engineered to produce only farnesene. In this example, the carotenoid "upper" pathway shown in FIG. 2 was expressed using promoters of different strengths, each promoter operably linked to the nucleic acids encoding the enzymes of the carotenoid biosynthetic pathway.

In Example 6.7, all of the carotenoid pathway encoding genes, including a second copy of BTS1 (the native GGPS genes), were expressed using our strongest bidirectional promoter, pGAL1/10 (Table 5). In order to test the hypothesis that expression of carotenoid pathway encoding genes at lower level will lead us to healthier co-producing strains, we chose a native promoter (pGAL3) and a semi-synthetic promoter (pGAL2_v10) that have different promoter strength relative to pGAL1 (Table 5). The promoter strength of the semi-synthetic pGAL2_v10 promoter is about equivalent to that of the endogenous pGAL7 promoter.

TABLE 5

Relative promoter strength as measured by expression of GFP in wild type CEN.PK2 strain using galactose as a sugar source

| Promoter | Promoter Strength relative to pGAL1 |
|---|---|
| pGAL1 | 1 |
| pGAL2_v10 | 0.36 |
| pGAL3 | 0.11 |

In this experiment, we expressed only the "upper" carotenoid pathway leading to the production of β-carotene (see FIG. 2), and we did not overexpress a second copy of BTS1. In the farnesene producing strain (Y011) described above, we integrated, into the genome, the *S. cerevisiae* codon optimized sequences of phytoene synthase/lycopene cyclase (CrtYB) and phytoene desaturase (CrtI) of *Xanthophyllomyces dendrorhous* (*Phaffia rhodozyma*). The construct were designed as convergent, expression cassettes. We tested different combination of promoters to express the "upper" carotenoid pathway. We evaluated farnesene, biomass and carotenoid productions after growing the cells for 3 days in 96 wells microtiter plates as described above. Our data indicate that these new co-producer strains, Y854 (pGAL3>CrtYB; pGAL2_v10>CrtI) Y855 (pGAL3>CrtYB; pGAL3>CrtI) co-produced at least 1.0 mg/L of β-carotene and 1.93 mg/L in microtiter plates, respectively, with no impact on farnesene and biomass production. See FIGS. 14A and 14B. In addition, these strains produced about 1.1 to 1.4 mg/L phytoene, suggesting further pathway optimization can potentially lead to co-production of higher β-carotene level without affecting farnesene production.

6.10 Example: Co-Production/Sequential Production of Sesquiterpene and Carotenoids and their Ratio of Production This example illustrates that the ratio of sesquiterpene and carotenoid that can be co-produced or sequentially produced without greatly impacting the production of the primary isoprenoid, sesquiterpene, or the biomass yield.

6.10.1. DNA Assembly and Transformations

Multi-component DNA constructs were generated using DNA assembly methods as previously described (De Kok et al. (2014) *ACS Synth. Biol.* 21; 3(2):97-106. doi: 10.1021/sb4001992; Serber et al., U.S. Pat. No. 8,221,982). Linear fragments of donor DNA cassettes are transformed into a host cell for integration into the host cell genome according to methods described in Horwitz et al. (2015) and DiCarlo et al. (2013). Transformation into a host for genomic integration was executed using the optimized *S. cerevisiae* LiAc methods (Gietz and Woods, 2002). Each marker-less integrations were confirmed using a colony PCR.

For the strain constructed using the estradiol responsive promoters, Y440, the genes encoding the *Blakeslea trispora* GGPPS, *Xanthophyllomyces dendrorhous* CrtI, and *Haematococcus pluvialis* β-carotene ketolase and β-carotene hydroxylase were expressed using the strongest estradiol responsive promoter described before (McIssac et al. (2014) *Nucleic Acids Res.* 42: e48) while the *Xanthophyllomyces dendrorhous* CrtYB was used expressed using semi-synthetic promoter (pGAL2_v10).

6.10.2. Media and Strain Cultivation with Estradiol

Co-production of farnesene and carotenoids was conducted in 96-well microtiter plate at 1,000 rpm shaking with 80% relative humidity. Cultures used for the inoculation of the microtiter plates were maintained on synthetic complete medium agar plates at 28° C. with 2% glucose, 1% maltose, 2 g/L lysine and 50 µg/mL G418. Colonies were picked into wells in sterile, 96-well microtiter plates (1.1 mL working volume; Axygen) containing 360 mL of defined liquid growth bird seed media (BSM) with 2% total carbon (1.4% sucrose, 0.7% maltose) and 1 g/L lysine. This pre-culture plate was incubated for 72 hrs. at 28° C., 80% humidity and 1000 rpm (Infors Multitron; ATR Biotec). The initial biomass build was diluted 1/25 into two sterile 1.1 mL plates containing (i) Plate 1: 360 mL of defined liquid growth bird seed media containing 4% sucrose as a carbon source and this plate was used to measure biomass concentration (g dry cell weight per liter of culture) and carotenoid species in absence or presence of 15 nM of estradiol (hereafter referred as "co-production") and (ii) Plate 2: 150 uL of defined growth media with 4% sucrose as a carbon source containing an oil surfactant emulsification in absence or presence of 15 nM of estradiol and was used in order to measure farnesene production. In the second round of inoculation, the biomass from Plate 1 (with no addition of estradiol) was spun down and 25% of the biomass was inoculated into either (a) a total volume of 360 mL of defined liquid growth bird seed media containing 4% sucrose and 50 mM estradiol or (b) 150 uL of defined growth media with 4% sucrose and 50 mM estradiol containing an oil surfactant (hereafter referred to as "sequential"). The inoculated plates were either used to measure biomass yield and carotenoid species in a sequential process or were used to measure farnesene production respectively. Biomass, farnesene and carotenoid production was measured after 24-72 hours of incubation.

6.10.3. Carotenoid/Xanthophyll Extraction Protocol

After culturing, cells are centrifuged at max speed for 5 min to pellet. Supernatant is removed by pipetting. DMSO (dimethyl sulfoxide) is added to the pellet—adding 2 times the final culture volume. The vessel is sealed and incubated at room temperature on a shaker at 1500 rpm for 30 min. Equal volume n-heptane is then added to the DMSO-cell mix. This is sealed and incubated again at RT, 1500 rpm, 30 min. Approximately, 1/6 the culture volume of Phosphate Buffered Saline, pH 7.0, is then added to the DMSO-heptane-cell mix to increase the polarity of the DMSO layer. This is shaken for an additional 5 min. The mix is then centrifuged at 5,000×g for 5 min to settle the layers and pellet any cell debris. An aliquot of the top, heptane layer is transferred to a new container that can be loaded onto an analytical instrument for analysis.

6.10.4. Carotenoid/Xanthophyll Assay Protocols

6.10.4.1 UHPLC-DAD Method for Detection and Quantification of Carotenoids and Xanthophylls Extracted samples and calibration curves are run on a Thermo Scientific Vanquish series UHPLC with diode array detector (DAD). 2 uL sample volume is injected onto the column (Agilent Eclipse Plus C8 2.1 uM×100 mM 1.8) using an 8.5 minute gradient method from 60% solvent B to 90% B (Solvent A: 50% MeOH/Water 5 mM Ammonium Acetate, 0.1% HOAc; Solvent B: 10%/80%/10% MeOH/IPA/Water 5 mM Ammonium Acetate 0.1% HOAc). The method used has a flow rate of 0.5 ml/min and a column temperature of 45 Celsius. Wavelengths used for detection are 260 nm (Phytoene) 471 nm (Lycopene), 454 nm ((β-Carotene, Canthaxanthin and Astaxanthin).

6.10.4.2 Measurement of Xanthophylls in Whole Cell Extracts by Mass Spectrometry (MS)

Extracted samples along with pre-mixed calibration curve standards are submitted to Themis database to generate worklist and then in turn run in Agilent 6545 QTOF using atmospheric pressure chemical ionization (APCI) source and automsms mode. Volume of 5 uL is injected into the column (50×2.1 mm i.d. Poroshell 120 SB-C8, Part #689775-906) using 3 minute gradient method from 40% B to 100% B solvent (Mobile Phase A: 50% MeOH/Water 5 mM Ammonium Acetate, 0.1% HOAc; Mobile Phase B: 10%/80%/10% MeOH/IPA/Water 5 mM Ammonium Acetate 0.1% HOAc. The method used has a flow rate of 0.4 ml/min and column temperature of 60 deg Celsius. A preferred list of the analytes is created to generate MS/MS fragmentation pattern for further identification analytes produced. Data is then analyzed and calculated using Qual and Quant Masshunter to identify product and generate titer measurement.

6.10.5. Co-Production Results

This result describes the results of co-production experimental design described in Section 6.9.2.

The parent strain (Y021), which is a high flux farnesene producing strain, produces farnesene in both in the absence and presence of estradiol (15 nM), but it does not make any carotenoids or xanthophylls under either growth conditions.

As described above, strain Y440 (described in Section 6.10.1) is genetically modified to produce both farnesene and carotenoids. When the genes encoding carotenoids biosynthesis are induced at a low level (by the addition of 15 nM estradiol), then β-carotene is produced as well as farnesene. The difference in the farnesene production in the parent strain Y021 versus strain Y440 was negligible (e.g., less than 5 wt. %). The difference in the biomass concentration (g dry cell weight per liter of culture) in the parent strain Y021 versus strain Y440 was also negligible (e.g., less than 5%). These results demonstrate the production and secretion of a product (i.e., farnesene) into the culture medium and a cell-associated carotenoid (β-carotene), without greatly impacting the farnesene production amount or biomass yield. In this experiment, the ratio of weight of f-carotene to weight of farnesene produced per plate was determined to be about 0.01%.

6.10.6. Sequential Production Results

This result section describes the sequential production experimental design described in 6.10.2. In the first production culture (PC) when the genes encoding carotenoid production are not induced, farnesene is produced but not β-carotene. Following transfer of 25% of this culture to a second fermentation in which the genes encoding carotenoid and xanthophyll biosynthetic enzymes are induced at high-level by the presence of 50 nM estradiol, both a carotenoid (β-carotene) and xanthophylls (canthaxanthin and lutein/zeaxanthin) can be detected. This demonstrates sequential production in which farnesene is produced in the first production culture, and carotenoids (and incidental farnesene production) are produced in the second production culture. In this experiment, the ratio of weight of β-carotene to weight of farnesene produced from the weight of β-carotene is about 0.03%.

6.11 Example: Co-Production of Farnesene and Carotenoids in a Fermentor Culture Strain Y440 was cultivated in a 0.5 L fermentor using the protocol described in Meadows et al. (2016), except that the sugar feed was Brazilian cane syrup. 15 nM estradiol was added to the medium in the 0.5 L fermentor upon inoculation with Y440, and to all subsequent additions of media, so that the concentration of estradiol in the fermentor was maintained at 15 nM. After cultivation for greater than 48 hours, the culture contained 4.8 g farnesene per Kg of whole cell broth and 7 mg of carotenoids (lycopene plus β-carotene). This corresponds to an approximate production ratio of 0.14% carotenoids to farnesene by weight.

The following references are incorporated herein by reference in their entirety:

1. Westfall, P. J., et al., *Production of amorphadiene in yeast, and its conversion to dihydroartemisinic acid, precursor to the antimalarial agent artemisinin*. Proc Natl Acad Sci USA, 2012. 109(3): p. E111-8.
2. Meadows, A. L., et al., *Rewriting yeast central carbon metabolism for industrial isoprenoid production*. Nature, 2016. 537(7622): p. 694-697.
3. Verwaal, R., et al., *High-level production of beta-carotene in Saccharomyces cerevisiae by successive transformation with carotenogenic genes from Xanthophyllomyces dendrorhous*. Appl Environ Microbiol, 2007. 73(13): p. 4342-50.
4. Ukibe, K., et al., *Metabolic engineering of Saccharomyces cerevisiae for astaxanthin production and oxidative stress tolerance*. Appl Environ Microbiol, 2009. 75(22): p. 7205-11.
5. McIsaac, R. S., et al., *Synthetic biology tools for programming gene expression without nutritional perturbations in Saccharomyces cerevisiae*. Nucleic Acids Res, 2014. 42(6): p. e48.

6. Bendjilali, N., et al., *Time-Course Analysis of Gene Expression During the Saccharomyces cerevisiae Hypoxic Response*. G3: Genes|Genomes|Genetics, 2017. 7(1): p. 221-231.
7. Notman et al. Molecular basis for dimethylsulfoxide (DMSO) action on lipid membranes *J. Am. Chem. Soc.*, 128, 2006, 13982-13983.
8. He et al. Ion transport through dimethyl sulfoxide (DMSO) induced transient water pores in cell membranes. *Mol. Membr. Biol.* 3-4, 2012, 107-113.
9. Kim, J. K., Kim, J. I., Lee, N. K., Hahm, Y. T., Baik, M. Y., Kim, B. Y. Extraction of β-carotene produced from yeast *Rhodosporidium* sp. and its heat stability *Food Sci. Biotechnol.* 19, 2010, 263-266.
10. Sol Maiam rivera Velez. Guide for carotenoid identification in biological samples *J. Nat. Prod.* Doi: 10.1021/acs.jnatprod. 5b00756
11. O'Connor, K. C., Vella, G. J. Non-aqueous reverse phase purification of carotenes on a small particle preparative packing.
12. McIssac, R. S. et al (2014) Nucleic Acids Res. 42: e48. Doi: 10.1093/nar/gkt1402

One or more features from any embodiments described herein or in the figures may be combined with one or more features of any other embodiment described herein in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A method for co-production of two or more isoprenoids, the method comprising:
   (a) culturing, in a culture medium, a host cell genetically modified with one or more heterologous nucleic acids encoding one or more enzymes in a first biosynthetic pathway to produce a first isoprenoid and with one or more heterologous nucleic acids encoding one or more enzymes in a second biosynthetic pathway to produce a second isoprenoid, which has a molecular weight that is different from the first isoprenoid wherein the first isoprenoid is produced and secreted into the culture medium, and wherein the second isoprenoid is produced and remains associated with the host cell, and wherein the host cell co-produces about 2.5 g/L to about 200 g/L of the first isoprenoid compound and about 1 mg/L to about 4000 mg/L of the second isoprenoid compound;
   (b) recovering the first isoprenoid from the culture medium; and
   (c) recovering the second isoprenoid from the host cell.

2. The method of claim 1 wherein the host cell is not genetically modified to produce a target compound for recovery other than a compound derived from isopentenyl pyrophosphate (IPP).

3. The method for co-production of isoprenoids of claim 1, wherein the first isoprenoid and second isoprenoid are produced concurrently during a fermentation run from a single inoculum.

4. The method for co-production of isoprenoids of claim 1, wherein the first isoprenoid and second isoprenoid are produced sequentially from a single inoculum comprising the host cell, or sequentially using a genetic switch.

5. The method for co-production of isoprenoids of claim 1, wherein the culturing and recovering comprise:
   (a) culturing the single inoculum comprising the host cell to build a population of host cells;
   (b) culturing the population of host cells under conditions to produce the first isoprenoid from the population of host cells, wherein the conditions do not activate production of the second isoprenoid;
   (c) recovering the first isoprenoid from the population;
   (d) after separating the first isoprenoid, culturing the population or a subpopulation of the host cells under conditions to activate production of the second isoprenoid; and
   (e) recovering the second isoprenoid.

6. The method for co-production of isoprenoids of claim 1, wherein the first isoprenoid is predominantly released from the host cell into the culture medium and the second isoprenoid predominantly remains intracellularly.

7. The method for co-production of isoprenoids of claim 1, wherein the second isoprenoid predominantly remains intracellularly and is recovered together with the host cell mass.

8. The method for co-production of claim 1, wherein the first isoprenoid is a C5, C10, C15, or C20 isoprenoid, and wherein the second isoprenoid is a C30, C35, C40, or higher carbon isoprenoid.

9. The method for co-production of isoprenoids of claim 1, wherein the first isoprenoid is a C15 isoprenoid and the second isoprenoid is a C40 isoprenoid.

10. The method for co-production of isoprenoids of claim 1, wherein the first isoprenoid is farnesene and the second isoprenoid is a carotenoid.

11. The method for co-production of isoprenoids of claim 1, wherein the second isoprenoid is astaxanthin, xanthophyll, or ketocarotenoid; or the second isoprenoid is one or more of astaxanthin, canthaxanthin, zeaxanthin, β-carotene, lycopene, and lutein.

12. The method for co-production of isoprenoids of claim 1, wherein the first isoprenoid is a sesquiterpene and the second isoprenoid is one or more carotenoids; wherein the ratio of the one or more carotenoids to the sesquiterpene is between about 0.001 to 2% by weight or between about 0.1 to about 1% by weight.

13. The method for co-production of isoprenoids of claim 1, wherein the host cell co-produces about 100 g to about 5000 g of the first isoprenoid and about 1 g to about 50 g of the second isoprenoid, each per kilogram of dry cell mass.

14. The method for co-production of isoprenoids of claim 1, wherein the amount of the first isoprenoid produced during co-production with the second isoprenoid is at least about 90% of the amount of the first isoprenoid produced by a parent host cell, wherein said parent host cell is genetically modified to produce the first isoprenoid but not the second isoprenoid.

15. The method for co-production of isoprenoids of claim 1, wherein the amount of the first isoprenoid produced during co-production with the second isoprenoid is at least about 95% of the amount of the first isoprenoid produced under the same culture conditions but without co-production of the second isoprenoid.

16. The method for co-production of isoprenoids of claim 1, wherein a cell density of the host cell during co-production of the first isoprenoid and the second isoprenoid is at least about 90% or 95% of a cell density of a parent host cell which is genetically modified to produce the first isoprenoid but not the second isoprenoid.

17. The method for co-production of isoprenoids of claim 1, wherein the first isoprenoid is a sesquiterpene and the second isoprenoid is a carotenoid, wherein a carbon flux towards the production of carotenoid is reduced compared to a carbon flux towards the production of sesquiterpene.

18. The method for co-production of isoprenoids of claim 1, wherein the second isoprenoid is lycopene, and the host cell comprises:
    (a) a heterologous nucleic acid encoding a phytoene synthase; and
    (b) a heterologous nucleic acid encoding a phytoene desaturase.

19. The method for co-production of isoprenoids of claim 1, wherein the second isoprenoid is β-carotene, and the host cell comprises:
    (a) at least one of:
        (i) a heterologous nucleic acid encoding a phytoene synthase;
        (ii) a heterologous nucleic acid encoding a lycopene cyclase; or
        (iii) a heterologous nucleic acid encoding a bifunctional enzyme having phytoene synthase and lycopene cyclase activities; and
    (b) a heterologous nucleic acid encoding a phytoene desaturase.

20. The method for co-production of isoprenoids of claim 1, wherein the second isoprenoid is cantaxanthin, and the host cell comprises:
    (a) at least one of:
        (i) a heterologous nucleic acid encoding a phytoene synthase;
        (ii) a heterologous nucleic acid encoding a lycopene cyclase; or
        (iii) a heterologous nucleic acid encoding a bifunctional enzyme having phytoene synthase and lycopene cyclase activities;
    (b) a heterologous nucleic acid encoding a phytoene desaturase; and
    (c) a heterologous nucleic acid encoding a β-carotene ketolase.

21. The method for co-production of isoprenoids of claim 1, wherein the second isoprenoid is zeaxanthin, and the host cell comprises:
    (a) at least one of:
        (i) a heterologous nucleic acid encoding a phytoene synthase;
        (ii) a heterologous nucleic acid encoding a lycopene cyclase; or
        (iii) a heterologous nucleic acid encoding a bifunctional enzyme having phytoene synthase and lycopene cyclase activities;
    (b) a heterologous nucleic acid encoding a phytoene desaturase; and
    (c) a heterologous nucleic acid encoding β-carotene hydroxylase.

22. The method for co-production of claim 1, wherein the second isoprenoid is astaxanthin, and the host cell comprises:
    (a) at least one of:
        (i) a heterologous nucleic acid encoding a phytoene synthase;
        (ii) a heterologous nucleic acid encoding a lycopene cyclase; or
        (iii) a heterologous nucleic acid encoding a bifunctional enzyme having phytoene synthase and lycopene cyclase activities;
    (b) a heterologous nucleic acid encoding a phytoene desaturase;
    (c) at least one of:
        (i) a heterologous nucleic acid encoding a β-carotene ketolase;
        (ii) a heterologous nucleic acid encoding a β-carotene hydroxylase;
        (iii) a heterologous nucleic acid encoding a cytochrome p450 hydroxylase and ketolase capable of converting β-carotene to echinenone and subsequently to β-cryptoxanthin and to astaxanthin; or
        (iv) a heterologous nucleic acid encoding a cytochrome p450 reductase which interacts with the cytochrome p450 hydroxylase and ketolase.

23. The method for co-production of isoprenoids of claim 1, wherein the second isoprenoid is lutein, and the host cell comprises:
    (a) a heterologous nucleic acid encoding a lycopene cyclase;
    (b) a heterologous nucleic acid encoding a δ-carotene β-cyclase;
    (c) a heterologous nucleic acid encoding β-ring hydroxylase; and
    (d) a heterologous nucleic acid encoding a carotene ε-monooxygenase.

24. The method for co-production of isoprenoids of claim 1, wherein the host cell further comprises a heterologous nucleic acid encoding a polyprenyl synthase for producing a polyprenyl diphosphate.

25. The method for co-production of isoprenoids of claim 24, wherein the host cell further comprises a heterologous nucleic acid encoding a farnesyl diphosphate (FPP) synthase, or a heterologous nucleic acid encoding a geranyl pyrophosphate (GGPP) synthase, or both.

26. The method for co-production of isoprenoids of claim 24, wherein the host cell further comprises a heterologous nucleic acid encoding a farnesyl diphosphate (FPP) synthase and comprises an endogenous nucleic acid encoding a geranyl pyrophosphate (GGPP) synthase but does not comprise a heterologous nucleic acid encoding a GGPP synthase.

27. The method for co-production of isoprenoids of claim 1, wherein the host cell further comprises one or more heterologous nucleic acids encoding one or more or all of the enzymes of the mevalonte pathway.

28. The method for co-production of isoprenoids of claim 1, wherein the host cell is a microbial cell.

29. The method for co-production of isoprenoids of claim 28, wherein the microbial host cell is a yeast.

30. The method for co-production of isoprenoids of claim 1, wherein the host cell is *Saccharomyces cerevisiae*.

31. The method for co-production of isoprenoids of claim 1, the method further comprising extracting and purifying the carotenoids.

32. A composition comprising purified carotenoids produced by the method of claim 1.

33. An animal feed comprising the microbial cell and the second isoprenoid produced from the method of claim 1.

34. A host cell comprising:
    (a) one or more heterologous nucleic acids encoding enzymes of a mevalonate pathway;
    (b) a heterologous nucleic acid encoding a biosynthetic pathway enzyme for production of sesquiterpene; and (c) a heterologous nucleic acid encoding a biosynthetic pathway enzyme for production of a carotenoid.

35. The host cell of claim 34 wherein the biosynthetic pathway enzyme for production of sesquiterpene is a synthase or synthetase.

36. The host cell of claim 34 that comprises one or more heterologous nucleic acids encoding enzymes of a pathway for production of the carotenoid.

37. A host cell comprising:
(a) a heterologous nucleic acid encoding a phytoene synthase;
(b) a heterologous nucleic acid encoding a phytoene desaturase;
or comprising:
(a) at least one of:
  (i) a heterologous nucleic acid encoding a phytoene synthase;
  (ii) a heterologous nucleic acid encoding a lycopene cyclase; or
  (iii) a heterologous nucleic acid encoding a bifunctional enzyme having phytoene synthase and lycopene cyclase activities; and
(b) a heterologous nucleic acid encoding a phytoene desaturase;
or comprising:
(a) at least one of:
  (i) a heterologous nucleic acid encoding a phytoene synthase;
  (ii) a heterologous nucleic acid encoding a lycopene cyclase; or
  (iii) a heterologous nucleic acid encoding a bifunctional enzyme having phytoene synthase and lycopene cyclase activities;
(b) a heterologous nucleic acid encoding a phytoene desaturase; and
(c) a heterologous nucleic acid encoding a β-carotene ketolase;
or comprising:
(a) at least one of:
  (i) a heterologous nucleic acid encoding a phytoene synthase;
  (ii) a heterologous nucleic acid encoding a lycopene cyclase; or
  (iii) a heterologous nucleic acid encoding a bifunctional enzyme having phytoene synthase and lycopene cyclase activities;
(b) a heterologous nucleic acid encoding a phytoene desaturase; and
(c) a heterologous nucleic acid encoding β-carotene hydroxylase;
or comprising:
(a) at least one of:
  (i) a heterologous nucleic acid encoding a phytoene synthase;
  (ii) a heterologous nucleic acid encoding a lycopene cyclase; or
  (iii) a heterologous nucleic acid encoding a bifunctional enzyme having phytoene synthase and lycopene cyclase activities;
(b) a heterologous nucleic acid encoding a phytoene desaturase;
(c) at least one of:
  (i) a heterologous nucleic acid encoding a β-carotene ketolase;
  (ii) a heterologous nucleic acid encoding a β-carotene hydroxylase;
  (iii) a heterologous nucleic acid encoding a cytochrome p450 hydroxylase and ketolase capable of converting β-carotene to echinenone and subsequently to β-cryptoxanthin and to astaxanthin; or
  (iv) a heterologous nucleic acid encoding a cytochrome p450 reductase
which interacts with the cytochrome p450 hydroxylase and ketolase;
or comprising:
(a) a heterologous nucleic acid encoding a lycopene cyclase;
(b) a heterologous nucleic acid encoding a δ-carotene β-cyclase;
(c) a heterologous nucleic acid encoding β-ring hydroxylase; and
(d) a heterologous nucleic acid encoding a carotene ε-monooxygenase;
the host cell optionally further comprising:
a heterologous nucleic acid encoding a polyprenyl synthase for producing a polyprenyl diphosphate; or
a heterologous nucleic acid encoding a FPP synthase, or a heterologous nucleic acid encoding a GGPP synthase, or both; or
one or more heterologous nucleic acids encoding one or more or all of the enzymes of the mevalonte pathway.

38. The method of claim 1, wherein at least 70%, 75%, 80%, 85%, 90%, or 95% of the first isoprenoid produced is found in the culture medium.

39. The method of claim 1, wherein at least 70%, 75%, 80%, 85%, 90%, or 95% of the second isoprenoid produced is associated with the host cell.

40. A method for co-production of two or more isoprenoids, the method comprising:
(a) culturing, in a culture medium, a host cell genetically modified with one or more heterologous nucleic acids encoding one or more enzymes in a first biosynthetic pathway to produce a first isoprenoid, and with one or more heterologous nucleic acids encoding one or more enzymes in a second biosynthetic pathway to produce a second isoprenoid, which has a molecular weight that is different from the first isoprenoid wherein the first isoprenoid is produced and secreted into the culture medium, and wherein the second isoprenoid is produced and remains associated with the host cell, wherein the first isoprenoid is a sesquiterpene and the second isoprenoid is one or more carotenoids; wherein the ratio of the one or more carotenoids to the sesquiterpene is between about 0.001 to 2% by weight or between about 0.1 to about 1% by weight;
(b) recovering the first isoprenoid from the culture medium; and
(c) recovering the second isoprenoid from the host cell.

* * * * *